(12) United States Patent
Tzannis et al.

(10) Patent No.: US 8,252,329 B2
(45) Date of Patent: *Aug. 28, 2012

(54) BIOADHESIVE DRUG FORMULATIONS FOR ORAL TRANSMUCOSAL DELIVERY

(75) Inventors: Stelios Tzannis, Newark, CA (US); Larry Hamel, Mountain View, CA (US); Pamela Palmer, San Francisco, CA (US); Thomas Schreck, Portola Valley, CA (US); Andrew I. Poutiatine, San Anselmo, CA (US)

(73) Assignee: Acelrx Pharmaceuticals, Inc., Redwood City, CA (US)

( * ) Notice: Subject to any disclaimer, the term of this patent is extended or adjusted under 35 U.S.C. 154(b) by 51 days.

This patent is subject to a terminal disclaimer.

(21) Appl. No.: 11/825,251

(22) Filed: Jul. 3, 2007

(65) Prior Publication Data

US 2008/0166404 A1    Jul. 10, 2008

(51) Int. Cl.
*A61K 9/20* (2006.01)

(52) U.S. Cl. .................................................. 424/464

(58) Field of Classification Search .................. None
See application file for complete search history.

(56) References Cited

U.S. PATENT DOCUMENTS

| | | | |
|---|---|---|---|
| 2,621,655 A | 12/1952 | Olson et al. |
| 4,229,447 A | 10/1980 | Porter |
| 4,237,884 A | 12/1980 | Erikson |
| 4,582,835 A | 4/1986 | Lewis et al. |
| 4,671,953 A | 6/1987 | Stanley |
| 4,863,737 A | 9/1989 | Stanley |
| 4,873,076 A | 10/1989 | Fishman |
| 4,880,634 A | 11/1989 | Speiser et al. |
| 5,080,903 A | 1/1992 | Ayache |
| 5,112,616 A | 5/1992 | McCarty et al. |
| 5,122,127 A | 6/1992 | Stanley |
| 5,132,114 A | 7/1992 | Stanley |
| 5,178,878 A | 1/1993 | Wehling |
| 5,223,264 A | 6/1993 | Wehling et al. |
| 5,236,714 A | 8/1993 | Lee |
| 5,288,497 A | 2/1994 | Stanley |
| 5,288,498 A | 2/1994 | Stanley |
| 5,296,234 A | 3/1994 | Hadaway |
| 5,348,158 A | 9/1994 | Honan et al. |
| 5,482,965 A | 1/1996 | Rajadhaks et al. |
| 5,507,277 A | 4/1996 | Rubsamen |
| 5,657,748 A | 8/1997 | Braithwaite et al. |
| 5,694,919 A | 12/1997 | Rubsamen |
| 5,710,551 A | 1/1998 | Ridgeway |
| 5,724,957 A | 3/1998 | Rubsamen |
| 5,735,263 A | 4/1998 | Rubsamen |

(Continued)

FOREIGN PATENT DOCUMENTS

EP    2114383    7/2010

(Continued)

OTHER PUBLICATIONS

Bredenberg et al., Eur. J. Pharm. Sci., 2003, 20, pp. 327-334.*

(Continued)

*Primary Examiner* — Brian Gulledge
(74) *Attorney, Agent, or Firm* — Cooley LLP

(57) ABSTRACT

Bioadhesive drug formulations that adhere to an oral mucosal membrane of a subject are provided together with single dose applicators and devices for delivering the drug formulations to the oral mucosa, and methods for using the same.

26 Claims, 12 Drawing Sheets

U.S. PATENT DOCUMENTS

| | | |
|---|---|---|
| 5,752,620 A | 5/1998 | Pearson |
| 5,785,989 A | 7/1998 | Stanley |
| 5,800,832 A | 9/1998 | Tapolsky et al. |
| 5,827,525 A | 10/1998 | Liao |
| 5,850,937 A | 12/1998 | Rauche et al. |
| 5,855,908 A | 1/1999 | Stanley et al. |
| 5,945,651 A | 8/1999 | Chorosinski |
| 5,950,632 A | 9/1999 | Reber et al. |
| 5,954,641 A | 9/1999 | Kehr et al. |
| 5,968,547 A | 10/1999 | Reder et al. |
| 5,981,552 A | 11/1999 | Alam |
| 5,995,938 A | 11/1999 | Whaley |
| 5,997,518 A | 12/1999 | Laibovitz et al. |
| 6,024,981 A | 2/2000 | Khankari |
| 6,039,251 A | 3/2000 | Holowko |
| 6,171,294 B1 | 1/2001 | Southam et al. |
| 6,190,326 B1 | 2/2001 | McKinnon |
| 6,200,604 B1 | 3/2001 | Pather |
| 6,210,699 B1 | 4/2001 | Acharya |
| 6,216,033 B1 | 4/2001 | Southam et al. |
| 6,230,927 B1 | 5/2001 | Schoonen et al. |
| 6,234,343 B1 | 5/2001 | Papp et al. |
| 6,248,789 B1 | 6/2001 | Weg |
| 6,264,981 B1 * | 7/2001 | Zhang et al. ............... 424/451 |
| 6,294,999 B1 | 9/2001 | Yarin et al. |
| 6,310,072 B1 | 10/2001 | Smith |
| 6,319,510 B1 | 11/2001 | Yates |
| 6,350,470 B1 | 2/2002 | Pather |
| 6,358,944 B1 | 3/2002 | Lederman |
| 6,391,335 B1 | 5/2002 | Pather |
| 6,417,184 B1 | 7/2002 | Ockert |
| 6,425,892 B2 | 7/2002 | Southam et al. |
| 6,484,718 B1 | 11/2002 | Schaeffer et al. |
| 6,495,120 B2 | 12/2002 | McCoy |
| 6,500,456 B1 | 12/2002 | Capella |
| 6,509,036 B2 | 1/2003 | Pather |
| 6,541,021 B1 | 4/2003 | Johnson et al. |
| 6,576,250 B1 | 6/2003 | Pather et al. |
| 6,605,060 B1 | 8/2003 | O'Neil |
| 6,607,750 B2 * | 8/2003 | Upadhyay et al. ............ 424/464 |
| 6,641,838 B2 | 11/2003 | Pather |
| 6,642,258 B1 | 11/2003 | Bourrie |
| 6,645,528 B1 | 11/2003 | Straub |
| 6,680,071 B1 | 1/2004 | Johnson et al. |
| 6,685,951 B2 | 2/2004 | Cutler |
| 6,689,373 B2 | 2/2004 | Johnson et al. |
| 6,752,145 B1 | 6/2004 | Bonney et al. |
| 6,759,059 B1 | 7/2004 | Pettersson |
| 6,761,910 B1 | 7/2004 | Pettersson |
| 6,762,684 B1 | 7/2004 | Camhi |
| 6,764,696 B2 | 7/2004 | Pather |
| 6,776,978 B2 | 8/2004 | Rabinowitz et al. |
| 6,793,075 B1 | 9/2004 | Jeter et al. |
| 6,796,429 B2 | 9/2004 | Cameron |
| 6,824,512 B2 | 11/2004 | Warkentin |
| 6,835,194 B2 | 12/2004 | Johnson et al. |
| 6,855,310 B2 | 2/2005 | Rabinowitz et al. |
| 6,881,208 B1 | 4/2005 | Phipps et al. |
| 6,914,668 B2 | 7/2005 | Brestel |
| 6,916,485 B2 | 7/2005 | Aiache et al. |
| 6,932,983 B1 | 8/2005 | Straub |
| 6,959,808 B2 | 11/2005 | Discko |
| 6,961,541 B2 | 11/2005 | Overy et al. |
| 6,963,289 B2 | 11/2005 | Aljadeff et al. |
| 6,969,508 B2 | 11/2005 | Dugger, III et al. |
| 6,974,590 B2 | 12/2005 | Pather |
| 6,999,028 B2 | 2/2006 | Egbert et al. |
| 7,018,370 B2 | 3/2006 | Southam et al. |
| 7,018,619 B2 | 3/2006 | Rabinowitz et al. |
| 7,044,125 B2 | 5/2006 | Vedrine |
| 7,044,302 B2 | 5/2006 | Conley et al. |
| 7,070,762 B2 | 7/2006 | Rabinowitz et al. |
| 7,070,764 B2 | 7/2006 | Rabinowitz et al. |
| 7,070,765 B2 | 7/2006 | Rabinowitz et al. |
| 7,072,738 B2 | 7/2006 | Bonney et al. |
| 7,074,935 B2 | 7/2006 | Mathew |
| 7,078,018 B2 | 7/2006 | Rabinowitz et al. |
| 7,078,019 B2 | 7/2006 | Rabinowitz et al. |
| 7,090,830 B2 | 8/2006 | Hale |
| 7,090,866 B2 | 8/2006 | Johnson |
| 7,119,690 B2 | 10/2006 | Lerch et al. |
| 7,168,626 B2 | 1/2007 | Lerch et al. |
| 7,169,378 B2 | 1/2007 | Rabinowitz et al. |
| 7,198,172 B2 | 4/2007 | Harvey et al. |
| 7,208,604 B2 | 4/2007 | Mathew |
| 7,215,295 B2 | 5/2007 | Egbert et al. |
| 7,248,165 B2 | 7/2007 | Collins et al. |
| 7,276,246 B2 | 10/2007 | Zhang et al. |
| 7,295,890 B2 | 11/2007 | Jean-Pierre et al. |
| 7,306,812 B2 | 12/2007 | Zhang et al. |
| 7,458,374 B2 | 12/2008 | Hale et al. |
| 7,468,179 B2 | 12/2008 | Rabinowitz et al. |
| 2001/0020147 A1 | 9/2001 | Staniforth et al. |
| 2002/0026330 A1 | 2/2002 | Klein et al. |
| 2002/0037491 A1 | 3/2002 | Halliday |
| 2002/0071857 A1 * | 6/2002 | Kararli et al. ................. 424/435 |
| 2002/0110578 A1 | 8/2002 | Pather et al. |
| 2002/0142050 A1 | 10/2002 | Straub |
| 2002/0160043 A1 | 10/2002 | Coleman |
| 2003/0008005 A1 | 1/2003 | Cutler |
| 2003/0015196 A1 | 1/2003 | Hodges et al. |
| 2003/0015197 A1 | 1/2003 | Hale |
| 2003/0017175 A1 | 1/2003 | Cutler |
| 2003/0017994 A1 | 1/2003 | Cutler |
| 2003/0022910 A1 | 1/2003 | Cutler |
| 2003/0035776 A1 | 2/2003 | Hodges |
| 2003/0052135 A1 | 3/2003 | Conley et al. |
| 2003/0052787 A1 | 3/2003 | Zerhusen et al. |
| 2003/0077300 A1 | 4/2003 | Wermeling et al. |
| 2003/0088236 A1 | 5/2003 | Johnson et al. |
| 2003/0091629 A1 | 5/2003 | Pather et al. |
| 2003/0130314 A1 | 7/2003 | Druzgala |
| 2003/0132239 A1 | 7/2003 | Konig et al. |
| 2003/0171401 A1 | 9/2003 | Johnson et al. |
| 2003/0185872 A1 | 10/2003 | Kochinke et al. |
| 2003/0190290 A1 | 10/2003 | Ross |
| 2003/0232080 A1 | 12/2003 | Pather et al. |
| 2004/0017567 A1 | 1/2004 | Loicht et al. |
| 2004/0025871 A1 | 2/2004 | Davies et al. |
| 2004/0034059 A1 | 2/2004 | Grarup et al. |
| 2004/0037882 A1 | 2/2004 | Johnson |
| 2004/0080515 A1 | 4/2004 | Hagiwara et al. |
| 2004/0092531 A1 | 5/2004 | Chizh |
| 2004/0094564 A1 | 5/2004 | Papp et al. |
| 2004/0096402 A1 | 5/2004 | Hodges et al. |
| 2004/0120896 A1 | 6/2004 | Dugger |
| 2004/0133305 A1 | 7/2004 | Jean-Pierre |
| 2004/0158349 A1 * | 8/2004 | Bonney et al. ................. 700/231 |
| 2004/0170567 A1 | 9/2004 | Sackler et al. |
| 2004/0180080 A1 * | 9/2004 | Furusawa et al. ............. 424/449 |
| 2004/0185003 A1 | 9/2004 | Rabinowitz et al. |
| 2004/0191178 A1 | 9/2004 | Cutler |
| 2004/0202617 A1 | 10/2004 | Rabinowitz et al. |
| 2004/0213855 A1 | 10/2004 | Pettersson |
| 2004/0248964 A1 | 12/2004 | Crooks |
| 2004/0253307 A1 | 12/2004 | Hauge et al. |
| 2005/0038062 A1 | 2/2005 | Burns |
| 2005/0049464 A1 | 3/2005 | Lassers |
| 2005/0054942 A1 | 3/2005 | Melker |
| 2005/0064030 A1 | 3/2005 | Pather et al. |
| 2005/0065175 A1 | 3/2005 | Gonzales et al. |
| 2005/0075273 A1 | 4/2005 | Rabinowitz et al. |
| 2005/0089479 A1 | 4/2005 | Rabinowitz et al. |
| 2005/0101936 A1 | 5/2005 | Gonzales et al. |
| 2005/0131337 A1 | 6/2005 | Phipps et al. |
| 2005/0142197 A1 | 6/2005 | Moe |
| 2005/0142198 A1 | 6/2005 | Moe |
| 2005/0150488 A1 | 7/2005 | Dave et al. |
| 2005/0163838 A1 | 7/2005 | Moe |
| 2005/0169989 A1 | 8/2005 | Agarwal et al. |
| 2005/0171464 A1 | 8/2005 | Phipps et al. |
| 2005/0176790 A1 | 8/2005 | Bartholomaus |
| 2005/0258066 A1 | 11/2005 | Conley et al. |
| 2006/0026035 A1 | 2/2006 | Younkes |
| 2006/0039959 A1 | 2/2006 | Wessling |
| 2006/0045865 A1 | 3/2006 | Jacob et al. |
| 2006/0062812 A1 | 3/2006 | Ross |

| | | | |
|---|---|---|---|
| 2006/0067978 A1 | 3/2006 | Heiler et al. |
| 2006/0069344 A1 | 3/2006 | Southam et al. |
| 2006/0089858 A1 | 4/2006 | Ling |
| 2006/0134200 A1 | 6/2006 | Vandoni et al. |
| 2006/0216352 A1 | 9/2006 | Nystrom |
| 2006/0229570 A1 | 10/2006 | Lovell |
| 2006/0233718 A1 | 10/2006 | Rabinowitz et al. |
| 2006/0251587 A1 | 11/2006 | Rabinowitz et al. |
| 2006/0292219 A1 | 12/2006 | Pather |
| 2007/0020186 A1 | 1/2007 | Stroppolo |
| 2007/0031502 A1 | 2/2007 | Pettersson |
| 2007/0036853 A1 | 2/2007 | Agarwal |
| 2007/0071806 A1 | 3/2007 | McCarty et al. |
| 2007/0074722 A1 | 4/2007 | Giroux |
| 2007/0104763 A1 | 5/2007 | Jobdevairakkam et al. |
| 2007/0178052 A1 | 8/2007 | Rabinowitz et al. |
| 2007/0185084 A1 | 8/2007 | McKinney |
| 2007/0190130 A1 | 8/2007 | Mark |
| 2007/0286900 A1 | 12/2007 | Herry |

FOREIGN PATENT DOCUMENTS

| | | |
|---|---|---|
| GB | 2309966 | 8/1997 |
| WO | WO 00/16750 | 3/2000 |
| WO | WO 00/57858 | 10/2000 |
| WO | 0130288 | 5/2001 |
| WO | 0197780 | 12/2001 |
| WO | 2004069198 | 8/2004 |
| WO | 2004080515 | 9/2004 |
| WO | WO2006097361 | 9/2006 |

OTHER PUBLICATIONS

Weinber et al., Clin. Pharmacol. Ther., 1988, 44(3), pp. 335-342.*
Siepmann et al., Int. J. Pharm., 2000, 201(1), pp. 151-164.*
"FDA Guidance for Industry: Container Closure Systems for Packaging Human Drugs and Biologics," May 1999, pp. 1-E2.*
Bethune-Volters, A Randomlized, Double-Blind Trial Assessing the Efficacy and Safety of Sublingual Metopimazine and Ondansetron in the Prophyaxis of chemotherapy-Induced Delayed Emesis.
Brendenberg, "New Concepts in Administration of Drugs in Tablet Form—Formulations and Evaluation of a Sublingual Tablet for Rapid Absorption, and Presentation of an Individualised Dose Administration System", Comprehensive Summaries of Uppsala Dissertations from the Faculty of Pharmacy 287, ACTA Universitatis Upsaliensis Uppsala.
Chauvin, M., "Sufentanil Pharmacokinetics in Patients With Cirrhosis", Anesthes Analg, 1989, 68(1):1-4.
Coluzzi P.H., et al., Breakthrough Cancer Pain: A Randomized Trial Comparing Oral Transmucosal Fentanyl Citrate (OTFC) and Morphine Sulfate Immediate Release (MSIR), Pain, 2001, 91(1-2):123-130.
Darwish, "Phamacokinetic Properties of Fentanyl Effervescent Buccal Tablets: A Phase I, Open-Label, Crossover Study of Single-Dose 100, 200, 400 and 800 Microg in Health Adult Volunteers" Clinical Therapies, 2006, 28(5):707-714.
Darwish, M., "Comparison of Equivalent Doses of Fentanyl Buccal Tablets and Arteriovenous Differences in Fentanyl Pharmacokinetics", Clin Pharmacokinet, 2006, 45(8):843-850.
Durfee, Fentanyl Effervescent Buccal Tablets: Enhanced Buccal Absorption, American Journal of Drug Delivery, 2006, 4(1):1-5(5).
Egan, T.D., Multiple Dose Pharmacokinetics of Oral Transmucosal Fentanyl Citrate in Healthy Volunteers, Anesthesiology, 2000, 92:665-673.
Farnsworth, S.T., et al., "Ocular Transmucosal Absorption and Toxicity of Sufentanil in Dogs", Anesth Analg, 1998, 86:138-140.
Gardner-Nix J., "Oral Transmucosal Fentanyl and Sufentanil for Incident Pain", J Pain Symptom Management, Aug. 2001, 22(2):627-630.
Geldner, G., et al., "Comparison Between Three Transmucosal Routes of Administration of Midazolam in Children", Paediatr Anaesth, 1997, 7(2):103-109.
Gerak, L.R., "Studies on Benzodiazepines and Opioids Administered Alone and in Combination in Rhesus Monkeys: Ventilation and Drug Discrimination", Psychopharmacology, 1998, 137:164-174.

Gordon, D.B., Oral Transmucosal Fentanyl Citrate for Cancer Breakthrough Pain: A Review, Oncol Nurs Forum, Nov. 3, 2006, 33(2)257-264.
Gram-Hansen P., "Plasma Concentrations Following Oral and Sublingual Administration of Lorazepam", Int J. Clin Pharmacol Ther Toxical, 1988, 26(6):323-324.
Haynes, G., "Plasma Sufentantil Concentration After Intranasal Administration to Paediatric Outpatients", Can J. Anaesth, 1993, 40(3):286.
Helmers, et al., 1989, Can J. Anaesth, 1989, 6:494-497.
Jackson K., et al., "Pilot Dose Finding Study of Intranasal Sufentanil for Breakthrough and Incident Cancer-Associated Pain", J Pain Symptom Manage, 2002, 23(6):450-452.
Jackson, "Pharmacokinetics and Clinical Effects of Multidose Sublingual Triazolam in Healthy Volunteers" J Clin Psychopharmacol, Feb. 2006, 26(1):4-8.
James, et al., "The Use of a Short-Acting Benzodiazepine to Reduce the Risk of Syncopal Episodes During Upright Sterotactic Breast Biopsy", Clin Radiol, Mar. 2005, 60(3):394-396.
Jeannet, et al., "Home and Hospital Treatment of Acute Seizures in Children with Nasal Midazolam", Eur J. Paediatr Neurol, 1999, 3(2):73-77.
Kaplan, G.B., "Single Dose Pharmacokinetics and Pharmacodynamics of Alprazolam in Elderly and Young Subjects", PubMed, 1998, 38(1):14-21.
Karl, et al., "Comparison of the Safety and Efficacy of Intranasal Midazolam of Sufentanil for Preinduction of Anesthesia in Pediatric Patients", Anesthesiology, 1992, 76:209-215.
Karl, H.W ., Transmucosal Administration of Midazolam for Premedication of Pediatric Patients, Anesthesiology, 1993, 78(5):885-891.
Khalil, et al., "Sublingual Midazolam Premedication in Children: A Dose Response Study", Paediatr Anaesth, 1998, 8(6):461-465.
Kogan, et al., "Premedication with Midazolam in Young Children: A Comparison of four Routes of Administration", Paediatr Anaesth Oct. 2002, 12(8):685-689.
Kontinen, et al., "Premedication With Sublingual Triazolam Compared With Oral Diazepam", Canadian Journal of Anesthesia, 1993, 40:829-834.
Kroboth, P.D., "Triazolam Pharmacokinetics After Intravenous, Oral and Sublingual Administration", J Clin Psychophamacol, 1995, 15(4):259-262.
Kunz, K.M., "Severe Episodic Pain: Management With Sublingual Sufentanil", Journal of Pain and Symptom Management, 1993, 8:189-190.
Lennernäs B., "Pharmacokinetics and Tolerability of Different Doses of Fentanyl Following Sublingual Administration of a Rapidly Dissolving Tablet to Cancer Patients: A New Approach to Treatment of Incident Pain", Br J Clin Pharmacol, Feb. 2005, 59(2):249-253.
Lichtor, J.L., "The Relative Potency of Oral Transmucosal Fentanyl Citrate (OTFC) Compared With Intravenous Morphine in the Treatment of Moderate to Severe Postoperative Pain" Anesth Anal, 1999, 89(3):732-738.
Lipworth, et al., Pharmacokinetics, Effacacy and Adverse Efects of Sublingual Salbutamol in Patients with Asthma, European Journal of Clinical Pharmacology, Nov. 1989, 37(6).
Mathieu, N., et al., "Intranasal Sufentanil is Effective for Postoperative analgesia in Adults", Can J Anesth, 2006, 53(1):60-66.
McCann and Kain, "The Management of Preoperative Anxiety in Children: an Update", Anesthesia & Analgesia, 2001, 93:98-105.
Monk, J.P., "Sufentanil: A Review of Its Pharmacological Properties and Therapeutic Use", Drugs, 1988, 36:286-313.
Naguib, et al. "The Comparative Dose-Response Effects fo Melatonin and Midazolam for Premedication of Adult Patients: A Double-Blinded, Placebo-Controlled Study", Anesth Analg, Aug. 2000, 91(2):473-479.
Odou, C., et al., "Development of Midazolam Sublingual Tablets: In Vitro Study", Eur J Drug Metab Pharmacokinet, Apr.-Jun. 1998, 23(2):87-91.
Okayama, et al, "Bronchodilator Effect of Sublingual Isosorbide Dinitrate in Asthma", Eur J Clin Pharmacol, 1984, 26(2):151-155.

Roy, S.D., "Transdermal Delivery of Narcotic Analgesics: pH, Anatomical, and Subject Influences on Cutaneous Permeability of Fentanyl and Sufentanil", Pharm Res, 1990, 7:842-847.
Scavone, J.M., "The Pharmacokinectics and Pharmacodynamics of Sublingual and Oral Alprazolam in the Post-Pradial State", Eur J Clin Pharmacol, 1992, 42(4):439-443.
Scavone, J.M., et al, "Enhanced Bioavailibility of Triazolam Following Sublingual Versus Oral Administration", J Clin Pharmacol, Mar. 1986, 26(3):208-210.
Schreiber, K.M., "The Association of Preprocedural anxiety and the Success of Procedural Sedation inChildren", Am J Emerg Med, Jul. 2006, 24(4):397-401.
Schwagmeier, R., "Midazolam Pharmacokinetics Following Intravenous and Buccal Administration", Br J Clin Pharmacol, 1998, 46:203-206.
Sinatra, R.S., "Patient-Controlled Analgesia with Sufentanil: A Comparison of Two Different Methods of Administration", Journal of Clinical Anesthesia, 1996, 8:123-129.
Tweedy, C.M., "Pharmacokinetics and Clinical Effects of Sublingual Triazolam in Pediatric Dental Patients" J Clin Psychopharmacol, 2001, 21(3):268-272.
Vercauteren M., "Intranasal Sufentanil for Pre-Operative Sedation", Anaesthesia, 1988, 43(4):270-273.
Viitanen, et al, "Medazolam Premedication Delays Recovery from Propofol-Induced Sevoflurane Anesthesia in Children 1-3 yr", Canadian Journal of Anaesthesia, 1999, 46:766-71.
Weniberg, D.S., Sublingual Absorption of Selected Opioid Analgesics, Clin Parmacol Ther, Sep. 1988, 44(3):335-342.
Wheeler, M., "Uptake Pharmacokinetics of the Fentanyl Oralet in Children Scheduled for Central Venous Access Removal: Implications for the timing of Initiating Painful Procedures", Paediatric Anesthesia, 2002, 12:594-599.
Willens, J.S., "Pharmacodynamics, Pharmacokinetics, and Clinical Uses of Fentanyl, Sufentanil, and Alfentanil", Heart and Lung, 1993, 22:239-251.
Yager J.Y., "Sublingual Lorazepam in Childhood Serial Seizures", Am J Dis Child, 1988, 142:931-932.
Zedie, N., "Comparison of Intranasal Midazolam and Sufentanil Premedication in Pediatric Outpatients", Clin Parmacol and Therapeutics, 1996, 59:341-348.
Zhang, H., "Oral Mucosal Drug Delivery: Clinical Pharmacokinetics and Therapeutic Applications", Clinical Pharmacokinetics, 2002, 41(9):661-680(20).
Actiq package insert—ACTIQ® is an oral Transmucosal form of fentanyl citrate administered as a lollipop, both indicated for the management of breakthrough cancer pain in patients who are already receiving and who are tolerant to opioid therapy. The Actiq package insert claims that at least 75% of the drug dose is swallowed via the saliva and thus enters the circulation via the GI tract. See p. 4.
Fentora package insert—100-800mcg dose of fentanyl; buccal absorption with approximately 50% of the total dose absorbed transmucosal and the remaining half of the dose is swallowed and undergoes absorptions via the GI tract. See p. 4.
International Search Report and Written Opinion dated Dec. 17, 2007 issued in PCT/2007/00527 (WO/2007/081947).
International Search Report and Written Opinion dated Feb. 4, 2008 issued in PCT/2007/00528 (WO/2007/081948).
Berthold et.al.; "Comparison of sublingually and orally administered triazolam for premedication before oral surgery"; Oral Surg Oral Med Oral Pathol Oral Radiol Endod; 1997; 84(2):119-24.
Bredenberg et al; "In vitro and in vivo evaluation of a new sublingual tablet system for rapid or mucosal absorption using fentanyl citrate as the active substance"; European Journal of Pharmaceutical Sciences; 2003; 327-334.
Darwish et al.; "Bioequivalence following buccal and sublingual placement of fentanyl buccal tablet 400mcg in healthy subjects"; Clin. Drug Invest. 2008: 28(1): 1-7.
Darwish et al.; "Effect of buccal dwell time on the pharmacokinetic profile of fentanyl buccal tablet"; Expert Opin Pharmacother Sep. 2007;8(13):2011-6. Review.
Darwish et al.; "Comparison of equivalent doses of fentanyl buccal tablets and arteriovenous differences in fentanyl pharmacokinetics"; Clinical Pharmacokinetics; 2006; 45(8): 843-50.

Darwish et al.; "Relative bioavailability of the fentanyl effervescent buccal tablet (FEBT) 1,080 pg versus oral transmucosal fentanyl citrate 1,600 pg and dose proportionality of FEBT 270 to 1,300 microg: a single dose, randomized, open-label, three period study in healthy adult volunteers"; Clinical Therapies; 2006; 28(5):715-24.
Darwish et al.; "Pharmacokinetics and dose proportionality of fentanyl effervescent buccal tablets in healthy volunteers"; Clinical Pharmacokinetics; 2005; 44(12): 1279-86.
Karl et al.; "Pharmacokinetics of oral triazolam in children"; Journal Clinical Psychopharmacology; 1997; 17(3):169-172.
KGH Drug Information Service; "Sublingual Sufentanil for Incident Pain"; KGH Drug Information Bulletin, vol. 37(4) 2, 2004.
Odou et al.; "Pharmacokinetics of midazolam: comparison of sublingual and intravenous routes in rabbit"; Eur T Drug Metab Pharmacokinet; 1999; 24(1):1-7.
Stopperich et al.; "Oral triazolam pretreatment for intravenous sedation"; Anesth Prog. 1993 ;40(4): 117-21.
Yeomans et al.; "Sublingual Sufentanil"; Vancouver Hospital and Health Science Center Drug and Therapeutics Newsletter, vol. 8(1) 2, 2001.
Dale, et al., 2002, Acta Anaesth Scand, 46:759-770.
Darwish et al., 2007, J Clin Pharm 47: 56-63.
Demeules, et al., Eur J Anaesthesiol Suppl. 2003; 28:7-11.
Good, et al., 2009, Palliative Medicine, 23:54-58.
Henderson JM, et al.; Anesthesiology; 1988; 68:671-675.
Joshi, et al., 1993, Indian Pediatr, 30(1):84-5.
Karl, et al., 1993, Anesthesiology, 78(5):885-91.
Lim, et al., 1997, Can J Anaesth, 44(7):723-6.
Mendelson J, et al.; J Clin Pharmacol; 1997; 37:31-7.
Motwani JG, Lipworth BJ; Clin Pharmacokinet; 1991; 21(2):83-94.
Mystakidou K, et al.; Drug Deliv. 2006; 13(4):269-76.
Nath RP, et al.; J Clin Pharmacol; 1999; 39:619-23.
Pavlin, et al., Anesthesiology. Jan. 1996; 84(1):23-37.
Portenoy RK, et al.; Pain; 1999; 79:303-12.
Raza, et al., Can J Anaesth. Nov. 1989; 36(6):617-23.
Reisfield G, Wilson G; Journal of Palliative Medicine; 2007; 10(2):465-475.
Roy, SD and Flynn, GL; Pharm Research; 1989; 6(2): 147-151.
Scavone, et al., 1987, J Clin Psychpharmacol, 7(5):332-4.
Scholz J, et al.; Clin Pharmacokin ; 1996; 31:275-292.
Streisand JB, et al.; Anesthesiology; 1991; 75:223-9.
Streisand JB, et al.; Anesthesiology; 1998; 88:305-9.
Sufenta Package Insert, 2006.
Viitanen, et al., 1999, Can J Anesth, 46(8):766-771.
Office Action for U.S. Appl. No. 11/429,904, mailed Sep. 17, 2008.
Office Action for U.S. Appl. No. 11/980,216, mailed Dec. 24, 2008.
Office Action for U.S. Appl. No. 11/650,230, mailed Sep. 25, 2008.
Office Action for U.S. Appl. No. 11/650,230, Mar. 10, 2009.
Office Action for U.S. Appl. No. 11/429,904, mailed Mar. 5, 2009.
Office Action for U.S. Appl. No. 11/650,227, mailed Dec. 9, 2008.
Office Action for U.S. Appl. No. 11/473,551, mailed Mar. 16, 2009.
Office Action for U.S. Appl. No. 11/473,551, mailed Sep. 26, 2008.
Office Action for U.S. Appl. No. 11/650,227, mailed Jul. 6, 2009.
Office Action for U.S. Appl. No. 11/980,216, mailed Jul. 20, 2009.
ISR WO2008/085764, mailed Jun. 23, 2008.
ISR WO2008/072445 (AceIRx7PCT), mailed Oct. 20, 2008.
ISR WO2007/133478 (AceIRx2 PCT), mailed Aug. 5, 2008.
ISR WO2008/002358 (AceIRx3 PCT), mailed Aug. 21, 2008.
ISR WO2007/081949 (AceIRx6 PCT), mailed Sep. 11, 2007.
ISR WO2008/085765 (AceIRx6CIP2 PCT), mailed Oct. 15, 2008.
Office Action for U.S. Appl. No. 11/650,230, mailed Aug. 4, 2009.
Office Action for U.S. Appl. No. 11/974,092, mailed Sep. 30, 2009.
Office Action for U.S. Appl. No. 11/473,551 (08-1133), mailed Sep. 11, 2009.
Office Action for U.S. Appl. No. 11/429,904 (08-1134), mailed Aug. 20, 2009.
AHFS Drug Information, 28:08.08, 2157-2160, 2007.
Anlar S et al., Pharm Res, 11(2):231-6, 1994.
Bovill GJ, et al., Anesthesia, 61:502-506, 1984.
De Castro J, et al., Acta Anesth Belgica, 107-128, 1976.
de Vries M et al., Critical Reviews in Therapeutic Drug Carrier Systems, 8(3):271-303, 1991.

Enting H. R, et al., J. Pain and Symptom Management, 29(2):213-217, 2005.
Good P, et al., Palliat Med., 23(1):54-58, 2009.
Guay J, Can J Anaesth, 39(1): 14-20, 1992.
Halliburton JR, Anesthesiology, 61(5):502-506, 1984.
Hazardous Substances Data Bank (HSDB); (http://toxnet.nlm.nih.gov) Apr. 9, 2007; Name: Sufentanil; RN: 56030-54-7.
Helmers JH, et al., Eur J Anesth, 11(3):181-5, 1992.
Ikinci G, et al., Int. J. Pharm, 277(1-2):173-8, 2004.
Kress, et al. Clinical Therapeutics, 31(6):1177-1191, 2009.
Mather, Clin. Exp. Pharmacol. Physiol., 22:833-836, 1994.
Molander L and Lunell E, Eur J Clin Pharmacol, 56(11):813-819, 2001.
Onsolis Package Insert Jul. 2009.
Portenoy RK, et al., Pain, 22(9):805-811, 2006.
Puig MM, et al., Int'l J Clin Pharmaco Ther and Toxicol, 27(5):229-34, 1989.
Reynolds, et al., 2004, Pain, 110:182-188.
Roscow, CE, Pharmacotherapy, 4:11-19, 1984.
Savoia G, et al., Minerva Anesth, 67(9 Suppl 1):206-16, 2001.
Office Action for U.S. Appl. No. 11/650,174 (AceIRx6), mailed Oct. 13, 2010.
Office Action for U.S. Appl. No. 11/650,227 (AceIRx4), mailed Dec. 15, 2009.
Office Action for U.S. Appl. No. 11/650,230 (AceIRx5), mailed Feb. 2, 2010.
Office Action for U.S. Appl. No. 11/650,230 (AceIRx5), mailed Jun. 16, 2010.
Office Action for U.S. Appl. No. 11/825,212 (AceIRx5CIP), mailed Mar. 24, 2010.
Office Action for U.S. Appl. No. 11/825,212 (AceIRx5CIP), mailed Aug. 31, 2010.
Office Action for U.S. Appl. No. 11/980,216 (AceIRx6CIP1), mailed Jan. 5, 2010.
Office Action for U.S. Appl. No. 11/980,216 (AceIRx6CIP1), mailed Jul. 2, 2010.
Office Action for U.S. Appl. No. 11/974,092 (AceIRx6CON1), mailed Mar. 31, 2010.
ISR WO2010/059504 (AceIRx9 PCT) mailed Mar. 17, 2010.
ISR WO2010/107761 (AceIRx10 PCT) mailed Jun. 21, 2010.
Office Action for U.S. Appl. No. 11/650,227 (AceIRx4), mailed Aug. 5, 2010.
Mather, Clin. Pharmacokinetics, 8: 422-446, 1983.

* cited by examiner

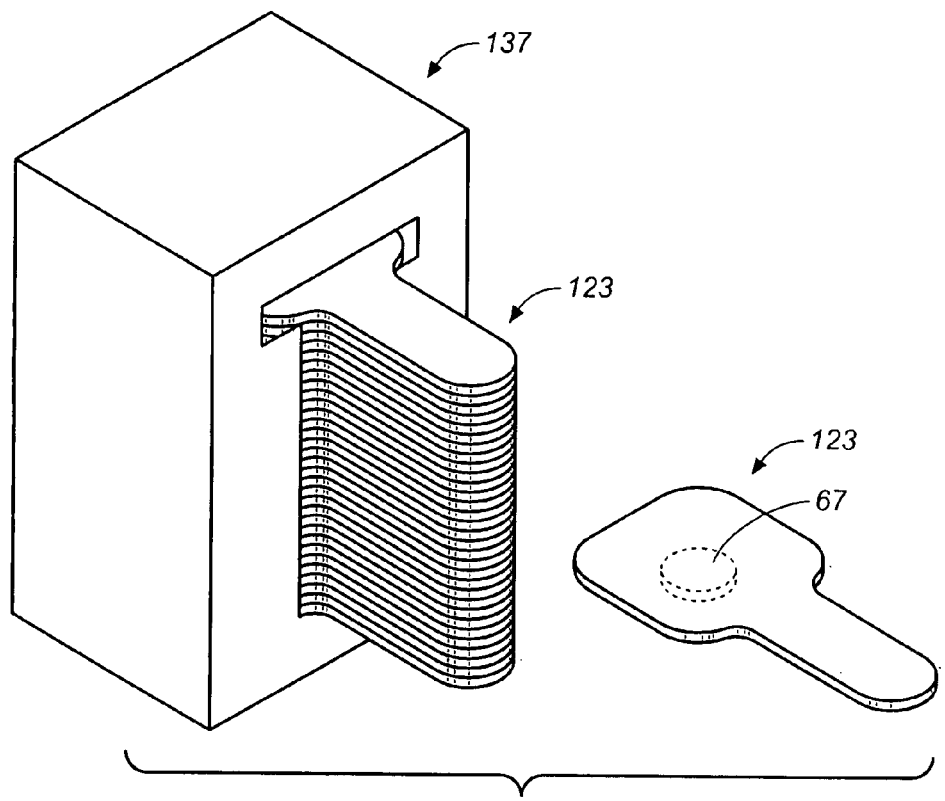
FIG. 17
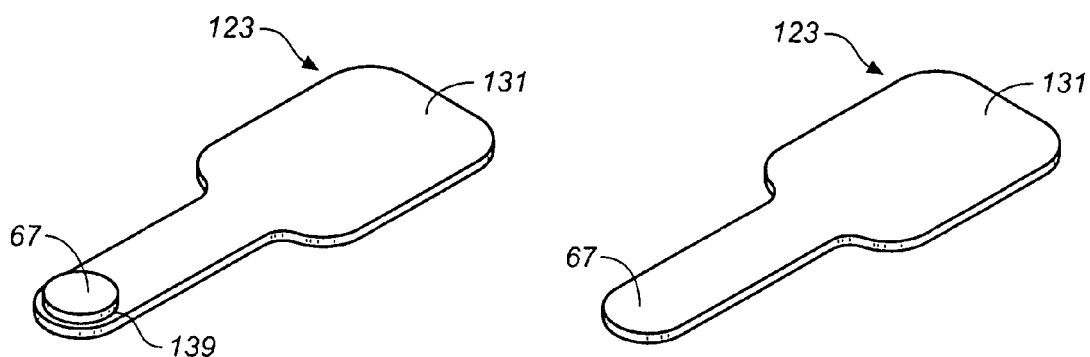
FIG. 18A  FIG. 18B

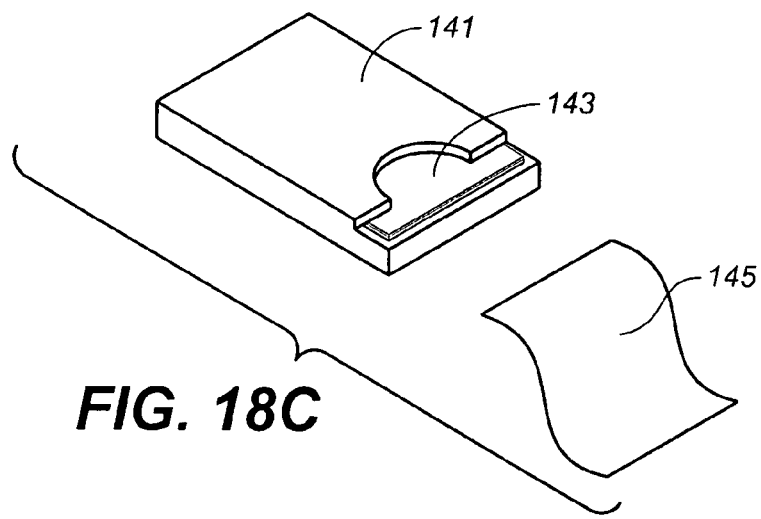
FIG. 18C
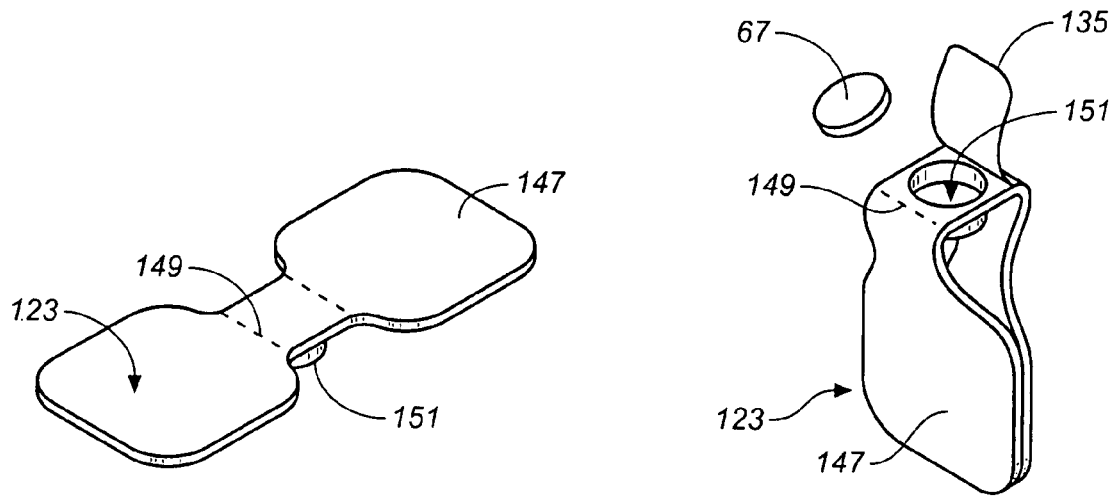
FIG. 19A  FIG. 19B

BIOADHESIVE DRUG FORMULATIONS FOR ORAL TRANSMUCOSAL DELIVERY

CROSS REFERENCE TO OTHER APPLICATIONS

This application claims the priority benefit of U.S. application Ser. No. 11/650,227, filed Jan. 5, 2007, which claims the priority benefit of U.S. Provisional Patent Application Ser. No. 60/756,937, filed Jan. 5, 2006, the disclosure of which are incorporated by reference in their entirety.

FIELD OF THE INVENTION

The present invention relates to formulations for oral transmucosal drug delivery and methods for delivery of medications across the oral mucosa using drug dosage forms comprising such formulations and methods for using the same.

BACKGROUND OF THE TECHNOLOGY

Oral dosage forms account for approximately eighty percent of all the drug dosage forms on the market. Oral dosage forms are non-invasive, easily administered and have high patient compliance.

Orally administered therapeutic agents are rapidly transported to the stomach and small intestine for absorption across the gastrointestinal (GI) mucosal membranes into the blood. The efficiency of absorption of a drug following oral administration can be low because of metabolism within the GI tract and first-pass metabolism within the liver resulting in relatively lengthy onset times or erratic absorption characteristics that are not well suited to control acute disorders. The majority of oral dosage forms on the market are designed for GI delivery. Relatively few oral dosage forms are designed for delivery through the oral mucosa.

However, oral transmucosal delivery offers a number of advantages in that it can provide a shorter onset time and more consistent time ($T_{max}$) to maximal plasma concentration ($C_{max}$) than oral delivery, in particular for lipophilic drugs. This is because the drug rapidly passes directly and efficiently through the epithelium of the highly vascularized mucosal tissue to the plasma, thus rapidly reaching the circulation while avoiding the slower, often inefficient and variable GI uptake. In addition, due to the avoidance of the first-pass metabolism and avoidance of inefficient drug absorption through the gut, sublingual drug uptake may improve drug bioavailability. It is therefore advantageous for a drug to be delivered through the mucus membranes of the oral cavity, (e.g., via the sublingual route), when rapid onset, consistent $T_{max}$ and $C_{max}$ are advantageous.

In carrying out oral transmucosal drug delivery, the drug is absorbed through the epithelial membranes of the oral cavity. However, frequently the key risk associated with oral transmucosal delivery is the enhanced potential for swallowing the medication owing to the continuous generation, backward flow and swallowing of the saliva. This becomes a particular risk when the used dosage forms are large, thereby producing increased saliva response, which, in turn, leads to increased swallowing and removal of the dosage form from the oral mucosa. The present invention provides the advantage that the formulations have bioadhesive properties which facilitate adherence to the oral mucosa during administration, thus minimizing the risk of ingestion and inefficient delivery potential.

Various solid dosage forms, such as sublingual tablets, troches, lozenges, lozenges-on-a-stick, chewing gums, and buccal patches, have been used to deliver drugs via the oral mucosal tissue. Solid dosage forms such as lozenges and tablets are commonly used for oral transmucosal delivery of drugs, e.g., nitroglycerin sublingual tablets.

Relevant formulations and delivery systems for oral or buccal administration of pain medication have been previously disclosed, for example, in: U.S. Pat. Nos. 2,698,822; 3,972,995; 3,870,790; 3,444,858; 3,632,743; 4,020,558; 4,229,447; 4,671,953; 4,836,737; and 5,785,989.

U.S. Patent Publication No. 20020160043 discloses compositions and methods of manufacture for dissolvable and non-dissolvable drug-containing dosage-forms for noninvasive administration of medications through mucosal tissues of the mouth, pharynx, and esophagus of a patient.

U.S. Pat. Nos. 4,671,953 and 5,785,989 (Stanley, et al.) disclose a lozenge-on-a-stick dosage form for transmucosal drug delivery. Once the appropriate amount of drug is delivered, the patient or caregiver can remove the lozenge, thus, stopping the drug delivery to prevent overdose.

U.S. Pat. No. 5,296,234 (Hadaway, et al.) discloses a stick-like holder and packaging, including a tamper resistant foil pouch, for a hardened, sucrose based matrix containing a dosage of fentanyl citrate affixed to one end of the holder and a flange to prevent swallowing of the holder when placed in a patient's mouth to medicate or pre-medicate the patient.

U.S. Pat. Nos. 6,974,590, 6,764,696, 6,641,838, 6,585,997, 6,509,036, 6,391,335, 6,350,470, 6,200,604 and US Patent Publication Nos. 20050176790, 20050142197 and 20050142198 describe pharmaceutical combinations of active compounds such as fentanyl and congeners thereof in combination with an effervescent agent used as penetration enhancer to influence the permeability of the active compound across the buccal, sublingual, and gingival mucosa.

U.S. Pat. No. 6,761,910 and U.S. Patent Publication No. 20040213855 disclose pharmaceutical compositions for the treatment of acute disorders by sublingual administration of an essentially water-free, ordered mixture of microparticles with at least one pharmaceutically active agent adhered to the surfaces of the carrier particles by way of a bioadhesion and/or mucoadhesion promoting agent.

U.S. Pat. No. 6,759,059 discloses compositions and methods for the treatment of acute pain by sublingual administration of compositions which contain from 0.05 to 20 mg fentanyl or a pharmaceutically acceptable salt thereof in the form of microparticles which are adhered to the surface of carrier particles by way of a bioadhesion and/or mucoadhesion promoting agent, wherein each tablet is approximately 100 mg in size.

U.S. Pat. No. 5,800,832 and U.S. Pat. No. 6,159,498 (Tapolsky, et al.), and U.S. Patent Publication Nos. 20030194420 and 20050013845 disclose a water soluble, biodegradable drug delivery device, e.g., a bilayer film disk having an adhesive layer and a backing layer, both water-soluble, which adheres to mucosal surfaces.

U.S. Pat. No. 6,252,981 (Zhang et al.) discloses oral mucosal drug delivery as an alternative method of systemic drug delivery formulation and method for oral transmucosal delivery of a pharmaceutical. The invention provides a drug formulation comprising a solid pharmaceutical agent in solid solution with a dissolution agent in solid form, yielding a solid solution. The formulation can be used with a variety of oral transmucosal delivery dosage forms, such as a tablet, lozenge, lozenge on a stick, chewing gum, and buccal or mucosal patch. See, also Zhang et al, *Clin Pharmacokinet.* 2002; 41(9):661-80.

Although various oral mucosal drug delivery systems have been described, there remains a need for improved formulations for use in an oral transmucosal dosage form that allows for sustained drug delivery of the dosage form, and the ability to manipulate and control the drug dissolution kinetics. The present invention addresses this problem.

BRIEF SUMMARY OF THE INVENTION

The present invention provides compositions and methods comprising drug dosage forms comprising a formulation of the invention, as described in detail herein below.

In one embodiment, the invention provides a bioadhesive drug formulation for oral transmucosal administration to a subject, which comprises a non-ordered mixture of a predetermined amount of a pharmaceutically active agent and a bioadhesive material, where the bioadhesive material provides for adherence to the oral mucosa of the subject.

In another embodiment, the invention provides a bioadhesive drug formulation for oral transmucosal administration to a subject, which comprises a predetermined amount of a pharmaceutically active agent and a bioadhesive material, where dissolution of the drug formulation is independent of pH.

The formulation may have one or more of the following characteristics: the formulation may further comprise stearic acid; the formulation may become a hydrogel upon contact with an aqueous fluid; the formulation may be provided as an eroding dosage form which upon contact with an aqueous fluid, erodes without formation of a hydrogel; the formulation may be provided as a dosage form where upon contact with an aqueous fluid, the dosage form disintegrates and forms a film and/or the formulation may be provided as a dosage form, the dissolution of which is independent of pH.

The invention further provides dosage forms comprising such formulations wherein the dosage form is a lozenge, a pill, a tablet, a capsule, a membrane, a strip, a liquid, a patch, a film, a gel or a spray.

The predetermined amount of a pharmaceutically active agent in the formulation may be 10 µg, 15 µg, 25 µg, 50 µg, 100 µg, 500 µg, 1 mg, 2 mg, 3 mg, 4 mg, 5 mg, 6 mg, 7 mg, 8 mg, 9 mg or 10 mg and the pharmaceutically active agent may be characterized by a Log P of from about 0.006 to about 3.382.

The pharmaceutically active agent may be effective to treat anxiety (e.g., pre-procedural anxiety), pain (e.g., acute or post-operative pain), nausea, vomiting or asthma.

The invention further provides a formulation for treatment of pain where the pharmaceutically active drug is selected from fentanyl, sufentanil, alfentanil, lofentanil, carfentanil, remifentanil, trefentanil, and mirfentanil.

A drug formulation of the invention for treatment of pain may comprise: (1) from about 1 mcg to about 50 mcg of sufentanil; or (2) from about 10 mcg to about 500 mcg of fentanyl.

The invention further provides a formulation for treatment of pre-procedural anxiety where the formulation comprises at least one benzodiazepine or non-benzodiazepine anxiolytic or sedative agent in combination with at least one opioid or non-opioid analgesic.

Such a drug formulation of the invention for treatment of pre-procedural anxiety may comprise a benzodiazepine agent selected from triazolam, alprazolam, midazolam, temazepam, estazolam, flurazepam, nitrazepam, bromazepam, halazepam and clonazepam or similar benzodiazepine; or a non-benzodiazepine agent selected from zolpidem tartrate, zaleplon, and eszopiclone.

A drug formulation of the invention for treatment of pre-procedural anxiety may further comprise at least one opioid selected from fentanyl, sufentanil, alfentanil, lofentanil, carfentanil, remifentanil, trefentanil, and mirfentanil.

The invention further provides a formulation for treatment of nausea or vomiting where the formulation comprises a pharmaceutically active drug selected from ondansetron, dolasetron and granisetron, droperidol, prochlorperazine, metaclopramide and cannabinoid receptor agonists.

The invention further provides a formulation for treatment of asthma where the formulation comprises a pharmaceutically active drug selected from short-acting beta2-adrenergic receptor agonists, such as salbutamol, terbutaline, albuterol, fenoterol and orciprenaline.

The invention also provides methods of a treating a symptomatic medical condition in a subject by administering a formulation of the invention.

The invention further provides disposable single dose applicators (SDAs) for dispensing a drug dosage form comprising a formulation of the invention and methods of using the same, including placement of a dosage form on an oral mucosal membrane of a subject, with or without a device.

BRIEF DESCRIPTION OF THE FIGURES

FIG. 17 provides an illustration of a multiple dose applicator where a plurality of single dose applicators are stored prior to use.

FIGS. 18A-C provide an illustration of additional single dose applicator and multiple dose applicator embodiments.

FIGS. 19A-B provides an illustrations of two stages of use of one embodiment of a single dose applicator.

DETAILED DESCRIPTION

Figure 1:
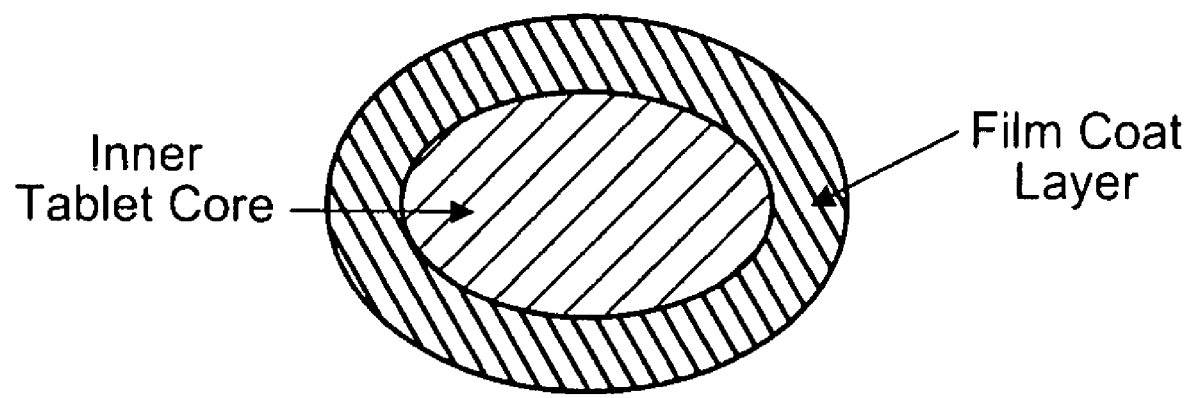
FIG. 1 is a graphic depiction of the design of a thin-film coated hydrogel bioadhesive tablet.

The invention is based on formulations for oral transmucosal drug delivery that adhere to the oral mucosa during the period of delivery such that the majority of drug is delivered across the oral mucosa.

The present invention provides novel formulations, including drug formulations which may be used to make dosage forms that can be self-administered, provide a therapeutic effect and a predictable and safe pharmacokinetic profile for a large number of pharmaceutically active agents (drugs).

Exemplary formulations of the invention comprise a drug for treatment of pain (acute, intermittent or breakthrough pain), anxiety, nausea or vomiting, migraine, asthma, panic disorder, status epilepticus, acute alcohol withdrawal, insomnia, depression, sedation, acute bipolar mania, schizophrenia.

The following disclosure describes the formulations which constitute the invention. The invention is not limited to the specific formulations and methodology or medical conditions described herein, as such may, of course, vary. It is also to be understood that the terminology used herein is for the purpose of describing particular embodiments only, and is not intended to limit the scope of the present invention.

It must be noted that as used herein and in the appended claims, the singular forms "a", "and", and "the" include plural references unless the context clearly dictates otherwise. Thus, for example, reference to "a drug formulation" includes a plurality of such formulations and reference to "a drug delivery device" includes systems comprising drug formulations and devices for containment, storage and delivery of such formulations.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

I. DEFINITIONS

The term "formulation" or "drug formulation" or "dosage form" as used herein refers to a composition containing at least one therapeutic agent or medication for delivery to a subject. The dosage form comprises a given "formulation" or "drug formulation" and may be administered to a patient in the form of a lozenge, pill, tablet, capsule, membrane, strip, liquid, patch, film, gel, spray or other form.

The terms "drug", "medication", "pharmacologically active agent" and the like are used interchangeably herein and generally refer to any substance that alters the physiology of an animal. A dosage from comprising a formulation of the invention may be used to deliver any drug that may be administered by the oral transmucosal route. The term "drug" as used herein with reference to a formulation of the invention means any "drug", "active agent", "active", "medication" or "therapeutically active agent" that can be effectively administered by the oral transmucosal route.

The term "drug" as applied to analgesia includes sufentanil or a sufentanil congener, such as alfentanil, fentanyl, lofentanil, carfentanil, remifentanil, trefentanil, or mirfentanil, as well as formulations comprising one or more therapeutic compounds. Use of "drug" or the phrase "sufentanil or a congener" is not meant to be limiting to use of, or formulations comprising, only one of these selected opioid compounds. Furthermore, reference to sufentanil alone or to a selected sufentanil congener alone, e.g., reference to "fentanyl", is understood to be only exemplary of the drugs suitable for delivery according to the methods of the invention, and is not meant to be limiting in any way.

The term "drug" may be used interchangeably herein with the term "therapeutic agent" or "medication". It will be understood that a "drug" formulation of the invention may include more than one therapeutic agent, wherein exemplary combinations of therapeutic agents include a combination of two or more opioid analogues, such as sufentanil plus an opioid such as fentanyl, alfentanil, lofentanil, carfentanil, remifentanil, trefentanil, or mirfentanil, or any other drug that might be administered in combination.

The term "active agent" or "active" may be used interchangeably herein with the term "drug" and is used herein to refer to any therapeutically active agent.

The term "congener" as used herein refers to one of many variants or configurations of a common chemical structure.

The term "subject" includes any subject, generally a mammal (e.g., human, canine, feline, equine, bovine, ungulate etc.), in which treatment for a disorder, such as management of pain or anesthetization, is desired.

The term "mucosal membrane" refers generally to any of the mucus-coated biological membranes in the body. Absorption through the mucosal membranes of the oral cavity is of particular interest. Thus, buccal, sublingual, gingival and palatal absorption are specifically contemplated by the present invention. In a preferred embodiment, the penetration enhancers of the present invention are used to improve absorption through those oral tissues which most resemble the skin in their cellular structure, i.e. the gingiva and palate.

The term "transmucosal" delivery of a drug and the like is meant to encompass all forms of delivery across or through a mucosal membrane. In particular, "oral transmucosal" delivery of a drug includes delivery across any tissue of the mouth, pharynx, larynx, trachea, or upper gastrointestinal tract, particularly including the sublingual, gingival and palatal mucosal tissues.

The terms "oral dosage form", "oral transmucosal dosage form" and "dissolvable dosage form" may be used interchangeably herein and refer to a dosage form for use in practicing the present invention, which comprises a drug formulation as described herein. The oral dosage form is typically a "sublingual dosage form", but in some cases other oral transmucosal routes may be employed. The invention relies upon such oral dosage forms to provide sustained delivery of drugs across the oral mucosa; by controlling the formulation design immediate, intermediate and sustained release of drugs can be achieved, as described below. The dosage form is a substantially homogeneous composition which comprises active ingredients and one or more of mucoadhesives (also referred to herein as "bioadhesives") that provide for adherence to the mucosa of the mouth of a patient, binders for binding the excipients in a single tablet, one or more hydrogel-forming excipients, one or more bulking agents, one or more lubricants, as well as other excipients and factors that affect dissolution time or drug stability. The dissolvable drug formulations of the invention are neither effervescent nor do they comprise an essentially water-free, ordered mixture of microparticles of drug adhered to the surface of carrier particles, where the carrier particles are substantially larger than the microparticles of drug. In one aspect, the present invention provides small-volume oral transmucosal drug delivery dosage forms. The small-volume drug delivery dosage forms or nanotabs may have a volume of from about 0.1 to about 50, from about 0.5 to about 10.0, from 1.0 to about 25 or from about 3.0 to about 15.0 microliters, e.g., 5.0 microliters; a thickness of from about 0.25 to about 10.0 mm; from about 0.5 to about 3.0 mm, e.g., about 1.0 mm; and a diameter of from about 1.0 to about 30.0 mm, from about 1.0 to about 10.0 mm, e.g., about 2.5 mm.

The term "non-ordered particulate mixture" or "non-ordered mixture" is used herein with reference to a formulation of the invention where the mixture is not ordered with respect to the pharmaceutically active agent and the bioadhesive material or bioadhesion promoting agent, or other formulation components. In addition, the term is used herein with reference to any formulation prepared by a process that involves dry mixing wherein drug particles are not uniformly distributed over the surface of larger carrier particles. Such 'non-ordered' mixing may involve dry mixing of particles in a non-ordered fashion, where there is no requirement with respect to the order of addition/mixing of specific excipients with the drug, bioadhesive material or bioadhesion promoting agent and/or disintegrants. Further in the non-ordered mixing process, there is no limitation on the size of the drug particles. The drug particles may be larger than 25 um. In addition, a "non-ordered mixture" includes any mixing processes in which the primary carrier particles do not incorporate a disintegrant within. Finally the "non-ordered mixture" may be prepared by any 'wet mixing' processes, i.e. processes in which a solvent or non-solvent is added during the mixing process or any mixing process in which the drug is added in a solution or suspension form.

The term "oral transmucosal drug delivery" as used herein refers to delivery substantially via the oral transmucosal route and not via swallowing followed by GI absorption. This includes delivery via the buccal, sublingual or gum transmucosal areas. The formulations of the current invention are designed to provide for a drug dissolution rate that allows for maximal delivery via the oral mucosa, and also provides sustained delivery rates across the oral mucosa via placement of the dosage form within transmucosal cavity.

As used herein, "sublingual", means literally "under the tongue" and refers to a method of administering substances via the mouth in such a way that the substances are rapidly absorbed via the blood vessels under the tongue rather than via the digestive tract. Among the various transmucosal sites, the mucosa of the sublingual cavity is found to be the most convenient and easily accessible site for the delivery of therapeutic agents for both local and systemic delivery as sustained release dosage forms because it of its abundant vascularization. Direct access to the systemic circulation through the internal jugular vein bypasses the hepatic first pass metabolism leading to high bioavailability. Further, owing to the highly vascularized nature of the sublingual mucosal membrane and the reduced number of epithelial cell layers compared to other mucosal membranes, absorption of therapeutic substances occurs rapidly, thus allowing for direct access to the systemic circulation and thus enable quick onset of action while avoiding complications of oral administration.

As used herein, the term "hydrogel-forming preparation", means a solid formulation largely devoid of water which upon contact with bodily fluids, and in particular those in the oral mucosa, is capable of absorbing water in such a way that it forms a hydrated gel in situ. The formation of the gel follows unique disintegration (or erosion) kinetics with sustained release of the drug over time, which occurs primarily by diffusion. Additionally, the term "hydrogel-forming preparation" describes a solid formulation largely devoid of water which upon contact with bodily fluids, and in particular those in the oral cavity, transforms into a film that releases the drug. Such films increase the surface area available for drug release and absorption thus enabling faster absorption of the drug.

The term "disintegration" is used interchangeably herein with the term "erosion" and means the physical process by which a tablet breaks down and pertains to the physical integrity of the tablet alone. This can occur in a number of different ways including breaking into smaller pieces and ultimately, fine and large particulates or, alternatively, eroding from the outside in until the tablet has disappeared.

The term "dissolution" as used herein means the process by which the active ingredient is dissolved from the tablet in the presence of a solvent, in vitro, or physiological fluids in vivo, e.g., saliva, irrespective of the mechanism of release, diffusion, erosion or combined erosion and diffusion.

The term "bioadhesion" as used herein refers to the process of adhesion of the dosage forms to a biological surface more in general, including mucosal membranes.

The expression "mucoadhesion" is used herein to refer to adhesion to mucosal membranes which are covered by mucus, such as those in the oral cavity and is used interchangeably herein with the term "bioadhesion" which refers to adhesion to any biological surface.

The term "therapeutically effective amount" means an amount of a therapeutic agent, or a rate of delivery of a therapeutic agent (e.g., amount over time), effective to facilitate a desired therapeutic effect, such as pain relief. The precise desired therapeutic effect (e.g., the degree of pain relief, and source of the pain relieved, etc.) will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

"Controlled drug delivery" refers to release or administration of a drug from a given dosage form in a controlled fashion in order to achieve the desired pharmacokinetic profile in vivo. An aspect of "controlled" drug delivery is the ability to manipulate the formulation and/or dosage form in order to establish the desired kinetics of drug release.

"Sustained drug delivery" refers to release or administration of a drug from a given dosage form in a sustained fashion in order to achieve the desired pharmacokinetic profile in vivo.

The term "$T_{max}$" as used herein means the time point of maximum observed plasma concentration.

The term "$C_{max}$" as used herein means the maximum observed plasma concentration.

The term "AUC" as used herein means "area under the curve" in a plot of concentration of drug in plasma versus time. AUC is usually given for the time interval zero to infinity, however, clearly plasma drug concentrations cannot be measured 'to infinity' for a patient so mathematical approaches are used to estimate the AUC from a limited number of concentration measurements. In a practical sense, the AUC (from zero to infinity) represents the total amount of drug absorbed by the body, irrespective of the rate of absorption. This is useful when trying to determine whether two formulations of the same dose release the same dose of drug to the body. The AUC of a transmucosal dosage form compared to that of the same dosage administered intravenously serves as the basis for a measurement of bioavailability.

The term "F" as used herein means "percent bioavailability" and represents the fraction of drug absorbed from the test article as compared to the same drug when administered intravenously. It is calculated from the $AUC_\infty$ of the test article following delivery from the intended route versus the $AUC_\infty$ for the same drug after intravenous administration. It is calculated from the equation: F (%)=$AUC_\infty$ (test article)/$AUC_\infty$ (intravenous route/article). This is an important term that establishes the relative fraction of the drug absorbed via the test route (or article) versus the maximum possible amount absorbed via the intravenous route.

The term "$T_{onset}$" as used herein means the observed "time of onset" and represents the time required for the plasma drug concentration to reach 50% of the maximum observed plasma concentration, $C_{max}$.

The term "Therapeutic Time Ratio" or "TTR" represents the average time that the drug is present at therapeutic levels, defined as time within which the drug plasma concentration is maintained above 50% of $C_{max}$ normalized by the drug's elimination half-life and it is calculated by the formula: TTR= (Time above 50% of $C_{max}$)/(Terminal intravenous elimination half-life of the drug). The last term is obtained from literature data for the drug of interest in the appropriate species.

As used herein, when a drug formulation is said to "adhere" to a surface, such as a mucosal membrane, it is meant that the formulation is in contact with said surface and is retained on the surface without the application of an external force. Adhesion is not meant to imply any particular degree of sticking or bonding, nor is it meant to imply any degree of permanency.

The term "non-occlusive" is used herein in its broadest sense to refer to not trapping or closing the skin to the atmosphere by means of a patch device, fixed reservoir, application chamber, tape, bandage, sticking plaster, or the like which remains on the skin at the site of application for a prolonged length of time.

The term "Log P" as used herein means logarithm of the ratio of concentrations of un-ionized compound between octanol and water. It is also called the "octanol-water partition coefficient" and serves as a means to identify a chemical characteristic of a given drug.

II. ORAL TRANSMUCOSAL DRUG DELIVERY DOSAGE FORMS

The present invention provides oral transmucosal drug delivery dosage forms, that produce a reduced saliva response when compared with other oral dosage forms, thus providing high absorption and sustained absorption rates of the pharmaceutically active substance across the oral mucosa, and reduced delivery to the gastrointestinal tract in addition to offering a more reproducible means of delivery.

The oral dosage form is typically a "sublingual dosage form", but in some cases other oral transmucosal routes may be employed. The invention relies upon such oral dosage forms for sustained delivery of drugs across the oral mucosa. The dosage form is a substantially homogeneous composition which comprises active ingredients and one or more mucoadhesives (also referred to herein as "bioadhesives") that provide for adhesion to the mucosa of the mouth of a patient, one or more binders that provide binding of the excipients in a single tablet, one or more hydrogel-forming excipients, one or more bulking agents, one or more lubricants, as well as other excipients and factors that modify and control the drug's dissolution time and kinetics or protect the active from degradation.

The dosage forms of the invention are adapted for oral transmucosal (for example sublingual) delivery of a drug and typically have an erosion time of from 5 seconds up to a time selected from 1 minute, 2 minutes, 3 minutes, 4 minutes, 5 minutes, 10 minutes, 15 minutes, 30 minutes, 1 hour, 2 hours, 4 hours and 8 hours or longer.

In general, at least 35%, at least 40%, at least 45%, at least 50%, at least 55%, at least 60%, at least 65%, at least 70%, at least 75%, at least 80%, at least 85%, at least 90%, at least 95%, at least 98% or at least 99% of the drug in a dosage form comprising a formulation of the invention is absorbed via the oral mucosa.

III. FORMULATIONS OF THE INVENTION

A formulation of the invention is a substantially homogeneous composition which comprises 0.01-99% weight/weight (w/w), 0.05% to 99%, 0.01% to 50% and 0.1% to 10% w/w of the active ingredient(s) (drug, medication, etc.) and one or more of mucoadhesives (also referred to herein as "bioadhesives") that provide for adhesion to the mucosa of the mouth of a patient and may or may not further comprise one or more of the following: one or more binders that provide binding of the excipients in a single tablet; one or more hydrogel-forming excipients; one or more bulking agents; one or more lubricants; one or more glidants; one or more solubilizers; one or more surfactants; one or more flavors; one or more disintegrants; one or more buffering excipients; one or more coatings; one or more sustained release modifiers; and one or more other excipients and factors that modify and control the drug's dissolution or disintegration time and kinetics or protect the active drug from degradation.

A pharmaceutical dosage form of the invention for oral transmucosal delivery may be solid or non-solid. In one preferred embodiment, the dosage from is a solid that transforms into a hydrogel following contact with saliva. In another preferred embodiment, the dosage form is a solid that transforms into a bioadhesive film upon contact with saliva.

Excipients include substances added to the formulations of the invention which are required to produce a quality product, include, but are not limited to: bulking agents, binders, surfactants, bioadhesives, lubricants, disintegrants, stabilizers, solubilizers, glidants, and additives or factors that affect dissolution or disintegration time.

Excipients are not limited to those above. Other suitable nontoxic pharmaceutically acceptable carriers for use in oral formulations can be found in Remington's Pharmaceutical Sciences, 17th Edition, 1985.

The formulations of the invention for oral transmucosal drug delivery include at least one bioadhesive (mucoadhesive) agent or a mixture of bioadhesives to promote adhesion to the oral mucosa during drug delivery. In addition, the bioadhesive agents may also be effective in controlling the dosage form erosion time and/or, the drug dissolution kinetics over time when the dosage form is wetted by saliva. In addition, some of the mucoadhesives named in this invention may also serve as binders in the formulation to provide necessary bonding to the dosage form.

Exemplary mucoadhesive or bioadhesive materials, are selected from the group consisting of natural, synthetic or biological polymers, lipids, phospholipids, and the like. Examples of natural and/or synthetic polymers include cellulosic derivatives (such as methylcellulose, carboxymethyl cellulose, hydroxyethyl cellulose, hydroxyethylmethyl cellulose, microcrystalline cellulose, etc), natural gums (such as guar gum, xanthan gum, locust bean gum, karaya gum, veegum etc), polyacrylates (such as Carbopol, polycarbophil, etc), alginates, thiol-containing polymers, polyoxyethylenes, polyethylene glycols (PEG) of all molecular weights (preferably between 1000 and 40,000 Da, of any chemistry, linear or branched), dextrans of all molecular weights (preferably between 1000 and 40,000 Da of any source), block copolymers, such as those prepared by combinations of lactic & glycolic acid (PLA, PGA, PLGA of various viscosities, molecular weights and lactic-to-glycolic acid ratios) polyethylene glycol-polypropylene glycol block copolymers of any number and combination of repeating units (such as Pluronics, Tektronix or Genapol block copolymers), combination of the above copolymers either physically or chemically linked units (for example PEG-PLA or PEG-PLGA copolymers) mixtures. Preferably the bioadhesive material is selected from the group of polyethylene glycols, polyoxyethylenes, polyacrylic acid polymers, such as Carbopols (such as Carbopol 71G, 934P, 971P 974P) and polycarbophils (such as Noveon AA-1, Noveon CA-1, Noveon CA-2), cellulose and its derivatives and most preferably it is polyethylene glycol, Carbopol, and/or a cellulosic derivative or a combination thereof.

The mucoadhesive/bioadhesive excipient is typically present at 1-50% w/w, preferably 1-40% w/w or most preferably between 2-30% w/w. A formulation of the invention may contain one or more different bioadhesives in any combination.

The formulations of the invention for oral transmucosal drug delivery also include a binder or mixture of two or more binders which facilitate binding of the excipients into a single dosage form. Exemplary binders are selected from the group consisting of cellulosic derivatives (such as methylcellulose, carboxymethyl cellulose, hydroxyethyl cellulose, hydroxyethylmethyl cellulose, etc), polyacrylates (such as Carbopol, polycarbophil, etc), Povidone (all grades), Polyox of any molecular weight or grade, irradiated or not, starch, polyvinylpyrrolidone (PVP), Avicel, and the like.

The binder is typically present at 0.5-60% w/w, preferably 1-30% w/w and most preferably 1.5-15% w/w.

In one embodiment, the formulations of the invention for oral transmucosal drug delivery also include at least one hydrogel-forming excipient. Exemplary hydrogel-forming excipients are selected from the group consisting of polyethylene glycols and other polymers having an ethylene glycol backbone, whether homopolymers or cross-linked heteropolymers, block copolymers of ethylene glycol units, such as polyethylene oxide homopolymers (such as Polyox N10/MW=100,0001 Polyox-80/MW=200,000; Polyox 1105/MW=900,000; Polyox-301/MW=4,000,000; Polyox-303/MW=7,000,000, Polyox WSR-N-60K, all of which are tradenames of Union Carbide), hydroxypropylmethylcellylose (HPMC) of all molecular weights and grades, Poloxamers (such as Lutrol F-68, Lutrol F-127, F-105 etc, all tradenames of BASF Chemicals), Genapol, polyethylene glycols (PEG, such as PEG-1500, PEG-3500, PEG-4000, PEG-6000, PEG-8000, PEG-12000, PEG-20,000, etc.), natural gums (Xanthan gum, Locust bean gum, etc) and cellulose derivatives (HC, HMC, HMPC, HPC, CP, CMC), polyacrylic acid-based polymers either as free or cross-linked and combinations thereof, biodegradable polymers such as poly lactic acids, polyglycolic acids and any combination thereof, whether a physical blend or cross-linked. In an embodiment, the hydrogel components may be cross-linked. The hydrogel-forming excipient(s) are typically present at 0.1-70% w/w, preferably 1-50% w/w or most preferably 1-30% w/w.

The formulations of the invention for oral transmucosal drug delivery may also include at least one sustained release modifier which is a substance that upon hydration of the dosage form will preferentially interact with the drug in a physical or molecular level and thus reduce the rate of its diffusion from the transmucosal dosage form. Such excipients may also reduce the rate of water uptake by the formulation and thus enable a more prolonged drug dissolution and release from the tablet. In one embodiment, such sustained release modifiers are capable of binding molecularly to the active via physical (and therefore reversible) interactions, thus increasing the effective molecular weight of the active and thus further modifying their permeation (diffusion) characteristics through the epithelial and basal membranes of the sublingual mucosa. Such binding is reversible in nature and does not involve any chemical modifications of the active, thus it does not affect in any way its pharmacological action. In another preferred embodiment, such sustained release modifiers upon hydration may form discrete structures that may spontaneously entrap the drug and thus further prolong its action. Exemplary sustained release modifiers are selected from the group consisting of lipids, phospholipids, sterols, surfactants, polymers and salts. In general, the selected excipient(s) are lipophilic and capable of naturally form complexes with hydrophobic or lipophilic drugs. The degree of association of the release modifier(s) and the drug can be varied by altering the modifier-to-drug ratio in the formulation. In addition, such interaction may be appropriately enhanced by the appropriate combination of the release modifier with the active drug in the manufacturing process. Alternatively, the sustained release modifier may be a charged polymer either synthetic or biopolymer bearing a net charge, either positive or negative, and which is capable of binding to the active via electrostatic interactions thus modifying both its diffusion through the tablet and/or the kinetics of its permeation through the mucosal surface. Similarly to the other compounds mentioned above, such interaction is reversible and does not involve permanent chemical bonds with the active.

A sustained release modifier may typically be present at 0-80% w/w, preferably 1-20% w/w, most preferably 1-10% w/w.

Such sustained release modifiers may further create pockets or microdomains dispersed throughout the swollen network of the hydrogel. These pockets can serve as reservoirs for drug compounds, as they will tend to decrease the driving force for diffusion by reducing the concentration of the drug solute in the bulk of the hydrogel. The hydrogel matrix along with the sustained release modifiers may be selected and designed such that drug release from the microdomains occurs slowly enough to enable the sustained dissolution of the drug from the dosage form.

The formulations of the invention for oral transmucosal drug delivery also include at least one filler (bulking agent). Exemplary bulking agents are selected from the group consisting of lactose USP, Starch 1500, mannitol, sorbitol, maltodextrin, malitol or other non-reducing sugars; microcrystalline cellulose (e.g., Avicel), dibasic calcium phosphate (anhydrous or dihydrate), sucrose, etc. and mixtures thereof. The filler/bulking agent is typically present at 20-95% w/w, preferably 40-80% w/w.

The formulations of the invention for oral transmucosal drug delivery may also include at least one solubilizing agent(s). Such agents are beneficial to improve the solubility of the active drug and enhance its absorption characteristics, but also facilitate handling and manufacturing. Appropriate solubilizers may include cyclodextrins, pH adjusters, salts and buffers, surfactants, fatty acids, phospholipids, metals of fatty acids etc. Exemplary surfactants are selected from the group consisting of ionic (sodium lauryl sulfate, etc), non-ionic such as polysorbates (Tween and Span surfactant series, Poloxamers, etc.), bile salts (such as sodium taurocholate, sodium taurodeoxycholate, sodium starch glycolate, sodium glycodeoxycholate, sodium glycocholate, etc), various alkyl glycosides, fatty acids, phosphatidylcholines, triglycerides, sphingolipids, glycosylated lipids, PEGylated lipids and mixtures thereof and may be present at 0.01-5% w/w. Exemplary metal salts and buffers may include at least of either organic (acetate, citrate, tartrate, etc) or inorganic (phosphate, carbonate, bicarbonate, borate, sulfate, sulfite, bisulfite, metabisulfite, chloride, etc.) salts of metals such as sodium, potassium, calcium, magnesium, etc), Further, combinations of one or more of such salts may be used to ensure adequate stabilization of the drug in the dosage form and may be present in the formulation at 0.1-20% w/w, preferably between 1-10% w/w. Exemplary pH adjusters include hydrochloric acid, acetic acid, phosphoric acid, sodium hydroxide, ammonium hydroxide and the like and may be present in the formulation between 0.1-5% w/w.

The formulations of the invention for oral transmucosal drug delivery also include at least one lubricant. Lubricants have several functions including preventing the adhesion of the tablets to the compression equipment and in some cases improving the flow of the granulation prior to compression or encapsulation. Lubricants are in most cases hydrophobic materials. Exemplary lubricants are selected from the group consisting of stearic acid and divalent cations of, such as magnesium stearate, calcium stearate, etc., talc, glycerol monostearate and the like. The lubricant is typically present at 0.01-10% w/w, preferably between 0.1-3% w/w.

The formulations of the invention for oral transmucosal drug delivery may also include at least one glidant. Glidants are substances that improve the flow characteristics of the blended or granulated material from the hopper into the feeding mechanism and ultimately, in the tablet die. Exemplary glidants are selected from the group comprising colloidal silicon dioxide, precipitated silicon dioxide, fumed silica (CAB-O-SIL M-5P, trademark of Cabot Corporation), stearowet and sterotex, silicas (such as SILOID and SILOX silicas—trademarks of Grace Davison Products, Aerosil—trademark of Degussa Pharma), higher fatty acids, the metal salts thereof, hydrogenated vegetable oils and the like. The glidant is typically present at 0.01-20% w/w, preferably between 0.1-5% w/w.

The formulation may also contain flavors or sweeteners and colorants such as aspartame, mannitol, lactose, sucrose, other artificial sweeteners; ferric oxides and FD&C lakes.

The formulation may also contain additives to help stabilize the drug substance from chemical of physical degradation. Such degradation reactions may include oxidation, hydrolysis, aggregation, deamidation, etc. Appropriate excipients that can stabilize the drug substance may include anti-oxidants, anti-hydrolytic agents, aggregation-blockers etc. Anti-oxidants may include BHT, BHA, vitamins, citric acid, EDTA, sodium bisulfate, sodium metabisulfate, thiourea, amino acids such as methionine, etc. Aggregation blockers may include surfactants, amino-acids, such as arginine, glycine, histidine, methionine etc. Additional excipients that may help protect the active against degradation are salts, pH adjusters, chelating agents and buffers in the dry or solution form. A number of salts may include all those known in the art and may be found in Remington's Pharmaceutical Sciences, 17th Edition, 1985. Exemplary pH adjusters include hydrochloric acid, acetic acid, phosphoric acid, sodium hydroxide, ammonium hydroxide and the like. Examples of such chelating agents include polylysine of different molecular weights, disodium edetate, sodium citrate, condensed sodium phosphate and the like. Examples of salts and buffers may include at least of either organic (acetate, citrate, tartrate, etc) or inorganic (phosphate, carbonate, bicarbonate, borate, sulfate, sulfite, bisulfite, metabisulfite, chloride, etc.) salts of metals such as sodium, potassium, calcium, magnesium, etc), Further, combinations of one or more of such salts may be used to ensure adequate stabilization of the drug in the dosage form. Stabilizing excipients may be present at 0.01-15% w/w in the formulation, preferably between 0.1-5% w/w.

The formulation may also contain surfactants to increase wetting of the tablet, especially if faster release kinetics are desired, which can result in faster initiation of mucoadhesion. Such surfactants are generally present from 0.01 to 3% weight percent of the composition. Exemplary surfactants are selected from the group consisting of ionic (sodium lauryl sulfate, etc), non-ionic such as polysorbates (Tween and Span surfactant series), bile salts (such as sodium taurocholate, sodium taurodeoxycholate, sodium glycodeoxycholate, sodium glycocholate, etc), various alkyl glycosides, fatty acids, phosphatidylcholines, triglycerides, sphingolipids, glycosylated lipids, PEGylated lipids and mixtures thereof.

A dosage form of the invention may additionally comprise one or more excipients that may affect both tablet disintegration kinetics and drug release from the tablet, and thus pharmacokinetics. Such disintegrants are known to those skilled in the art and may be selected from a group consisting of starch, carboxy-methycellulose type or crosslinked Polyvinyl Pyrrolidone (such as cross-povidone, PVP-XL), alginates, cellulose-based disintegrants (such as purified cellulose, methylcellulose, crosslinked sodium carboxy methylcellulose (Ac-Di-Sol) and carboxy methyl cellulose), low substituted hydroxypropyl ethers of cellulose, microcrystalline cellulose (such as Avicel), ion exchange resins (such as Ambrelite IPR 88), gums (such as agar, locust bean, karaya, Pectin and tragacanth), guar gums, gum Karaya, chitin and chitosan, Smecta, gellan gum, Isapghula Husk, Polacrillin Potassium (Tulsion[339]), gas-evolving disintegrants (such as citric acid and tartaric acid along with the sodium bicarbonate, sodium carbonate, potassium bicarbonate or calcium carbonate), sodium starch glycolate (such as Explotab and Primogel), starch DC and the likes. Addition of such additives facilitates the fast disintegration (or erosion) of the tablet into smaller pieces that erode more rapidly. An additional benefit of inclusion of such disintegrants in the formulations of the present invention, is that the smaller, drug-containing particles formed upon disintegration have, by virtue of the highly increased surface area of contact with the oral mucosa, superior bioadhesive properties. In addition, the increased surface area may further facilitate the fast release of the active substance and thus further accelerate drug absorption and attainment of the required therapeutic levels systemically. However, as described above, such disintegrants are used at a low % w/w level in the solid dosage form, typically 1-30% w/w relative to the total weight of the dosage unit, preferably 5-25% w/w.

In one aspect of the invention, the dosage forms may comprise one or more biodegradable polymers of any type useful for sustained drug release. Exemplary polymer compositions include polyanhydrides and co-polymers of lactic acid and glycolic acid, poly(dl-lactide-co-glycolide) (PLGA), poly (lactic acid) (PLA), poly(glycolic acid) (PGA), polyorthoesters, proteins, and polysaccharides.

One method of making a formulation of the invention includes the steps of weighing the drug and one or more of bioadhesives, binders, hydrogel forming excipients, bulking agents, lubricants or glidants and factors that affect dissolution time, possibly powder grinding, dry powder mixing and tableting via direct compression. Alternatively, a wet granulation process may be used. Such a method (such as high shear granulation process) involves mixing the active drug and possibly some excipients in a mixer. The binder may be added in the mix dry or dissolved in the fluid used for granulation. The granulating solution or suspension is added to the dry powders in the mixer and mixed until the desired characteristics are achieved. This usually produces granules of suitable characteristics for producing dosage forms with adequate dissolution time, content uniformity, and other physical characteristics. After the wet granulation step, the product is most often dried and/or then milled after drying to get a major percentage of the product within a desired size range. Sometimes, the product is dried after being wet-sized using a suitable device, such as an oscillating granulator or a mill. The dry granulation mix may then processed to get an acceptable size range by first screening with a sieving device, and then milling the oversized particles. In some instances, an appropriate glidant is added to improve the flow properties of the granules; suitable glidants, as described above.

A formulation of the invention may be manufactured by alternative granulation processes, all known to those skilled in the art, such as spray fluid bed granulation, extrusion and spheronization or fluid bed rotor granulation.

A bioadhesive tablet may be made using a formulation of the invention by coating a primary tablet with suitable coatings known in the art. Such coatings are meant to protect the active cores against damage (abrasion, breakage, dust formation) against influences to which the cores are exposed during transport and storage (atmospheric humidity, temperature fluctuations), and naturally these film coatings can also be colored. The sealing effect of film coats against water vapor is expressed by the water vapor permeability. Coating may be performed by one of the well known processes such as Würster coating, dry coating, film coating, fluid bed coating, pan coating, etc. Typical coating materials include polyvinyl pyrrolidone (PVP), polyvinyl pyrrolidone vinyl acetate copolymer (PVPVA), polyvinyl alcohol (PVA), polyvinyl alcohol/polyethylene glycol copolymer (PVA/PEG), gellan gum, maltodextrin, methyl cellulose, hydroxyl propyl methyl cellulose (HPMC of all grades and molecular weights), carrageenan and the like.

In one embodiment, the tablet core of the present invention may be coated with a bioadhesive material, such as those defined above, to improve bioadhesion of the tablet in the sublingual cavity. In such design, an eroding or hydrogel core is designed and coated with the appropriate bioadhesive material, thus creating a design such as that shown in FIG. 1. To further facilitate the process, appropriate disintegrants may be included in the core, as described above.

In another embodiment, the tablet core of the present invention may be coated with a moisture-resistant coating, such as a hydrophobic polymers, including celluloses, etc., to create a barrier for moisture ingress in the tablet core and thus further protect moisture-sensitive drugs. In addition, such water-resistant coat may improve the tablet behavior during manufacture by reducing its growth upon exposure to high % RH (relative humidity) environments, etc. A number of coating materials can be used to improve the moisture resistance of the tablet such as EUDRAGIT® E PO, Opadry® AMB, starch acetate and the like. Of particular interest in this application are coating materials that have very limited water uptake in <85% RH, yet rapidly absorb water at >85% RH. Such a function would facilitate wetting of the dosage form in the sublingual environment yet protect the dosage form under typical storage and moderate % RH conditions.

It will be understood that the formulation will be converted into a dosage form for delivery to a subject using procedures routinely employed by those of skill in the art. The process for preparation of the dosage form is optimized in order to achieve high dose content uniformity, which is particularly important for the potent compounds, which are generally present in mass ratios of 0.01-10% w/w.

Many methods of making dosage forms for use in the invention are known in the art and may be employed in practicing the present invention, such as direct compression, wet granulation, etc. In preparing a small tablet, such as a NanoTab®, it has been shown that erosion time and adhesion are independent of tableting force between 2-500K psi.

The dosage forms of the invention are adapted to adhere to the oral mucosa during the period of drug delivery, and until most or all of the drug has been delivered from the dosage form via the oral mucosa.

The dosage form of the current invention is further designed to enable sustained disintegration of the dosage over a time period after application in an oral mucosal cavity in vivo. The dosage forms of this invention may be designed to erode within 30 seconds—8 hours after administration. Further, they are designed to provide a range of disintegration rates, from linear to biphasic over the entire duration of the process.

In addition, the oral transmucosal dosage forms of this invention are designed to sustain and control the release (dissolution) of the drug from the dosage form after application to the oral mucosa in vivo or in vitro. The drug dissolution from these sustained-release transmucosal dosage forms can follow first or second order dissolution kinetics which can be manipulated to achieve the optimal in vivo pharmacokinetic profile and pharmacological action.

In certain embodiments of the invention, the drug dosage form is adapted to deliver 30% or more of the total amount of drug contained in a single drug dosage form to an individual via the oral mucosa. In other embodiments the percentage of the total amount of drug contained in a single drug dosage delivered transmucosally may be greater than 30-40%, 40-50%, 60-70%, 70-80%, 80-90% and preferably greater than 95%. In exemplary embodiments, at least 35%, 40%, 45%, 50%, 55%, 60%, 65%, 70%, 75%, 80%, 85%, 90%, 95%, 98% or 99%, of the total amount of drug contained in a single drug dosage form is delivered via the oral mucosa.

In certain embodiments of the invention, the drug dosage form is adapted to deliver no more than 60% of the total amount of drug contained in a single drug dosage form to an individual via the GI tract. In other embodiments the percentage delivered via the GI tract maybe lower, such that not more than 50%, 40%, 30%, 20%, 10%, 5% or 1% of the total amount of drug contained in the drug dosage form is delivered to the individual via the GI tract.

The delivery of a greater percentage (and amount) of drug via the oral mucosa and the corresponding lack of delivery via the GI tract provides a significant improvement over prior methods of drug delivery.

One preferred site for drug delivery is the sublingual area, although in certain embodiments it may be advantageous for the dosage form to be placed inside the cheek, or to adhere to the roof of the mouth or the gum.

Minimizing the saliva response produces a delivery profile that is consistent and predictable from patient to patient, which is not the case with oral lozenge formulations that produce a significant saliva response. A reduced saliva response is particularly important for drugs with poor bioavailability through the GI tract.

Sublingual delivery is preferred as the sublingual mucosa is more readily permeable to medications than other mucosal areas, such as the buccal mucosa, resulting in more rapid uptake (Shojaei A H, et al. Buccal mucosa as a route for systemic drug delivery: a review. Journal of Pharmacy and Pharmaceutical Sciences. 1:15-30, 1998).

The formulations of the invention also provide improved dissolution profiles over previous oral or oral transmucosal formulations, efficacious delivery of drug via the oral mucosa, and a consistent plasma level within the therapeutic window.

The decreased swallowing of drug and more consistent uptake of oral transmucosal dosage forms made using the formulations of the present invention result in peak plasma levels that are more consistent between individual dosages as compared to those using commercially available formulations.

Dosage forms comprising a formulation of the present invention are designed to work effectively in the unique environment of the oral cavity such that a limited amount of fluid, the relatively short period of time for drug delivery, and the pH levels within the oral cavity do not adversely affect absorption of the drug. The formulations are also designed to improve dissolution, solubility, and stability of the drug dosage form. The advantages of the present invention contribute to the ability of the drug formulation to provide higher levels of drug absorption via the oral transmucosal route and consistent dose-to-effect times, making the present formulation a significant improvement for the treatment of acute or breakthrough pain.

The formulations of the present invention are designed to avoid the high peak plasma levels of immediate-release liquid formulations by controlling both tablet disintegration (or erosion) and drug dissolution and release from the tablet to enable more consistent delivery. The formulations of the present invention may be used to provide single or individual, repetitive doses that include a defined amount of the active agent, thereby allowing the patient to accurately titrate the amount of drug delivered and to adjust the amount as appropriate in a safe and effective manner.

The advantage of the sustained-release oral transmucosal formulations described in this invention is that they can maintain the plasma drug concentration within a targeted therapeutic window for a longer duration than immediate release formulations, whether solid dosage forms or liquid-based dosage forms. The high peak plasma levels typically observed for such conventional immediate release formulations are blunted by the sustained release of the drug. In addition, a rapid decline in plasma levels is avoided since the drug will continually cross through the oral cavity into the systemic circulation during the entire process of tablet dissolution, thus providing plasma pharmacokinetics with a more stable plateau. In addition, the dosage forms described in this invention may improve treatment safety by minimizing the potentially deleterious side effects due to the reduction of the peaks and troughs in the plasma drug pharmacokinetics, which compromise treatment safety.

The oral transmucosal bioadhesive formulations of the present invention are typically designed to disintegrate (or totally erode) from within 30 seconds up to 1 minute, 2 minutes, 3 minutes, 4 minutes, 5 minutes, 10 minutes, 15 minutes, 30 minutes, 1 hour, 2 hours, 4 hours, 8 hours or longer dependent upon the patient and circumstances of drug administration as well as the intrinsic drug pharmacokinetics. It will be understood that the composition of the oral transmucosal formulations of the present invention may be adjusted to provide both a range of doses and a range of dissolution times to fit particular clinical situations.

Dissolution times for sublingual administration of the formulations of the invention will vary from 30 seconds up to 1 minute, 2 minutes, 3 minutes, 4 minutes, 5 minutes, 10 minutes, 15 minutes, 30 minutes, 1 hour, 2 hours, 4 hours, 8 hours or longer.

The oral transmucosal dosage forms of invention are designed to fit comfortably under the tongue such that the drug form disintegrates sufficiently slowly to avoid the immediate peak plasma levels followed by significant drop off seen in prior art formulations such as described in U.S. Pat. No. 6,759,059, wherein fentanyl was administered via tablets containing 400 µg of fentanyl which resulted in a peak plasma level of 2.5 ng/ml at 5 minutes post-administration, followed by an immediate drop in plasma level.

The formulations of the present invention will be provided in a number of dosage forms that vary according to the nature and amount of active ingredients while maintaining the features of the formulations of the invention for dissolution in the oral cavity such that a greater percentage of drug absorption takes place via the oral mucosal route and not the GI route.

In one aspect of the invention, when a homogeneous dosage form comprising a formulation according to the present invention is placed in the sublingual cavity, preferably under the tongue on either side of the frenulum linguae, where it adheres upon contact. While not wishing to be bound by theory, it appears that when a dosage form comprising a formulation of the invention is exposed to the moisture of the sublingual space the dosage form absorbs water, resulting in the formation of a hydrogel network. In a preferred embodiment, the hydrogel formulation is designed to form a film which is visible in the sublingual space following tablet disintegration. Upon placement on the oral mucosa, the dosage form absorbs water such that upon full hydration, it spreads across the mucosal surface, thus transforming into a bioadhesive film containing the active drug. This transformation results in a significant increase of the surface area available for drug release, thus accelerating drug diffusion and release from the dosage form.

Hydrogel formation in the dosage forms of the invention takes place in the presence of certain hydrogel-enabling excipients that have the capacity to absorb water and form gels. Such excipients include Polyox of all grades, polyethylene glycols (of all grades), PEG-based copolymers, whether homopolymers or heteropolymers (such as Poloxamer, etc), Dextran, HPMC, starch, etc, as detailed above. In addition, any combination of such excipients may favor hydrogel formation upon contact with bodily fluids. In a certain embodiment of the present invention, combinations of such hydrogel forming excipients with excipients that do not favor gel formation (i.e., don't have such a capacity to swell), e.g., certain celluloses and the like also result in formation of hydrogel structures, albeit with a lower gelling capacity.

In another aspect of the invention, dosage forms referred to herein as "eroding-type" dosage forms are provided. Such "eroding-type" dosage forms, although they may absorb significant amounts of water (depending on their composition) they do not have the same capacity of swelling and do not form gels as described for the hydrogel type formulations defined above. These "eroding-type" formulations adhere to the sublingual cavity upon contact, similar to the hydrogel formulations. However, in contrast to hydrogels, they follow a surface-erosion mechanism without prior formation of a hydrated gel. As an "eroding-type" dosage form is exposed to the moisture of the sublingual space, the surface of the tablet hydrates and erodes thereby exposing the underlying layers; as the subsequent layers become hydrated they subsequently erode and so on, thus resulting in a continuous reduction in the size of the tablet.

In a preferred embodiment, such eroding formulations are designed to form a film which is visible in the sublingual space following tablet disintegration. Upon placement on the oral mucosa, the dosage form absorbs water such that upon full hydration, it spreads across the mucosal surface, thus transforming into a bioadhesive film containing the active drug. This transformation results in a significant increase of the surface area available for drug release, thus accelerating drug diffusion and release from the dosage form. Owing to the higher contact surface area, drug absorption occurs fast, resulting in fast onset of action.

Such eroding-type dosage forms are typically characterized by a lack of inclusion of hydrogel-forming excipients and in particular Polyox (of all grades) PEG-based copolymers, whether homopolymers or heteropolymers (such as Poloxamer, etc), HPMC, etc. However, it will be understood that the percentage w/w composition of the various components of the dosage form will impact the mechanism of erosion. For example, small amounts of particular hydrogel-enabling excipients may not induce formation of a hydrogel and as such, some hydrogel-enabling excipients may be included in eroding formulations without changing their erosion-based disintegration mechanism. It is both the combination of excipients and their percent weight composition that gives a hydrogel its capacity to maintain a structural matrix upon contact with an aqueous solution. Therefore, inclusion of a hydrogel-forming excipient in a given formulation will not necessarily induce "swelling" as with the typical hydrogel formulations. Both hydrogel-forming and eroding-type formulations of the invention provide control of the drug dissolution and/or in vivo absorption kinetics to enable enhanced bioavailability and improved efficacy.

The formulations of the invention find particular utility in pediatric applications, since the comfortable and secure nature of the dosage form will allow small children to readily accept this mode of therapy and will reliably deliver drug transmucosally. Specific examples include, but are not limited to, treatment of pediatric acute pain when IV access is not available or inconvenient, treatment of pediatric asthma when the child is not able to use an inhaled route of administration effectively, treatment of nausea when a child can not or will not swallow a pill, pre-procedural sedation when a child is NPO (no oral intake allowed) or a more rapid onset is required.

Similarly, the formulations of the invention find particular utility in geriatric applications, since the comfortable and secure nature of the dosage form will allow elderly patients to readily accept this mode of therapy and will reliably deliver drug transmucosally. Specific examples include, but are not limited to, treatment of nausea when a elderly patient can't swallow a pill, acute pain when IV access is not available or inconvenient, pre-procedural sedation when a child is NPO (no oral intake allowed) or a more rapid onset is required, etc.

The formulations of the invention find further utility in veterinary applications. Specific examples include, but are not limited to, any treatment of an acute condition for which IV administration is not readily available or inconvenient, such as pain relief, anxiety/stress relief, pre-procedural sedation, etc.

IV. PHARMACEUTICALLY ACTIVE AGENTS FOR USE IN FORMULATIONS OF THE INVENTIONS

In one embodiment of the invention, a formulation of the invention finds utility in delivery of any drug which can be formulated in a dosage form comprising a bioadhesive material and a predetermined amount of a pharmaceutically active agent in an amount selected from the group consisting of 10 µg, 15 µg, 25 µg, 50 µg, 100 µg, 500 µg, 1 mg, 2 mg, 3 mg, 4 mg, 5 mg, 6 mg, 7 mg, 8 mg, 9 mg and 10 mg.

The pharmaceutically active agent in a formulation of the invention need not be micronized.

In another embodiment of the invention, a formulation of the invention finds utility in delivery of any drug which can be formulated in a dosage form having an erosion time of from 5 seconds up to a time selected from the group consisting of 1 minute, 2 minutes, 3 minutes, 4 minutes, 5 minutes, 10 minutes, 15 minutes, 30 minutes, 1 hour, 2 hours, 4 hours and 8 hours or longer.

In still another embodiment of the invention, a formulation of the invention finds utility in delivery of any drug which can be formulated in a dosage form wherein a single or repeated oral transmucosal administration to a subject results in a bioavailability of greater than 70%, 75%, 80%, 85%, 86%, 87%, 88%, 89%, 90%, 91%, 92%, 93%, 94%, 65%, 96%, 97%, 98% or 99%.

In yet another embodiment of the invention, a formulation of the invention finds utility in delivery of any drug which can be formulated in a dosage form wherein a single or repeated oral transmucosal administration to a subject results in a bioavailability with a coefficient of variation of less than 30%, less than 35% or less than 40%.

In yet another embodiment of the invention, a formulation of the invention finds utility in delivery of any drug which can be formulated in a dosage form wherein a single or repeated oral transmucosal administration to a subject results in a $C_{max}$ with a coefficient of variation of less than 30%, less than 35% or less than 40%.

In yet another embodiment of the invention, a formulation of the invention finds utility in delivery of any drug which can be formulated in a dosage form wherein a single or repeated oral transmucosal administration to a subject results in a $T_{max}$ of from about 5 minutes to about 2 hours.

In yet another embodiment of the invention, a formulation of the invention finds utility in delivery of any drug which can be formulated in a dosage form wherein a single or repeated oral transmucosal administration to a subject results in a plasma level that reaches 50% of $C_{max}$ in a time selected from about 3 minutes to 2 hours, from about 3 minutes to 30 minutes, from about 3 minutes to 20 minutes and from about 3 minutes to 10 minutes.

In yet another embodiment of the invention, a formulation of the invention finds utility in delivery of any drug which can be formulated in a dosage form wherein a single or repeated oral transmucosal administration to a subject results in a plasma half-life of from about 5 minutes and about 6 hours.

In yet another embodiment of the invention, a formulation of the invention finds utility in delivery of any drug which can be formulated in a dosage form wherein a single or repeated oral transmucosal administration to a subject results in a therapeutic time ratio of greater than 0.07 or from about 0.5 to about 2.0.

In yet another embodiment of the invention, a formulation of the invention is characterized by in vitro drug dissolution that is independent of the medium pH between pH 4.5-pH 8.0.

In yet another embodiment of the invention, a formulation of the invention can be delivered by appropriate single or multiple dose applicators or a device. Such applicators are capable of enabling accurate placement of the dosage forms of the present invention in the oral transmucosal cavity, and preferably the sublingual area.

Pharmaceutically active agents for use in a formulation of the invention are characterized by logarithm of the octanol-water partition coefficient (Log P) between 0.006 and 3.382.

Formulations of the Invention for Suppression or Mitigation of Pain

In one exemplary application, the formulations of the invention find utility in treating a subject suffering from pain that may be associated with any of a variety of identifiable or unidentifiable etiologies. The formulations of the invention find utility in suppression or mitigation of pain. The term "treatment" or "management" of pain is used here to generally describe regression, suppression, or mitigation of pain so as to make the subject more comfortable, as determined for example by pain score.

The term "acute pain" is used herein with reference to pain that is typically present for less than one month, however, in some cases pain that is present for as long as three months may also be considered to be "acute".

The term "chronic pain" is used herein with reference to pain that is typically present for longer than one month.

In one exemplary aspect, the invention relates to oral transmucosal delivery of a formulation for pain-relief comprising a drug such as an opioid or opioid agonist, for the treatment of acute or break-through pain.

The active agent in such formulations may include sufentanil, or a sufentanil congener such as alfentanil, fentanyl, lofentanil, carfentanil, remifentanil, trefentanil, or mirfentanil. One preferred embodiment utilizes sufentanil as the active agent. Another preferred embodiment utilizes fentanyl as the active agent. Other preferred embodiments utilize alfentanil, lofentanil, carfentanil, remifentanil, trefentanil, or mirfentanil as the active agent. Yet another preferred embodiment utilizes a combination of sufentanil and at least one additional agent for treatment of analgesia as the active agent.

In alternative embodiments, a formulation of the invention includes a combination of two or more opioid analogues, such as sufentanil plus an opioid such as fentanyl, alfentanil, trefentanil, mirfentanil or remifentanil. Various opioid drugs have different pharmacokinetic profiles and different interactions with mu opioid receptor splice variants and, therefore, may be used in combination to enhance the therapeutic effect. For example, sufentanil combined with fentanyl may have a rapid onset due to the sufentanil with a slower loss of analgesia due to the fentanyl.

In alternative embodiments, the drug dosage form of the invention may include at least one opioid drug and one or more other drugs wherein the other drug may be an opioid or non-opioid drug. The oral transmucosal drug delivery formulations are useful for delivery of any active drug compound and treatment of any condition wherein the active drug compound may be delivered via the oral mucosal route.

The formulation of the invention may contain a highly potent opioid, such as sufentanil, fentanyl or a sufentanil congener.

In one exemplary embodiment of the invention, each dosage form contains from about 0.25 to about 200 µg of sufentanil, in combination with one or more other therapeutic agents or drugs.

In yet another example of the invention, each dosage form contains from about 2 to about 1500 µg of fentanyl, in combination with one or more other therapeutic agents or drugs.

In some embodiments, the oral dosage formulations of the invention include an opioid antagonist, such as naloxone. In such embodiments, naloxone is provided in an appropriate concentration to inhibit activity of the opioid component of the formulation were it to be injected.

The invention finds utility in the treatment of both opioid naïve patients and opioid tolerant patients.

The term "opioid naïve patient" is used herein with reference to a patient who has not received repeated administration of an opioid substance over a period of weeks to months.

The term "opioid tolerant patient" as used herein means a physiological state characterized by a decrease in the effects of an opioid substance (e.g., analgesia, nausea or sedation) with chronic administration. An opioid substance is a drug, hormone, or other chemical substance that has analgesic, sedative and/or narcotic effects similar to those containing opium or its derivatives. If analgesic tolerance develops, the dose of opioid substance is increased to result in the same level of analgesia. This tolerance may not extend to side effects and side effects may not be well tolerated as the dose is increased.

In certain embodiments, a dosage form comprising a formulation of the invention contains at least 0.001% percent by weight of the active ingredient. Preferably, the dosage form comprises from about at least 0.005% to as much as 99.9% by weight, 0.05% to 99%, 0.01% to 50%, 0.1% to 10% of the active ingredient. In certain other embodiments, a dosage form comprising a formulation of the invention contains as much as 10 µg, 15 µg, 25 µg, 50 µg, 100 µg, 500 µg, 1 mg, 2 mg, 3 mg, 4 mg, 5 mg, 6 mg, 7 mg, 8 mg, 9 mg or 10 mg of the active ingredient or drug.

The percentage of active ingredient(s) will vary dependent upon the size of the dosage form and nature of the active ingredient(s), optimized to obtain maximal delivery via the oral mucosal route. In some aspects of the invention more than one active ingredient may be included in a single dosage form In one exemplary embodiment, a dosage form for use in the treatment of pain may comprise from about 0.25 to about 200 µg of sufentanil, from about 2.5 to about 100 µg of sufentanil, from about 2.5 to about 40 µg of sufentanil, from about 2.5 to about 15.0 µg of sufentanil, from about 2.0 to about 1500 µg of fentanyl, from about 50 to about 1500 μg of fentanyl, or from about 200 to about 1500 μg of fentanyl.

In various embodiments, the formulation of the present invention generally provides appropriate pain relief in all types of patients including children, and adults of all ages who are opioid tolerant or naïve. The invention finds utility in both the in-patient and out-patient setting.

The clinical use of sufentanil has predominantly been limited to IV administration in operating rooms or intensive care units. As further described herein, there have been a few studies on the use of liquid sufentanil preparations for low-dose intranasal administration and a case report of sublingual delivery of a liquid sufentanil preparation. In most of these studies, the smallest dosing of sufentanil in adults was 5 μg in opioid naïve patients. Intranasal bioavailability was approximately 75% of that obtained by IV, however no pharmacokinetic data has been published on the sublingual use of sufentanil.

The bioadhesive transmucosal formulations of the invention contain from about 0.25 to about 200 μg of sufentanil per dosage form for oral transmucosal delivery. As will be understood by those of skill in the art, the dose will be on the low end of the range for children and the high end of the range for adults dependent upon body mass, in particular when administered long-term to opioid-tolerant adults. Small-volume oral transmucosal drug delivery dosage forms of sufentanil have not been described.

Exemplary formulations of the invention for administration to children (pediatric patients) contain from about 0.25 to about 120 μg of sufentanil per dosage form. For example, a formulation of the invention for administration to children may contain about 0.25, 0.5, 1, 2.5, 4, 5, 6, 8, 10, 15, 20, 40, 60 or 120 μg of sufentanil for oral transmucosal delivery. It follows that for pediatric patients, an exemplary dose range is from at least about 0.02 μg/kg to about 0.5 μg/kg with a preferable range of from about 0.05 to about 0.1 μg/kg.

Exemplary formulations of the invention for administration to adults contain from about 2.5 to about 200 μg of sufentanil per dosage form. For example, a formulation of the invention for administration to adults may contain about 2.5, 3, 5, 7.5, 10, 15, 20, 40, 60, 80, 100, 120, 140, 180 or 200 μg or more of sufentanil for oral transmucosal delivery.

The dosage forms of the invention contain from about 2 to about 1500 μg of fentanyl per dosage form for oral transmucosal delivery. As will be understood by those of skill in the art, the dose will be on the low end of the range for children and the high end of the range for adults dependent upon body mass, in particular when administered long term to opioid-tolerant adults.

Exemplary dosage forms of the invention for administration to children (pediatric patients) contain from about 2 to about 900 μg of fentanyl per dosage form. For example, a dosage form of the invention for administration to children may contain about 2, 3.75, 7.5, 18.75, 30, 37.5, 45, 60, 75, 112.5, 150, 300, 450 or 900 μg of fentanyl for oral transmucosal delivery.

Exemplary dosage forms of the invention for administration to adults contain from about 18.75 to about 1500 μg of fentanyl per dosage form. For example, a dosage form of the invention for administration to adults may contain about 18.75, 22.5, 37.5, 56, 75, 112.5, 150, 300, 450, 600, 750, 900, 1050, 1350 or 1500 μg or more of fentanyl for oral transmucosal delivery.

The dosage forms of the invention contain from about 10 to about 10000 μg of alfentanil per dosage form for oral transmucosal delivery. As will be understood by those of skill in the art, the dose will be on the low end of the range for children and the high end of the range for adults dependent upon body mass, in particular when administered long term to opioid-tolerant adults.

Exemplary dosage forms of the invention for administration of alfentanil contain from about 10 μg to about 10 mg of alfentanil per dosage form. For example, a dosage form of the invention for administration may contain about 10, 25, 50, 150, 200, 300, 400, 600, 800, 1000, 2000, 3000, 5000, 7000, 9000 or 10000 μg of alfentanil for oral transmucosal delivery.

In a different exemplary embodiment, a dosage form for use in the treatment of pain may comprise from about 0.25 to about 200 μg of sufentanil in combination with from about 2 to about 1500 μg of fentanyl or from about 0.25 to about 200 μg of sufentanil or from about 2 to about 1500 μg of fentanyl in combination with one or more additional drugs.

Remifentanil, lofentanil, carfentanil, trefentanil and mirfentanil are potent fentanyl congeners which may be suitable for treatment of acute pain when delivered via a bioadhesive transmucosal formulation of this invention. The dose ranges for exemplary formulations of these congeners may include 0.25 μg to 99.9 mg for both adult and pediatric patients. These dosages may be repeated at appropriate time intervals, suitably defined for each molecule.

Alfentanil is also a potent fentanyl congener that is rapidly metabolized and may be suitable for use when delivered via a bioadhesive transmucosal formulation of this invention. Appropriate dosing of alfentanil may be in the range of 10 μg to 10 mg for both adult and pediatric patients. These dosages may be repeated at appropriate time intervals.

Patients suffering from chronic painful conditions can also have intermittent exacerbations of their pain, requiring acute use of fast-acting breakthrough opioids in addition to their use of slow-onset time-release opioids for their baseline chronic pain.

Breakthrough pain or procedural pain can be intense for short periods of time, as short as 1 or 2 minutes or as long as 30 minutes or more, therefore there would be a significant advantage in providing an opioid formulation that produced more rapid clinically effective plasma levels with a more consistent and predictable period of effect.

Opioids remain the most powerful from of analgesics, however, improved forms are needed that have minimal side effects, and can be provided in a manner in which patient use can be easily tracked by the physician.

Using current treatment methods, pain control is attempted using a number of interventions, which generally include: intravenous patient-controlled analgesia (PCA), continuous epidural infusion (CEI), other types of acute pain control, palliative care pain control, and home health patient pain control. These methods meet with varying degrees of success with respect to duration of control, ease of treatment and safety versus side effects.

The need for rapid treatment of acute pain occurs in many different clinical situations, including post-operative recuperation, rheumatoid arthritis, failed back, end-stage cancer, etc. Post-operatively, for example, patients suffer from severe pain for the first few days followed by days of mild to moderate levels of pain.

The most common analgesic used to treat moderate to severe post-operative pain is IV morphine. This is either delivered on an "as needed" basis by a nurse to the patient by an IV injection or commonly a morphine syringe is placed in a PCA pump and the patient self-administers the opioid by pressing a button which has a lock-out feature. Other opioids, such as hydromorphone and fentanyl may also be used in this manner.

Treatment of acute pain is also necessary for patients in an outpatient setting. For example, many patients suffer from chronic pain and require the use of opioids on a weekly or daily basis to treat their pain. While they may have a long-acting oral or transdermal opioid preparations to treat their chronic underlying pain levels, they often need short-acting potent opioids to treat their severe breakthrough pain levels.

Treatment of acute pain is also necessary "in the field" under highly sub-optimal conditions. Paramedics or military medics often are required to treat severe acute pain in unsterile situations, where needles used for IV or IM administration can result in unintended needle sticks, risk of infection, etc. Oral opioid tablets often take 60 minutes to provide relief which is too long for someone in severe pain.

In a number of clinical settings, there is clearly a need for a formulation that produces effective pain relief in a manner that is titratable, may be used safely and conveniently, and provides pain relief for severe breakthrough or intermittent pain over an appropriate period of time.

V. USE OF FORMULATIONS OF THE INVENTION

Oral transmucosal drug delivery is simple, non-invasive, and can be administered by the caregiver or the patient with minimal discomfort. Generally, oral transmucosal delivery of pharmaceuticals is achieved using solid dosage forms such as lozenges or tablets, however, liquids, sprays, gels, gums, powders, and films may also be used.

For certain drugs, such as those with poor bioavailability via the GI tract, such as many lipophilic opioids, oral transmucosal (OT) delivery may provide a better delivery route than GI delivery. For drugs such as opioids, oral transmucosal delivery has shorter onset time (i.e., the time from administration to therapeutic effect) than does oral GI delivery and provides significantly improved bioavailability.

Pharmacokinetics (PK) and Formulation Attributes

The uptake of medications from the bioadhesive transmucosal formulations of the present invention results in a more consistent delivery between individual dosages and individual patients as compared to that of currently available oral transmucosal dosage forms for which a large fraction of drug uptake occurs via the GI route.

Figure 11:
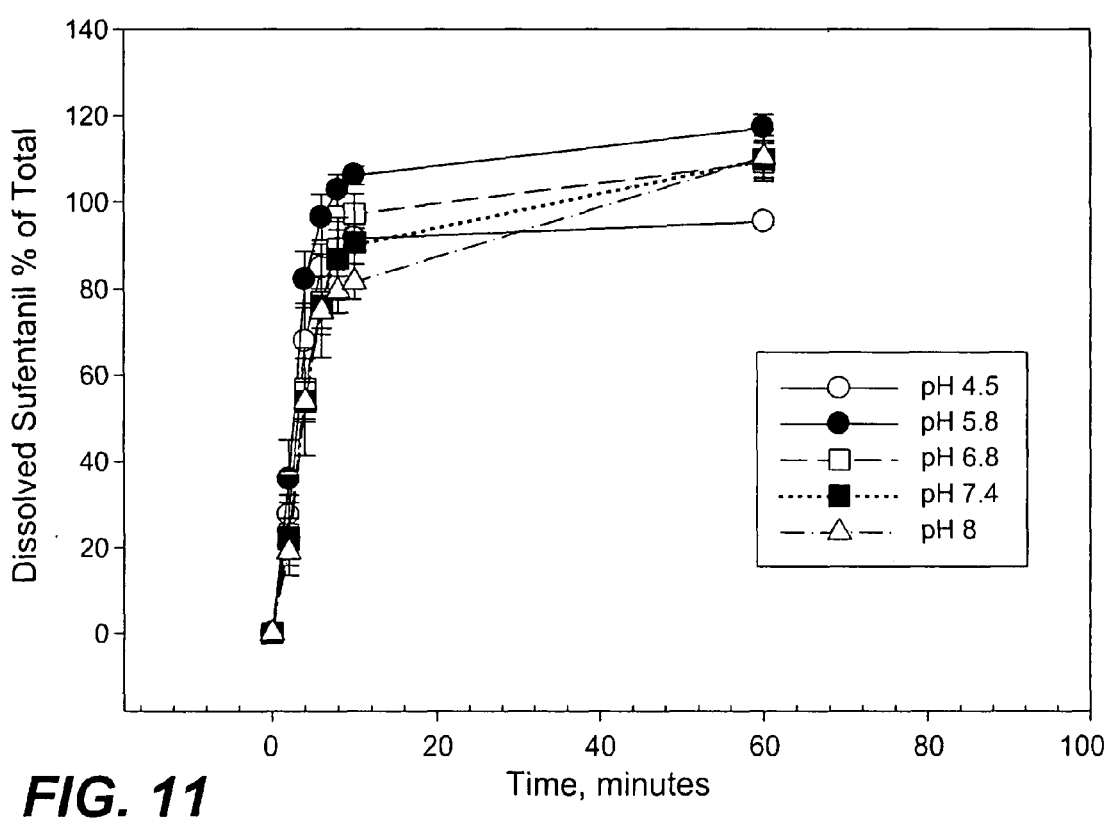
FIG. 11 is a graphic depiction of the effect of pH on dissolution kinetics of sufentanil from exemplary oral transmucosal formulations of the present invention (Formulation #A34).

The bioadhesive transmucosal formulations of the present invention are designed to work effectively in the unique environment of the oral cavity such that a limited amount of fluid, a relatively short period of time for drug dissolution, and pH levels within the oral cavity do not adversely affect absorption of the drug (FIG. 11). The dosage forms are also designed to improve dissolution, solubility, and stability of the drug. The advantages of the present invention include the ability to provide higher levels of drug absorption via oral transmucosal delivery, and consistent dose-to-effect times, making the present formulation a significant improvement for the treatment of acute or break-through pain.

The oral transmucosal formulations of the present invention are designed to avoid the high peak plasma levels of intravenous dosage forms by utilizing the oral mucosa and by controlling both tablet disintegration (or erosion) and drug dissolution and release from the tablet over time to provide a safer delivery profile. The oral transmucosal formulations of the present invention provide individual, repetitive doses that include a defined amount of the active agent, thereby allowing the patient to accurately titrate the amount of drug delivered and to adjust the amount as appropriate in a safe and effective manner.

An advantage of the bioadhesive oral transmucosal formulations described in this invention is that they exhibit consistent bioavailability and can maintain the plasma drug concentration within a targeted therapeutic window with significantly lower variability for a longer duration than currently available solid dosage forms. The high peak plasma levels typically observed for IV dosage forms are blunted following administration of a formulation of the invention, which are characterized by sustained release of the drug. In addition, a rapid decline in plasma levels is avoided since the drug is continually crossing from the oral cavity into the bloodstream during the length of time of dissolution of the tablet or longer, thus providing plasma pharmacokinetics with an extended plateau phase as compared to the IV route of administration. Further, the dosage forms of this invention may improve treatment safety by minimizing the potentially deleterious side effects due to the relative reduction of the peaks and troughs in the plasma drug pharmacokinetics, which compromise treatment safety and is typical of currently available dosage forms.

Advantages of solid sublingual formulations of the present invention over various liquid forms for either sublingual or intranasal administration of opioids include the sustained local release of the solid dosage form and the avoidance of swallowing of drug from administration of liquid dosage forms either via the nasal or the oral route. Published pharmacokinetic data on intranasal sufentanil liquid administration (15 µg) in humans demonstrates a bioavailability of 78% (Helmers et al. Comparison of intravenous and intranasal sufentanil absorption and sedation. Canadian Journal of Anaesthesia 36:494-497, 1989). Sublingual liquid sufentanil administration (5 µg) in Beagle dogs (Example 8) resulted in a bioavailability of 40%. Both these bioavailabilities are less than the 91% average that was obtained in human volunteers using sufentanil administered sublingually in the form of a NanoTab® formulation of the invention or greater than the 75% bioavailability obtained in the animal studies (Examples 7-12 below).

The oral transmucosal dosage forms of the invention are designed to fit comfortably under the tongue such that the drug-loaded dosage form disintegrates sufficiently slowly to avoid the immediate peak plasma levels followed by significant drop-off seen in prior art formulations such as described in U.S. Pat. No. 6,759,059 (Rapinyl), wherein fentanyl was administered via tablets containing 400 µg of fentanyl which resulted in a peak plasma level of 2.5 ng/mL followed by an immediate drop in plasma levels. Fentora (fentanyl buccal tablets) also suffers from a lack of a plateau phase but rather has a steep incline up to the $C_{max}$ followed by a significant drop-off in plasma levels (Fentora package insert).

The bioadhesive transmucosal formulations described in this invention are designed to form two specific kinds of delivery vehicles: hydrogels and eroding tablets. These follow two distinct disintegration and drug release mechanisms based on (i) diffusion from a hydrogel and (ii) erosion with diffusion from the eroding-type tablets. Using these fundamental designs the formulations of the invention can be designed to be fast-, intermediate- or slow-disintegrating. These system architectures are vastly different from effervescent-type tablets which are designed to break down rapidly by use of carbonate-type (or other) excipients. In addition, they are fundamentally different from dosage forms that are designed to disintegrate into large carrier particles that 'carry' the smaller (typically micron-sized) drug particles following 'ordered' mixing. The architecture of the transmucosal formulations of the present invention does not pose any requirements for specific particle sizes of drug or excipient particles, nor does require disintegration to the 'drug-coated' carrier particles to achieve the desired performance.

The bioadhesive transmucosal formulations of the present invention can be designed to manipulate and control the pharmacokinetic profile of the active drug. As such, the formulations can be adjusted to achieve fast disintegration and fast drug release and thus enable fast pharmacokinetic profiles that provide fast onset of action, while maintaining the other performance attributes of the tablet such as bioadhesion, reproducibility of action, blunted $C_{max}$, etc. Such fast-disintegrating tablets may be engineered to disintegrate from within 30 seconds up to 20 minutes and enable pharmacokinetic profiles that can vary accordingly with duration of action that can vary from 10 minutes to 1-2 hours. Alternatively, the formulations of the present invention can be adjusted to achieve 'intermediate' erosion times and drug release and thus enable 'intermediate' pharmacokinetic profiles that provide a more sustained action. Although such formulations may still provide a fast onset of action, they are mostly designed to enable the longer sustained effect while maintaining the other performance attributes of the tablet such as bioadhesion, reproducibility of action, blunted $C_{max}$, etc. Such 'intermediate'-disintegrating tablets may be engineered to disintegrate from within 30 seconds up to 30 minutes and enable pharmacokinetic profiles that can vary accordingly. Finally, the formulations of the present invention can be adjusted to achieve 'slow' disintegration times (and erosion kinetic profiles) and slow drug release and thus enable very prolonged PK that provides sustained drug action. Although such formulations may be designed to still provide a fast onset, they are mostly intended to enable the sustained drug PK and effect while maintaining the other performance attributes of the tablet such as bioadhesion, reproducibility of action, blunted $C_{max}$, etc. Such slowly-disintegrating tablets may be engineered to disintegrate from within 15 minutes to up to 8 hours and enable pharmacokinetic profiles that can vary accordingly.

Further, the bioadhesive transmucosal dosage formulations of this invention can exhibit the aforementioned performance with a number of active drugs that may span a wide range of physicochemical properties, such as water solubility, partition coefficient, etc, as further described herein.

In addition, an important advantage exhibited by the oral transmucosal formulations of the present invention is the pH-independent nature of drug dissolution for drugs over the range of pH 4.5 and 8.0. pH-independence of drug dissolution minimizes the effect of environmental conditions on drug dissolution and absorption and provides consistently high bioavailability as described above. Further, normal physiologic or disease state saliva pH is typically between 4.5-8.0. Thus, the pH-independence of drug dissolution over a pH range of 4.5-8.0 exhibited by formulations of the invention provides advantages over prior art formulations.

Finally, the performance and attributes of the bioadhesive transmucosal formulations of this invention are independent of the manufacturing process. A number of conventional, well-established and known in the art processes can be used to manufacture the formulations of the present invention (such as wet and dry granulation, direct compression, etc). without impacting the dosage form physicochemical properties or in vivo performance.

Pharmacokinetics—Animal Studies

Selected dosage forms comprising formulations of the invention were tested in a suitable animal model to evaluate the pharmacokinetics following sublingual administration and thus elucidate the properties of the formulations of the present invention. Comparisons of oral transmucosal drug delivery using formulations of the invention relative to liquid sublingual administration as well as swallowed NanoTabs® were made to evaluate their performance. The results support our claim that the bioadhesive formulations of the invention are well tolerated sublingually in dogs, result in higher bioavailability and more consistent pharmacokinetic profiles than other oral transmucosal dosage forms, including instilled liquids. Further, they demonstrate the ability of the transmucosal formulations of this invention to blunt the $C_{max}$ and modify the drug absorption profile to achieve fast, intermediate or prolonged absorption.

In order to demonstrate the broad applicability of the bioadhesive transmucosal dosage forms of this invention, formulations were prepared with three different opioids: sufentanil citrate, fentanyl citrate and alfentanil hydrochloride. These molecules, albeit members of the same opioid family of analgesics, span a wide range of log P values (between 0.006 and 3.382), as shown in Table 1A. The ability of the formulations of the current invention to similarly manipulate the in vivo pharmacokinetics of these distinct molecules in vivo demonstrates the broad applicability of the formulations of the present invention to a wide range of molecules with distinct physicochemical characteristics.

TABLE 1A

Physicochemical Properties of Selected Opioids.

| Property | Molecule | | |
| --- | --- | --- | --- |
| | Sufentanil | Fentanyl | Alfentanil |
| Molecular Weight (Da) | 387.5 | 336.5 | 416.2 |
| Solubility in water | 97 µg/mL | 200 µg/mL | 130 mg/mL |
| logP $(_{o/w})$ | 3.382 | 2.928 | 0.006 |
| $T_m$ (° C.) | 97 | 87 | 140.8 |
| pKa | 8.01 | 8.43 | 6.5 |
| Therapeutic Index | 25,000 | 300 | 1000 |

One study was carried out to compare a sublingual 5 µg sufentanil NanoTab® formulation to IV sufentanil as described more fully in Example 7 (Table 12). A total of three Beagle dogs were studied and the results of the pharmacokinetic analysis are presented in FIG. 3 and tabulated in Table 13. All tablets disintegrated in <20 min following administration in dogs. The bioavailability sufentanil from the sublingual NanoTab® formulation was 74.8±10.7 compared to IV, thus confirming the superior attributes of the formulation over other dosage forms or formulation types (effervescent, etc). The coefficient of variation for the bioavailability was low (CV=14.4%) compared to that of other commercial transmucosal dosage forms, indicating unexpectedly very reproducible and efficient delivery. Absorption from the sublingual NanoTab® formulations is fast with an average $T_{max}$ of approximately 12 minutes, while the onset of delivery occurs within 7 minutes from administration. However, in contrast to IV administration, the formulation blunts the absorption maximum by 2-3-fold compared to IV. In addition, the absorption half-life is extended significantly (3.3-fold over IV) indicating a more sustained absorption profile.

An important mathematical ratio that demonstrates the prolonged plateau phase of the measured blood plasma levels of sufentanil following administration of the transmucosal bioadhesive formulations is the Therapeutic Time Ratio, which is defined as the time spent above 50% of $C_{max}$ normalized by the known IV terminal elimination half-life of the drug:

The Therapeutic Time Ratio of the sublingual sufentanil formulation of this example is 0.28 whereas the ratio for IV sufentanil is 0.05 (using the published IV elimination half-life of sufentanil in dogs of 139 minutes). Therefore, the transmucosal formulation (#44) resulted in a 5.6-fold increased therapeutic time ratio compared to IV sufentanil, indicating that after delivery from a sublingual bioadhesive formulation of this invention, sufentanil achieves and remains within efficacious therapeutic levels for longer time compared to IV. This example highlights some of the advantages of the sublingual sufentanil formulations of this invention, which include (i) efficient and reproducible delivery (ii) fast onset of action (iii) blunted $C_{max}$ of absorption and (iv) prolonged absorption profile. These attributes suggest that the transmucosal formulations of the present invention can lead to improved drug therapeutic benefit while minimizing side effects and improving the safety of drug administration.

Another study in Beagle dogs was performed to evaluate the advantages of the sublingual-formulations over liquid administration sublingually. This study is described in detail in Example 8 (Table 14). The results (presented in Table 15 and FIG. 4) indicate that although sublingual delivery of sufentanil (5 µg) via instillation from a liquid dosage form results in rapid $T_{max}$, this method of drug administration results in very low absorption (F=40.0±32.5%) and very high variability of absorption (83.1% CV) compared to the sublingual sufentanil formulation of Example 7. This is probably due to partial oral absorption of the drug following partial swallowing of the instilled liquid. The $C_{max}$ is also highly variable with this method of drug administration, exhibiting a high coefficient of variation of 72%. The Therapeutic Time Ratio for the instilled liquid sufentanil was calculated as 0.04±0.02, which is very similar to the IV sufentanil arm. Therefore, sublingual instillation from a liquid does not provide the advantageous therapeutic plateau observed with the sublingual formulation. These findings demonstrate that the high sublingual bioavailability observed from the bioadhesive formulations claimed in this application is not intrinsic to the molecule but rather it is a direct result of the unique design of the dosage form and its formulation. The transmucosal formulation's strong adhesion to the sublingual cavity minimizes the variability in the surface area available for absorption, as is the case of a liquid solution, thus improving delivery of the molecule to the systemic circulation. In addition, owing to its unique design and small dimensions, the NanoTab® does not elicit significant saliva production, thus reducing the potential for ingestion of the released drug. Both factors contribute to the higher and more uniform drug absorption from the sublingual cavity.

In another part of the same study (presented in Example 9), the bioavailability of sufentanil following swallowing of the NanoTab® was determined in the same animal model. Since there is little to no literature data on the GI sufentanil bioavailability, it was important to evaluate the bioavailability of this route of administration to further support the observation that drug from the sublingual administration of formulations could not be swallowed and maintain a high bioavailability. As indicated by the PK analysis data in Table 15, oral absorption of sufentanil from the bioadhesive tablets results in very low drug bioavailability (F=12.2±16.3%). The low absorption leads to high variability in PK, e.g., in the amount of drug absorbed and the pharmacokinetics of absorption ($C_{max}$, $T_{max}$) as shown in Table 15 (134.2% CV). The data further demonstrate that absorption from the bioadhesive formulation of Example #7 occurred almost exclusively via sublingual rather than GI absorption in contrast to commercially available opioid transmucosal dosage forms, in which a considerable amount of the drug is delivered to the GI tract (Actiq®—75%; Fentora®—50% oral absorption). These findings support the conclusion that the bioadhesive sublingual formulations of the current invention strongly adhere in the sublingual cavity in such a manner that they don't dislodge, thus avoiding oral ingestion and avoiding the high variability of plasma levels which is typical when drug is absorbed via the GI route.

In certain embodiments, the bioadhesive transmucosal formulations of the present invention can be modified in order to manipulate and control the pharmacokinetic profile. As an example the formulations can be adjusted to achieve fast disintegration and drug release and thus enable fast pharmacokinetic profiles that enable fast onset of action, while maintaining the other performance attributes of the tablet such as bioadhesion, reproducibility of action, blunted $C_{max}$, etc. Such fast-disintegrating tablets may be engineered to disintegrate from within 30 seconds up to 20 minutes and enable pharmacokinetic profiles that can vary accordingly with duration of action that can vary from 10 minutes to 1-2 hours. Alternatively, the formulations of the present invention can be adjusted to achieve 'intermediate' erosion times (and erosion kinetic profiles) and drug release and thus enable 'intermediate' pharmacokinetic profiles that provide a more sustained action. Although such formulations may still provide a fast onset of action, they are mostly designed to enable the longer sustained effect while maintaining the other performance attributes of the tablet such as bioadhesion, reproducibility of action, blunted $C_{max}$, etc. Such 'intermediate'-disintegrating tablets may be engineered to disintegrate from within 30 seconds up to 30 minutes and enable pharmacokinetic profiles that can vary accordingly. Finally, the formulations of the present invention can be adjusted to achieve 'slow' disintegration times (and erosion kinetic profiles) and slow drug release and thus enable very prolonged pharmacokinetic profiles that provide sustained drug action. Although such formulations may be designed to still provide a fast onset, they are mostly intended to enable the sustained drug PK and effect while maintaining the other performance attributes of the tablet such as bioadhesion, reproducibility of action, blunted $C_{max}$, etc. Such slowly-disintegrating tablets may be engineered to disintegrate from within 15 minutes to up to 8 hours and enable pharmacokinetic profiles that can vary accordingly.

In addition, the pharmacokinetic profiles obtained from such bioadhesive sublingual formulations may vary depending on the dosage form design, geometry, compositions, etc. Examples of such PK profiles include ascending plasma profiles, which resemble bell-shaped curves, profiles that exhibit more than a single peak, prolonged seemingly flat PK profiles over the entire duration of action or intermediate profiles. Of particular interest are bi-phasic absorption profiles that exhibit a fast release component followed by a slow, extended release phase.

It should be noted that the bioadhesive transmucosal formulation described herein (whether the fast-, intermediate- or slow-disintegrating type) are neither effervescent nor do they disintegrate to the individual carrier particles comprising the dosage form.

To demonstrate the ability of the bioadhesive transmucosal formulations of the present invention to enable such distinct pharmacokinetic profiles, a number of formulations (#54-#58) were prepared in Example 10 representing both hydrogel- and eroding-type formulations. They were prepared with sufentanil citrate and designed to provide fast, intermediate and slow release of the drug from the dosage form. The formulations, which are described in Table 16, were prepared by direct compression, as described in Example 1, except for formulation #56, which was prepared by wet granulation, as described in Example 3 and were evaluated in a healthy conscious Beagle dog model, as described in Example 10 and Table 17.

Sufentanil Administration from Fast- and Medium-Disintegrating Formulations (#55, 54).

Figure 5:
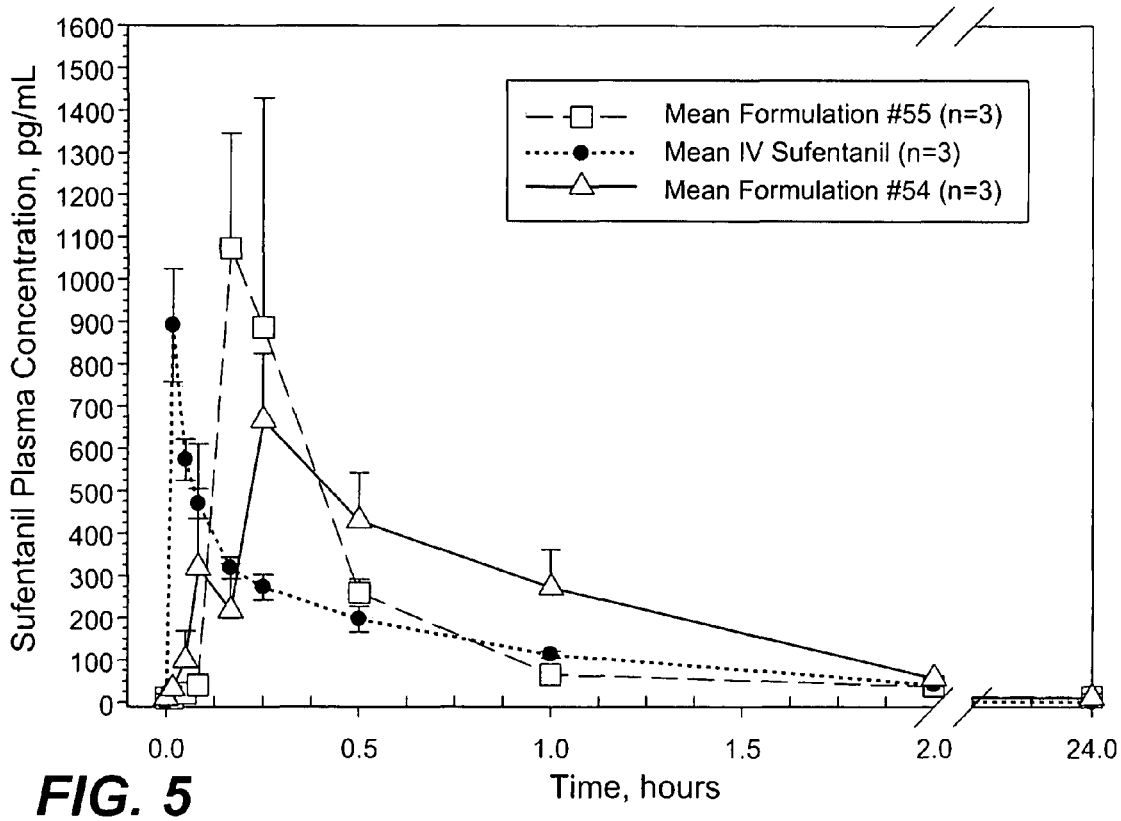
FIG. 5 is a graphic depiction of the pharmacokinetics of sufentanil following sublingual administration of fast-disintegrating NanoTab® formulation #55 (n=3) and intermediate-disintegrating NanoTab® formulation #54 (n=3), as compared to intravenous administration (n=3) in a healthy, conscious Beagle dog model. Error bars represent standard errors around the mean.

The analytical results are shown in FIG. 5 and the results of the pharmacokinetic analysis are summarized in Table 18. Tablets of formulation #55 disintegrated in <5 min following administration, while tablets of formulation #54 disintegrated in <20 minutes. Formulation #54 exhibited a fast onset of action ($T_{onset}$=7.1±0.5 min) and a relatively fast $T_{max}$ (as early as 10 minutes) following administration. In-spite of the fast onset of action, the formulation resulted in blunting of the $C_{max}$, albeit smaller than the longer-acting formulation of Example 7 and a somewhat prolonged action, as indicated by the longer plasma half-life (26.7±2.2 min) compared to IV. The performance of this formulation mirrors that of Example. 7, in that it maintains high sufentanil bioavailability (F=90.4±25.3% compared to IV) and low coefficient of variation (CV=28%) compared to other commercial transmucosal dosage forms. Finally, the TTR was increased 3-fold compared to IV, thereby confirming the very reproducible and efficient delivery enabled by the formulations of the present invention over other dosage forms or formulation types.

Formulation #54 exhibits a similarly fast (albeit slower than Formulation #55) onset of action ($T_{onset}$=9.2±4.3 min) and a relatively slower $T_{max}$ (25.0±8.7 min), while it enables increased blunting of the $C_{max}$. In addition, it displays more prolonged action, as indicated by the longer plasma half-life (49.2±22 min) compared to IV. Still, the formulation exhibits high bioavailability (F=88.2±28.9%) of sufentanil and an enhanced therapeutic benefit as indicated by the almost 6-fold increase of the TTR (0.28±0.13) compared to IV.

Sufentanil Administration from Slow-Disintegrating Formulation (#58).

The tablets of this formulation disintegrated slowly between 35 and 120 minutes following administration. This formulation exhibited a very slow onset of action ($T_{onset}$=48.0±34.1 min) and sustained sufentanil pharmacokinetics even after 8 hours post-administration (plasma half-life of 205±93.1 min). The prolonged PK resulted in significant (almost 2.4-fold) blunting of the $C_{max}$ compared to IV and a very pronounced increase (almost 22.6-fold) of the TTR (range of 8.8-36.4). These examples serve to illustrate the ability of the bioadhesive transmucosal formulations of the present invention to modify and control the drug release and pharmacokinetic action of the drug in vivo.

To further demonstrate the ability of the bioadhesive transmucosal formulations of the present invention to modify and control drug pharmacokinetics independent of the type of drug and its physicochemical properties, a number of formulations were prepared with two additional opioids, fentanyl and alfentanil.

Figure 7:
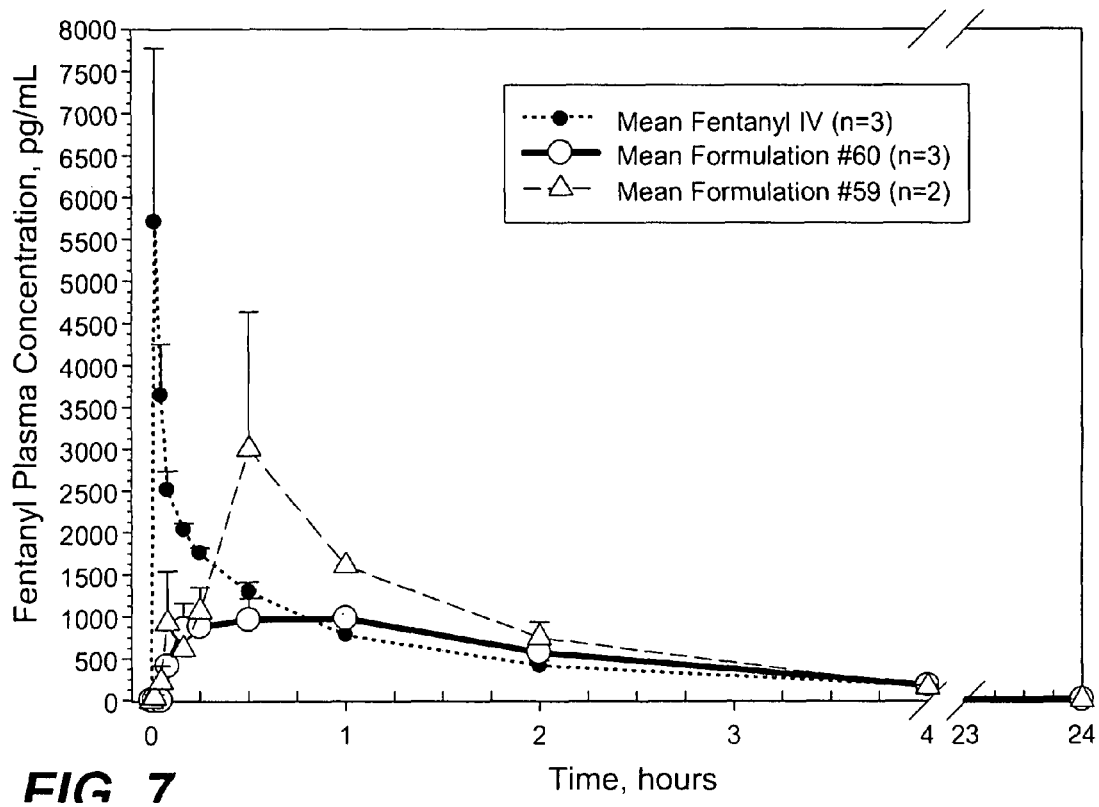
FIG. 7 is a graphic depiction of the pharmacokinetics of fentanyl following sublingual administration from medium-disintegrating NanoTab® formulations #59 (n=2) and formulation #60 (n=3), as compared to fentanyl intravenous administration (n=3) in a healthy, conscious Beagle dog model. Error bars represent standard errors around the mean.
Figure 8:
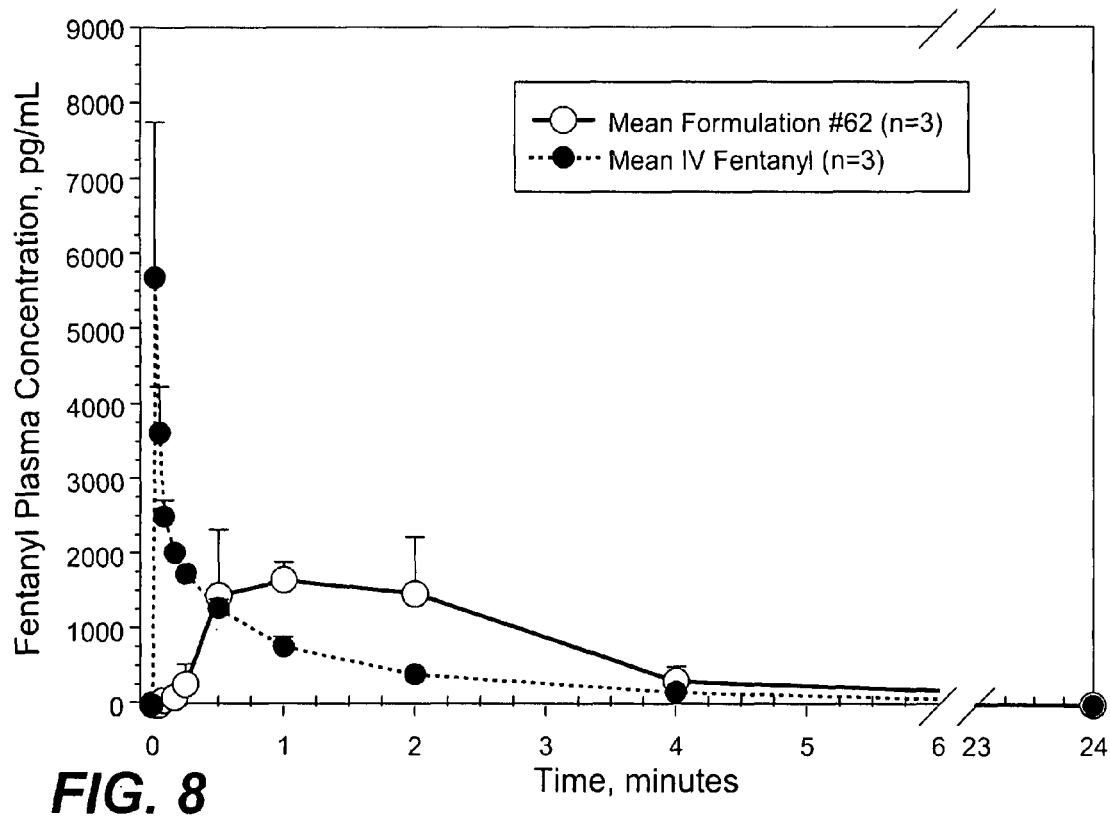
FIG. 8 is a graphic depiction of the pharmacokinetics of fentanyl following sublingual administration from slow-disintegrating NanoTab® formulation #62 (n=3) as compared to intravenous fentanyl administration (n=3) in a healthy, conscious Beagle dog model. Error bars represent standard errors around the mean.

As presented in Example 11, a number of formulations (#59-#62) were prepared (by direct compression) with fentanyl citrate representing both hydrogel- and eroding-type, designed to achieve intermediate and slow release of the drug. They were evaluated in a healthy conscious Beagle dog model, as described in Table 21. The results of the PK analysis are summarized in Table 22 and the analytical results are illustrated in FIGS. 7 and 8.

Fentanyl Administration from Medium-Disintegrating Formulations (#59, 60).

Tablets of formulation #59 disintegrated between 20 and 50 min, similarly with those of formulation #60 which disintegrated within 20 min following administration. Both formulations exhibited a relatively fast onset of action (16.2±6.8 and 9.0±2.6 min, respectively) and blunted the blunted the $C_{max}$, albeit to a different extent each: 2.4-fold for formulation #59 and 6.7-fold for formulation #60. Further, they achieved high drug bioavailability (around 95% compared to IV) and low variability of absorption (8.4 and 10.5% for formulations #59 and #60, respectively) compared to other commercial transmucosal dosage forms. In addition, both preparations significantly prolonged the drug PK. Formulation #59 exhibited a more pronounced absorption peak and exhibited a plasma half-life of 75.5±32.5 minutes (7.5-fold prolongation over IV). In contrast, formulation #60 exhibited a more prolonged absorption profile, as shown by the 12.1-fold extension of its plasma half life (121.5±19.1 minutes). This prolongation of action was also reflected in the increased TTR which increased by 6-fold for formulation #59 to 11.5-fold for formulation #60. This data confirms that fentanyl absorption via the bioadhesive transmucosal formulations of this invention results in very reproducible and efficient delivery over other dosage forms or formulation types (effervescent, etc).

Fentanyl Administration from Slow-Disintegrating Formulation (#62).

Tablets of the slowly-disintegrating formulation #62 eroded slower that the medium-disintegrating ones; erosion was completed between 35 and 65 minutes. In contrast to the medium-disintegrating formulations, the slow formulation exhibited a delayed onset of action (43.6±20.7 min), albeit maintained a very high bioavailability (F=99.0±4.4%) and very low variability (CV=4.5%) compared to other commercial transmucosal dosage forms. This formulation provides an even more prolonged absorption of fentanyl compared to the intermediate-disintegrating formulations: the plasma half-life is extended to 154.4±52.6 minutes, representing a very prolonged drug absorption profile—a nearly 15.5-fold extension for the duration of action compared to IV. This is also reflected in the nearly 4-fold reduction of the $C_{max}$ compared to IV. Finally, the Therapeutic Time Ratio is also increased compared to IV to 0.46±0.12, representing an 11.5-fold increase.

Figure 9:
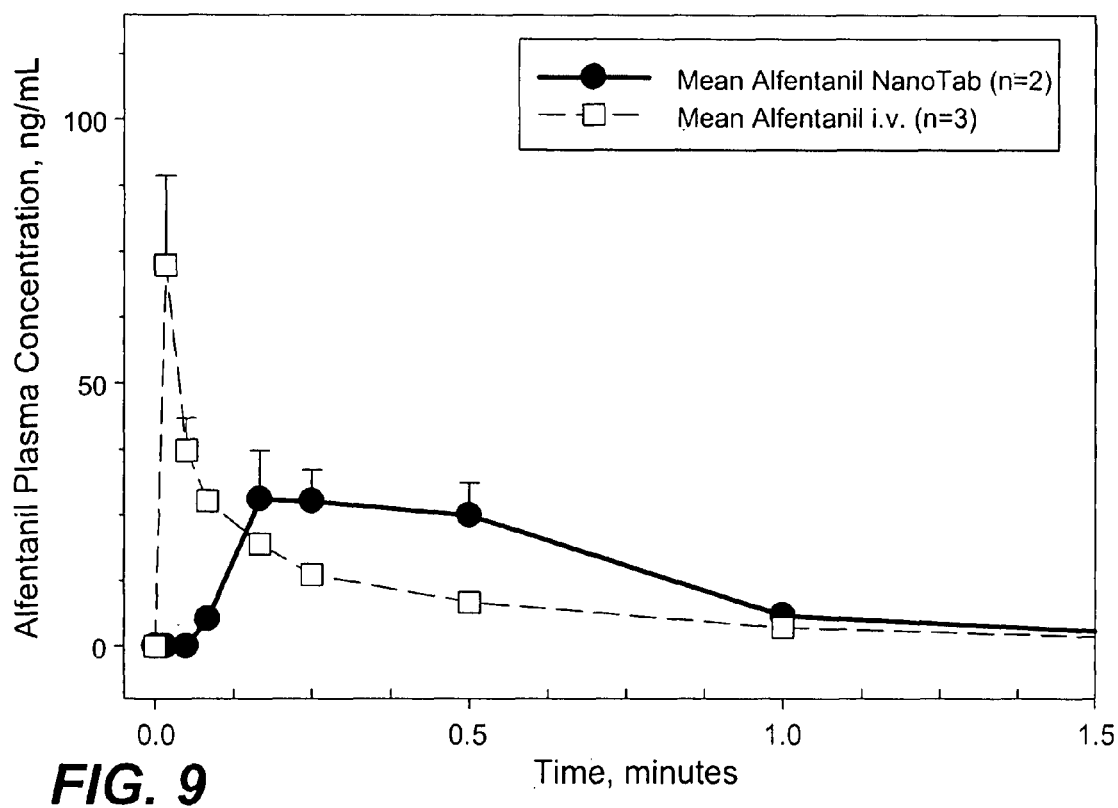
FIG. 9 is a graphic depiction of the pharmacokinetics of alfentanil following sublingual administration from Nano- Tab® formulation #63 (n=2), as compared to intravenous alfentail administration (n=3) in a healthy, conscious Beagle dog model. Error bars represent standard errors around the mean.

In addition, as shown in Example 12, a bioadhesive transmucosal formulation (#63) was prepared with alfentanil (Table 23) and was evaluated in a healthy conscious Beagle dog model, as described in Table 24. The results of the pharmacokinetic analysis are summarized in Table 25 and the PK analysis results are illustrated in FIG. 9.

Disintegration of both tablets of formulation #63 occurred within 20 minutes from administration. Alfentanil administration from the bioadhesive formulation resulted in a high bioavailability of 94% compared to IV alfentanil and a coefficient of variation of 15% for the bioavailability, 7% for $C_{max}$ and 28% for $T_{max}$. The onset of alfentanil absorption from this formulation was fast, occurring within 5 minutes from administration. The formulation blunted the absorption peak by almost 4-fold. Overall, the formulation enabled a sustained absorption profile of the drug, as indicated by the 8-to-10-fold increased plasma half-life (40.8 vs 4.4 minutes). The TTR was calculated to be 0.33, compared to 0.04 for the IV alfentanil arm of this study (calculated using a published IV elimination half-life of 104 min for alfentanil in dogs). Therefore, the alfentanil transmucosal formulation (as described in Example 12) produces an 8-fold improved TTR over the IV alfentanil arm. The high bioavailability of this formulation again supports the claim that minimal swallowing of drug occurs with use of a NanoTab®.

These examples illustrate the highly efficacious delivery of a number of molecules from the bioadhesive transmucosal formulations, which enabled high drug bioavailability with low variability for all three drugs examined. The overall drug efficacy is also portrayed in the enhanced Therapeutic Time Ratio indicating that after delivery from a sublingual formulation of the present invention, the drug achieves and remains within efficacious therapeutic levels longer than intravenous administration. In addition, the above data support the claim of the transmucosal bioadhesive formulations of the present invention are capable of controlling the drug release and enable a number of modified pharmacokinetic profiles, ranging from fast, intermediate, to slow drug absorption.

In vivo Pharmacokinetics—Human Clinical Study

The pharmacokinetics of sufentanil following sublingual administration of selected bioadhesive formulations (#46, #47 and #48 described in Table 9) were evaluated in a crossover clinical study, which is described in detail in Example 13, involving healthy, naltrexone-blocked human volunteers.

Figure 10:
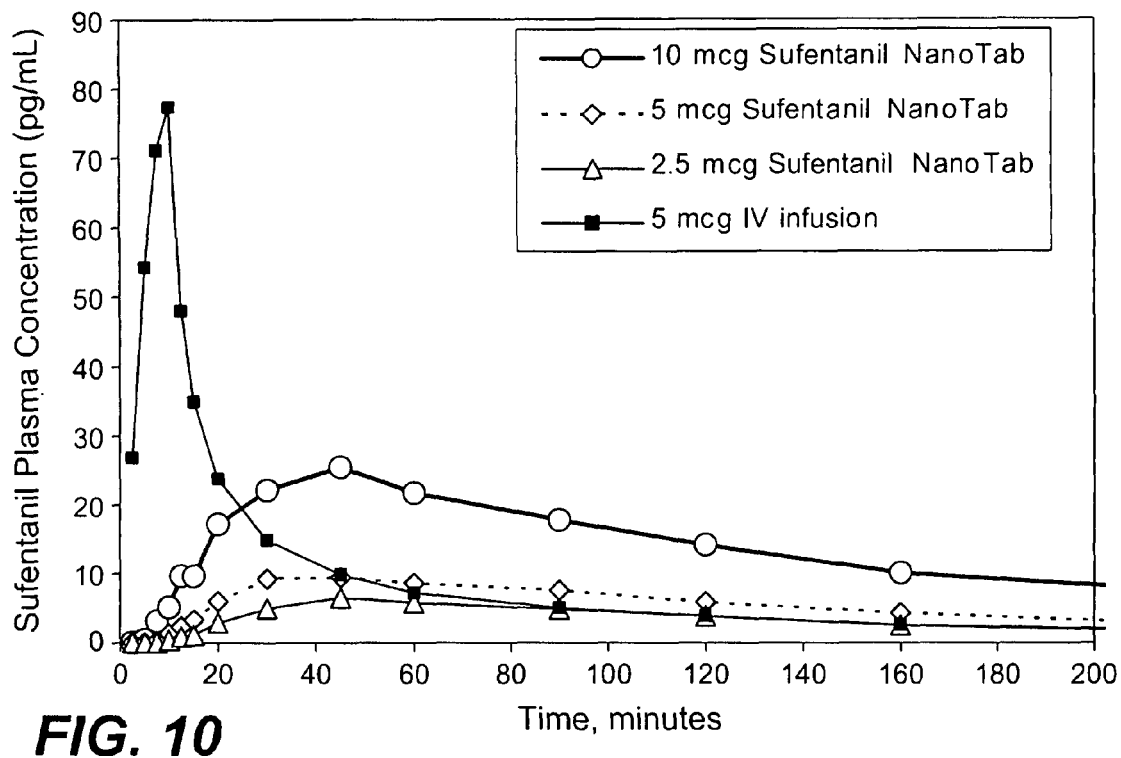
FIG. 10 is a graphic depiction of the pharmacokinetics of sufentanil following single sublingual administration (n=12) from NanoTab® formulations #46-48 as compared to intravenous administration (n=12) in healthy human volunteers.

The transmucosal formulations eroded over a period of 10-30 minutes in all subjects. In addition, there was only one incident of tablet dislodgment from the point of administration out of a total of 72 tablet administrations, indicating strong bioadhesion of the tablet to the sublingual cavity. Sublingual sufentanil administration from the bioadhesive formulations results in a remarkably consistent pharmacokinetic profile as illustrated in FIG. 10 and summarized in Table 26. The bioavailability compared to IV (for single administration) of all three dosages averaged 91%, which is far superior to that measured for commercially available fentanyl transmucosal preparations, Actiq and Fentora (47% and 65%, respectively—Fentora package insert). Although the attainment of high bioavailability could be due to a number of factors, it can be largely attributed to the reduced (if any) swallowing of the drug owing to both (i) the strong tablet bioadhesion to the sublingual mucosa that did not allow its dislodgment and subsequent swallowing, but also (ii) the lack of increased saliva production due to the small size of the dosage form. In contrast to these findings, both commercial products of Fentora and Actiq (as stated in their package inserts) claim at least 50% and 75% of the drug dose, respectively, is swallowed via saliva ingestion, thus leading to lower bioavailability than the formulations of the present invention. This finding mirrors the results of the animal studies described in Examples 7-12, which indicate very high bioavailability for the transmucosal formulations of this invention. All studies presented in this invention support the conclusion that greater than 75% of the drug is absorbed transmucosally. Therefore, less than 25% of the drug is swallowed, which is a much lower to that reported by the aforementioned commercial products.

Importantly, this high bioavailability is also linked to high reproducibility of delivery, as indicated by the low coefficients of variation for bioavailability of 24.7-34.1% for the three formulations evaluated compared to 20.1% for IV. This is much lower than that reported for Fentora (CV=45%) and Actiq (CV=41%) (Fentora package insert). Therefore the total dose delivered to the patient/subject is not only more bioavailable for the sufentanil formulations of this invention but it is more consistently the same from patient to patient. Although, as described above, this may be due to a number of factors, this is largely due to (i) the strong bioadhesion of the transmucosal dosage form in all patients, thereby reducing movement of the tablet and thereby decreasing variability of absorption and (ii) the reduced swallowing of the drug.

The sufentanil sublingual formulations are also superior in terms of consistent drug plasma levels early after administration. The $C_{max}$ obtained with formulation #48 was 27.5±7.7 pg/ml with a CV of only 28%. In contrast, the Fentora and Actiq $C_{max}$ suffers from increased variability with CVs of 41-56% and 33%, respectively (Fentora package insert).

In addition to superior bioavailability and consistency in plasma concentrations, the $T_{max}$, is a very important parameter due to the requirement for quick and consistent onset of pain relief is important in the treatment of acute pain. The $T_{max}$ for the transmucosal formulation #48 was 40.8±13.2 minutes (range 19.8-60 minutes) which is superior to the reported average $T_{max}$ for Fentora (46.8 min with a range of 20-240 min) and Actiq (90.8 min, range 35-240 min) (Fentora package insert). Therefore the bioadhesive transmucosal formulations of this invention offer markedly improved onset and consistency in the onset of analgesia over Fentora and Actiq, with a 400% decrease in the slowest onset of $T_{max}$.

Important in the treatment of acute pain, especially acute breakthrough pain, is a consistent and relatively short half-life of the drug. The plasma elimination half-life of the 10 µg sufentanil NanoTab® was 1.71±0.4 hours, which allows the drug to be titratable for various levels of pain. If the breakthrough pain event lasts longer than 1.5 hours then the patient can dose with another NanoTab®. The half-life of Actiq and Fentora are 3.2 hours and 2.63 hours, respectively, for the lowest doses. The half-lives for the higher doses increase substantially for these drugs, thereby limiting the titratability of these drugs.

Another aspect of the PK curves generated by sublingual sufentanil formulations tested in the human studies is the plateau phase, which allows for a period of consistent plasma levels, which is important for both safety and efficacy. Compared to either IV bolus administration (see Animal Studies Examples 7-12) or the 10 minute IV infusion in the human study (Example 13), the PK profile for the sufentanil formulations is clearly safer, as they result in blunting of the $C_{max}$ plasma levels. Given the ability of opioids to produce respiratory depression, avoiding these high peaks in the PK profile is advantageous.

The time spent above 50% of $C_{max}$ on average for the 12 volunteers for the 2.5, 5 and 10 µg dosage strengths was 110, 111 and 106 minutes, respectively, resulting in TTRs (for all the sufentanil formulations evaluated in the clinical study) that ranged from 0.72-0.75. These values are well in agreement with those obtained in the animal studies with sufentanil formulations (0.14-1.13). As the transmucosal formulation is modified to enable shorter or longer disintegration times, the Therapeutic Time Ratio may be modified from approximately 0.2-2.0 for sufentanil in humans.

In addition, the Therapeutic Time Ratio is a measure of how successfully short-acting drugs are formulated to produce an increase in therapeutic time and increase safety by avoiding high peak plasma $C_{max}$ concentrations. For example, as a comparison, the sufentanil IV arm of the human study demonstrated a Therapeutic Time Ratio of 0.067. This low ratio value for the IV arm, therefore, is a measure of the high peak produced by IV infusion of sufentanil and demonstrates that this formulation does not produce a significant plateau phase. In contrast, the bioadhesive transmucosal formulations evaluated in the clinical study demonstrated 10-fold higher Therapeutic Time Ratios versus IV, thereby supporting a prolonged therapeutic plateau profile for these formulations.

In summary, the data from both the clinical and animal studies clearly demonstrate the advantages of the bioadhesive transmucosal formulations of the present invention over intravenous delivery and delivery from commercially available product based on conventional technologies. The examples provided herein provide compelling data that demonstrate (i) efficient and reproducible delivery (ii) fast onset of action (iii) blunted $C_{max}$ of absorption and (iv) prolonged absorption profile. These attributes suggest that the bioadhesive formulations of the present invention can lead to improved drug therapeutic benefit while minimizing side effects and improving the safety of drug administration.

In vitro Formulation Characterization

In vitro Bioadhesion Force

As illustrated in Example 5, the transmucosal formulations of the present invention can be engineered to demonstrate varying degrees of bioadhesion. In the exemplary formulations of that example, the transmucosal formulations exhibited attachment forces to the porcine mucosa substrate that varied between 0.03 to 0.18 N/cm². The determined forces of attachment correlate directly to the magnitude of the force of adhesion in vivo. It is important to note that the specific experimental conditions (such as contact time, rinsing, etc) are expected to significantly influence the recorded detachment force; for example increased contact time will lead to increased interaction and thereby increased force of adhesion. For the determinations the 2 minutes of contact time were selected to reflect the contact time of a fast-disintegrating formulation.

The results summarized in Table 11 indicate that the strength of adhesion of the selected transmucosal formulations of Example 5 varied over a 6-fold range. However, the formulations of this invention are expected to exhibit strengths of adhesion that can extend well beyond this experimentally determined range. It is anticipated that the strength of bioadhesion of the formulations presented in this invention can be modified over the range of 0.005-1.0 N/cm² (500-10 dyn/cm²).

In Vitro Drug Dissolution Kinetics

Sufentanil citrate dissolution from formulations #46-#48 (FIG. 2) follows diffusion-type kinetics according to Higuchi's law. This type of release is the signature of hydrogel-type systems. In addition, the data is described well by the Korsmeyer & Peppas equation (Korsmeyer, R. W., Gurney, R., Doecker, E., Buri, P., Peppas, N. A., Mechanisms of solute release from hydrophilic polymers, J. Pharm. Sci. 15:25-35, 1983), with $R^2$ values between 0.96-0.98. Fitting of the dissolution curve indicated that drug release from all three systems was independent of the amount of drug loaded and that the exponent n returned fitted values of 0.566±0.109 (0.068% w/w sufentanil citrate tablet), 0.673±0.123 (0.163% w/w sufentanil citrate tablet) and 0.446±0.116 (0.273% w/w sufentanil citrate tablet). It is noted that all values of n approach 0.5, which indicates Fickian diffusion-controlled release which is somewhat influenced by the swelling of the tablet, further corroborating the hydrogel-type release from these formulations.

As also demonstrated in vivo (Examples 7-12), it is expected that the formulations of this invention can exhibit a range of dissolution profiles that may extend from a few minutes (2-4 min) to over several hours (6-8). In addition, depending on the drug physicochemical properties, the formulation composition and tablet design (such as physical dimensions, presence of coatings, number of coating layers, etc), the obtained in vitro drug dissolution profiles may exhibit a number of dissolution kinetics, such as first or second order, diffusion or erosion-based or following a mixed erosion-diffusion mechanism.

Dissolution testing of the colored dye (a surrogate for the active drug) from various formulations was performed in distilled water, using USP Apparatus 1 (Distek Technologies) and analyzed by UV-Vis detection at 590 nm for bromocresol blue. Each tablet was placed in 100 µm basket which were then placed in 100-mL glass dissolution vessels containing 5 mL of dissolution media, thermostated at 37±0.5° C. Samples were pulled at selected intervals and analyzed using an Agilent 8453 UV-Vis spectrophotometer using a 1 cm-pathlength flow-through cell with Agilent 1FS sipper system. The in-vitro dissolution of the dye for the NanoTabs was evaluated with selected formulations. The results are presented in FIG. 11.

Effect Of Effect of pH on Sufentanil Formulation Dissolution In Vitro.

Sufentanil dissolution kinetics from formulation #A34 loaded with 80 µg of sufentanil base was determined in a Type II USP dissolution apparatus suitably modified to accommodate a small volume NanoTab® containing a small amount of sufentanil. Drug release from the bioadhesive transmucosal formulations were monitored by LC/MS. The results are shown in FIG. 11. and denote the similarity of the dissolution kinetics of sufentanil from the dosage form within the pH ranges examined.

Hardness

Dosage form hardness can be determined by any pharmaceutical-grade tablet hardness equipment, such as the Vankel VK-200 Hardness Tester (manufactured by Varian Inc., Cary, N.C.). The hardness of a given dosage form typically correlates with dosage form disintegration and may range from 0.1 to 50 kiloponds (±1% full scale). In general, for hardness testing, the dosage form is placed between the "jaws" of a hardness tester. The moving jaw moves toward the stationary jaw until the dosage form is crushed and the dosage form crushing force is measured by the apparatus. Exemplary hardness measurements for a dosage form of the invention, range from about 4 to about 25 Newtons, as illustrated by the hardness values for a number of formulations shown in Table 1B.

TABLE 1B

Hardness values for a number of bioadhesive drug formulations.

| Formulation # | Hardness (N) | Weight (mg) | Bioadhesion (Mean Detachment force) (N/cm2) |
|---|---|---|---|
| A13 | 10.7 | 5.7 | |
| A14 | 5.3 | 5.1 | |
| A15 | 8.9 | 5.6 | |
| A16 | 8.9 | 5.6 | 0.139 ± 0.061 |
| A17 | 12.2 | 6 | 0.066 ± 0.007 |
| A18 | 9.6 | 6.2 | 0.158 ± 0.009 |
| A19 | 11.6 | 6.1 | 0.126 ± 0.042 |
| A20 | 12.6 | 6.2 | |
| A21 | 14 | 6.1 | |
| A22 | 14 | 6.4 | 0.086 ± 0.041 |
| A23 | 11.6 | 5.8 | |
| A24 | 9.5 | 5.61 | |
| A25 | 10.2 | 5.62 | |
| A26 | 11 | 569 | |
| A27 | 7.5 | 5.5 | |
| A28 | 10.8 | 5.5 | |
| A29 | 8.5 | 5.63 | |
| A30 | 5 | 5.4 | |
| A31 | 8.1 | 5.9 | |
| A32 | 11.6 | 5.8 | |
| A33 | 10.7 | 5.8 | 0.097 ± 0.041 |
| A34 | 13.2 | 5.61 | 0.092 ± 0.039 |
| A35 | 10-13 | 5.85 | |
| A54 | 6.9 ± 0.7 | | |
| A55 | 9.8 ± 1.3 | | |
| A56 | 12.2 ± 3.2 | | |
| A57 | 6.9 ± 2.8 | | |
| A58 | 10.5 ± 1.8 | | |
| A59 | 7.7 ± 1.7 | | |
| A60 | 13.2 ± 1.0 | | |
| A61 | 11.3 ± 1.3 | | |
| A62 | 12.2 ± 0.9 | | |

TABLE 1B-continued

Hardness values for a number of bioadhesive drug formulations.

| Formulation # | Hardness (N) | Weight (mg) | Bioadhesion (Mean Detachment force) (N/cm2) |
|---|---|---|---|
| A63 | 15.3 ± 0.9 | | |
| A64 | 14.9 ± 1.1 | | |
| A65 | 10.6 ± 1.0 | | |
| A66 | 14.7 ± 1.2 | | |
| A67 | 12.4 ± 1.0 | | |
| A68 | 12.4 ± 1.0 | | |
| A69 | 13.3 ± 1.6 | | |

Single and Multiple Dose Applicators

The invention provides disposable applicators for delivering dosage forms comprising a formulation of the invention to the oral mucosa of a patient such that application to a predetermined location for drug delivery (e.g. the mouth, sublingual space, etc.) is effected.

In one approach to the invention, a dosage form, may be delivered to the oral mucosa, using a single dose applicator. The dosage form is provided in a child-resistant drug dispensing device or packaging and delivered to the oral mucosa, for example, the sublingual cavity. Alternatively, the dosage form is administered with assistance with or without a device.

In one embodiment, a single dose applicator (SDA) is used to administer variety of drug dosage forms, including a solid tablet, a liquid capsule, a gel capsule, a liquid, a gel, a powder, a film, a strip, a ribbon, a spray, a mist, a patch, or any other suitable drug dosage form.

The single dose applicator (SDA) may contain the dosage form within, may have the drug dosage form attached or affixed to it, may have the dosage form dissolved in it, and may afford a seal against moisture, humidity, and light. The single dose applicator may be manually manipulated by a patient, healthcare provider, or other user to place the dosage form in the proper location for drug delivery.

In practicing the invention, a single- or multiple-dose applicator or drug dispensing device may be used to deliver tablets or other dosage forms into the hand, the mouth, under the tongue, or to other locations appropriate for specific drug delivery needs.

In one embodiment, a single- or multiple-dose applicator or drug dispensing device is used to deliver a dosage form to the oral mucosa, e.g., the sublingual space.

The dosage forms inside the dispensing device remain dry prior to dispensing, at which point a single dosage form is dispensed from the device into the mouth, e.g., the sublingual space, wherein a patient's saliva will wet the tablet and allow for tablet disintegration/erosion and drug dissolution.

The SDA may be provided, as a pair of forceps, a syringe, a stick or rod, a straw, a dropper, a sprayer or atomizer, or any other form suitable for the application of a single drug dosage form. After use, the SDA may be disposed of, so as to eliminate the risk of contaminating the drug dispensing device with saliva, or other contaminants.

For sublingual administration, a small volume dosage form may be administered sublingually by placement under the tongue, adjacent to the frenulum using forceps. Alternatively, a small volume dosage form may be administered sublingually by placement under the tongue, adjacent to the frenulum using a syringe, a stick or rod, a straw, a dropper, or any other form suitable for the application of a single drug dosage form, including but not limited to a SDA, as further described herein.

The dosage forms may be provided in a package that consists of molded plastic or laminate that has indentations ("blisters") into which a dosage form, is placed, referred to herein as a "blister pack". A cover, typically a laminated material or foil, is used to seal to the molded part. A blister pack may or may not have pre-formed or molded parts.

In one embodiment, the blister pack has two flexible layers that are sealed with the dosage form in between and the primary unit dose blister pack also serves as an applicator for delivering a single dosage form to the sublingual space, once the child-resistant foil is peeled back.

In yet another embodiment of the invention, a long tape or array of dosage forms sealed between a flexible blister layer and a foil or otherwise breakable layer is provided. A push rod is positioned above a dosage form, and upon actuation pushes against the blister, forcing the dosage form through the foil or breakable layer, dispensing the dosage form.

Such blister packs may be provided in a child resistant multiple dosage drug dispensing device.

FIGS. 15A-C, FIGS. 16A-F, FIGS. 18A-C and FIGS. 19A and B are schematic depictions of exemplary embodiments of a SDA of the invention.

Figure 16A:
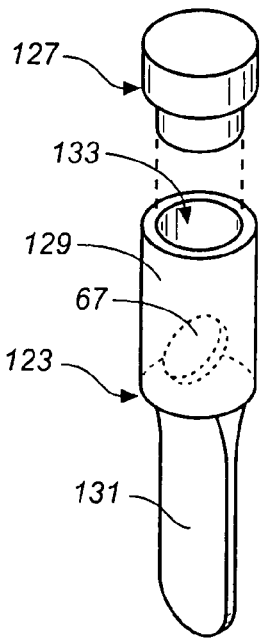
FIGS. 16A-F provide an illustration of six additional single dose applicators.
Figure 16B:
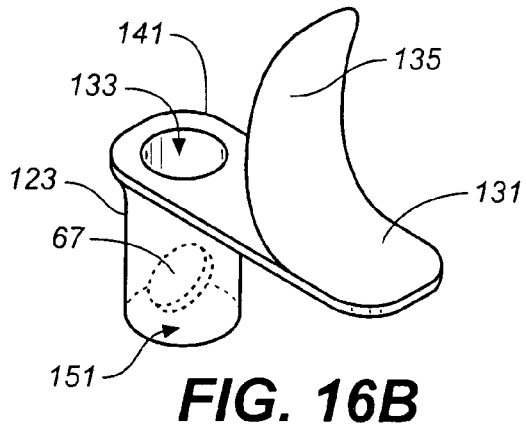
Figure 16C:
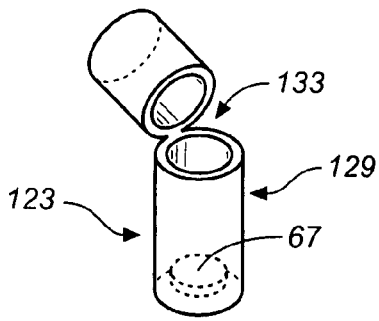
Figure 16D:
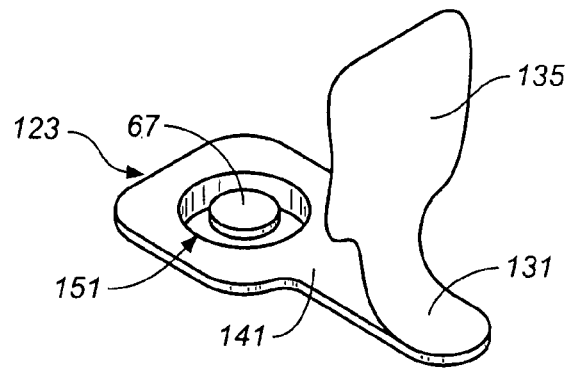

In one approach, the present invention provides disposable single dose applicators comprising a blister pack 151, which contains drug dosage forms 67 inside a housing and a handle 131, wherein a backing, such as a foil seal 135 covers the dosage form 67 and the handle 131, as shown for example in FIGS. 16B and 16D.

In one embodiment, the disposable single dose applicator, the combination of housing or tube 129 and handle 131 has the shape of a spoon.

The housing or tube 129 for the dosage form 67 is a blister pack 151 that accommodates a unit dose of a dosage form 67 for administration to a subject. The dosage form 67 is sealed in the blister pack 151 by a foil or other type of seal 135.

In some embodiments, the foil or other type of seal 135 is removed prior to administration of the dosage form 67 and the handle 131 is used to place the dosage form 67 in the appropriate location against the oral mucosa of the subject such that the dosage form 67 adheres to the oral mucosa. See, e.g., FIGS. 16B, 16D, 16E and 16F. In other embodiments, the foil or other type of seal 135 is perforated and removed prior to administration of the dosage form 67 by folding the applicator 123 at the perforation 149 prior to administration where the handle 131 is used to place the dosage form 67 in the appropriate location against the oral mucosa of a subject. See, e.g., FIGS. 19A and B. This permits the handling of only a single drug dosage form 67 at a time and prevents the other individually sealed drug dosage forms 67 from becoming exposed to saliva, humidity and the like.

The foil or other type of seal 135 of a disposable applicator 123 including handle 131 is typically made of a single piece of foil laminate, paper, plastic or other covering, i.e. an applicator tab 147 that spans the back of the housing or tube 129 alone or both the housing or tube 129 and the handle 131, effectively seals the dosage form 67 in a blister pack 151 or other container.

The handle 131 enables proper placement of the dosage form 67 without touching the dosage form 67.

A plurality of single dose applicators may be provided as a series of individual single dose applicators attached by the backing or housed in multiple dose dispenser 137.

In another embodiment, a dispensing device 11 comprises a package 141 that holds a single or multiple drug dosage forms, a distal orifice for delivery of the drug dosage form, and an internal mechanism that segregates and releases the dosage forms. See, e.g., FIG. 17. The dispensing device is typically handheld and may comprise some or all of the features set forth above for a device used to dispense non-packaged dosage forms.

Figure 14A:
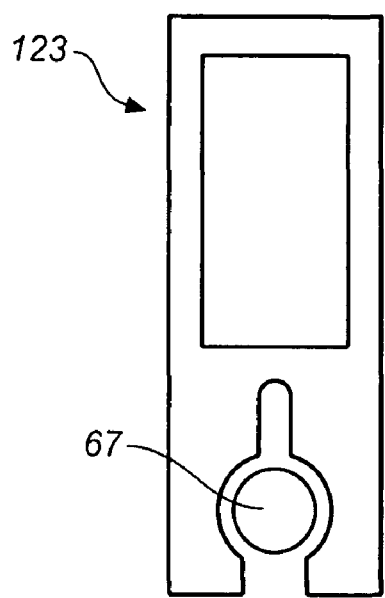
FIGS. 14A and 14B are schematic depictions of an exemplary single dose applicator.
Figure 14B:
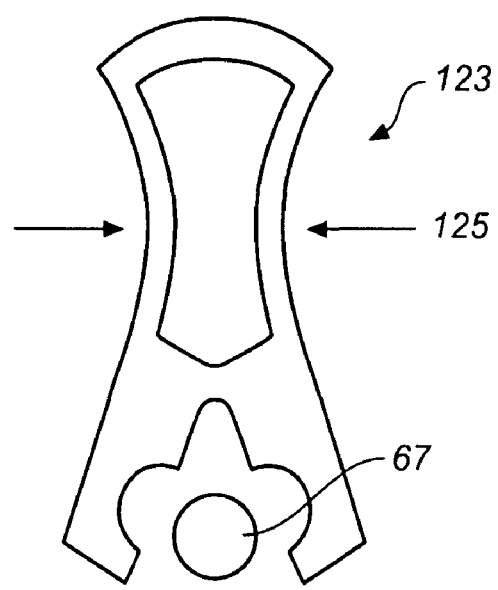

FIGS. 14A and 14B show one embodiment of a single dose applicator 123 a dispensing device for delivering drug dosage forms. The dispensing device shown in FIG. 14A depicts the single dose applicator 123 that is ready to dispense a drug dosage form 67. In one aspect of this embodiment, a user pinches the single dose applicator 125 which opens the applicator and a drug dosage form 67 is dispensed as shown in FIG. 14B.

Figure 15A:
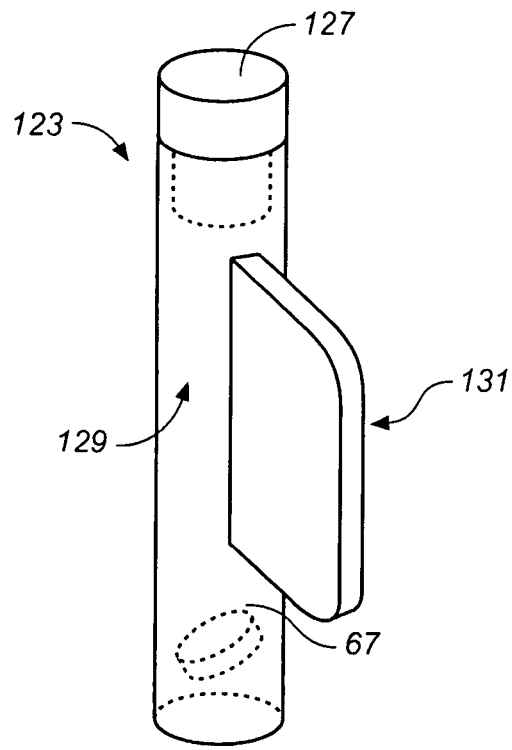
FIGS. 15A-C provide an illustration of one type of single dose applicator and use thereof in delivering a dosage form to a subject.
Figure 15B:
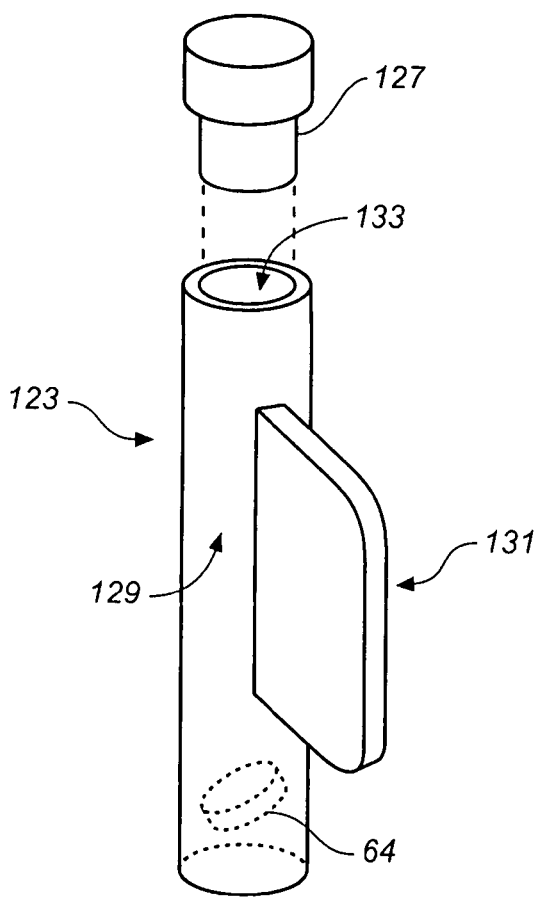
Figure 15C:
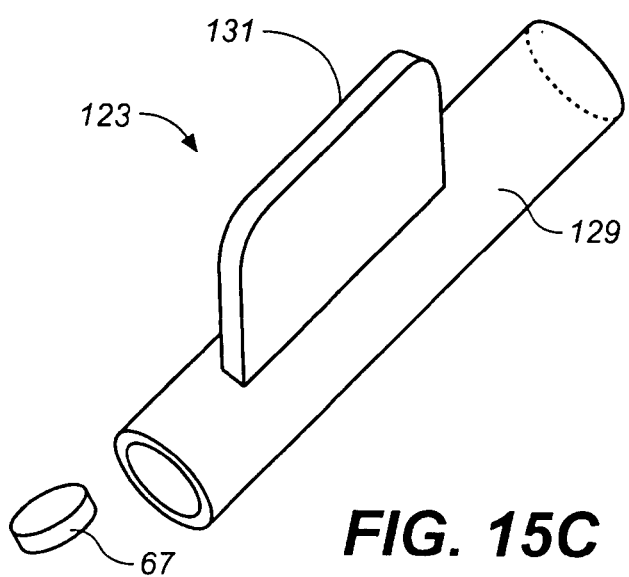

FIGS. 15A-C show an embodiment of a single dose applicator 123 that is comprised of a applicator shaped as a tube 129, a stopper seal 127, a handle 131 (e.g., an ergonomic handle), and a single dosage form 67. FIG. 15A shows the single dose applicator 123 in its sealed configuration, prior to use. FIG. 15B shows the single dose applicator 123 with its stopper seal 127 removed, forming an opening 133, and ready for use. FIG. 15C shows the single dose applicator 123 tilted so as to dispense the dosage form 67 on the oral mucosa, e.g., in the sublingual space.

Figure 16E:
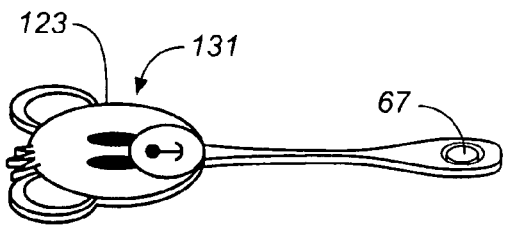
Figure 16F:
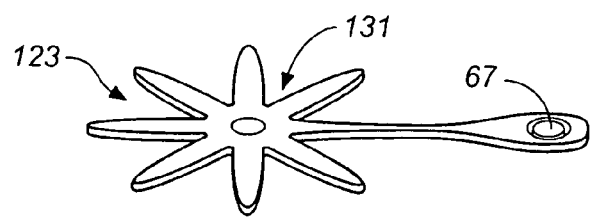

FIGS. 16A-F show several alternate embodiments of the single dose applicator 123. In all of these figures the applicator seal 127 is broken and the applicator is tilted so as to drop the drug dosage form 67 adjacent an oral mucosal membrane in the mouth of a subject, e.g., under the tongue for sublingual dosage form placement. FIG. 16A shows a tube like applicator 129 with a handle 131 located axially under the tube 129. FIG. 16B shows an applicator formed as a thermoform or blister package 151 with a foil seal 135 that is peeled so as to open the applicator package 141 prior to placing the dosage form 67. FIG. 16C shows an applicator that is a tube 129 which is broken to break the seal prior to dosage form 67 placement. FIG. 16D shows a blister pack tube 151 type dosage form package 141 with a handle 131 such that after the seal 135 is peeled back the blister pack 151 can be held and tilted to place the drug dosage form 67, on an oral mucosal membrane. FIGS. 16E and 16F show blister pack 151 type packaging with a handle 131 shaped like a flower or an animal, respectively, to be used for single dose applicator 123 designed for pediatric use. Other single dose applicator shapes could include cartoon characters, animals, super-heroes or other appropriate shapes for pediatric applications.

FIG. 18A shows a flat rigid applicator 123 with a dosage form 67 adhered to one end, for example, by means of a rapidly dissolving ingestible adhesive material such that when the applicator end with the dosage form is placed under the tongue, the adhesive dissolves, the dosage form 67 is placed on an oral mucosal membrane, such as in the sublingual space, and the applicator can be removed. FIG. 18B shows an applicator 123 made from a water permeable material, impregnated with drug, forming a material and dosage from matrix. When the impregnated end of this applicator 123 is placed under in the mouth on an oral mucosal membrane, the moisture in the saliva dissolves the drug and delivers it transmucosally. FIG. 18C shows dissolving film dosage forms 145 and a dosage form package with a plurality of dissolving film dosage forms 143 within it. The dissolving film dosage form 143 is removed from the package 141 and placed on an oral mucosal membrane, e.g., in the sublingual space where it dissolves and delivers the drug transmucosally.

FIGS. 19A-B provides an illustrations of two stages of use of one embodiment of a single dose applicator 123. FIG. 19A shows the applicator 123 in its configuration prior to use, with two applicator tabs 147, two perforations 149, and a blister pack 151 containing a dosage form 67. In order to administer the dosage form 67, the two applicator tabs 147 are bent downward at the perforations 149, forming a handle 131, and the seal 135 is peeled back to reveal the blister pack 151 and allow the dosage form 67 to be dropped on an oral mucosal membrane, e.g., in the sublingual space.

In another embodiment, a drug dispensing device of the invention may contain a plurality of SDA's, in a cartridge or individually packaged, and may dispense a single SDA containing a single drug dosage form for use by the patient, healthcare provider, or user. The drug dispensing device may dispense single SDA's in the same way and with the same features as would be advantageous for the dispensing of single drug dosage forms described in the invention.

In yet another embodiment the multiple dose applicator 137 is a device which comprises one or more drug dosage forms 67 or single dose applicators 123, a portable power means, like a battery, a printed circuit board, a data connectivity means, and a user interface. In this embodiment the drug dispensing device may include the ability to perform one or more of the following functions: record drug dosage dispensing history, check user identification by means of fingerprint identification, RFID, voice recognition, etc., allow the dosage history to be transferred to another device, computer or network, and/or provide a lockout period between dose dispenses.

FIG. 17 is a schematic depiction of an exemplary multiple dose applicator 137 for delivering dispensing drug dosage forms 67, each individually packaged in a single dose applicator 123.

Figure 12:
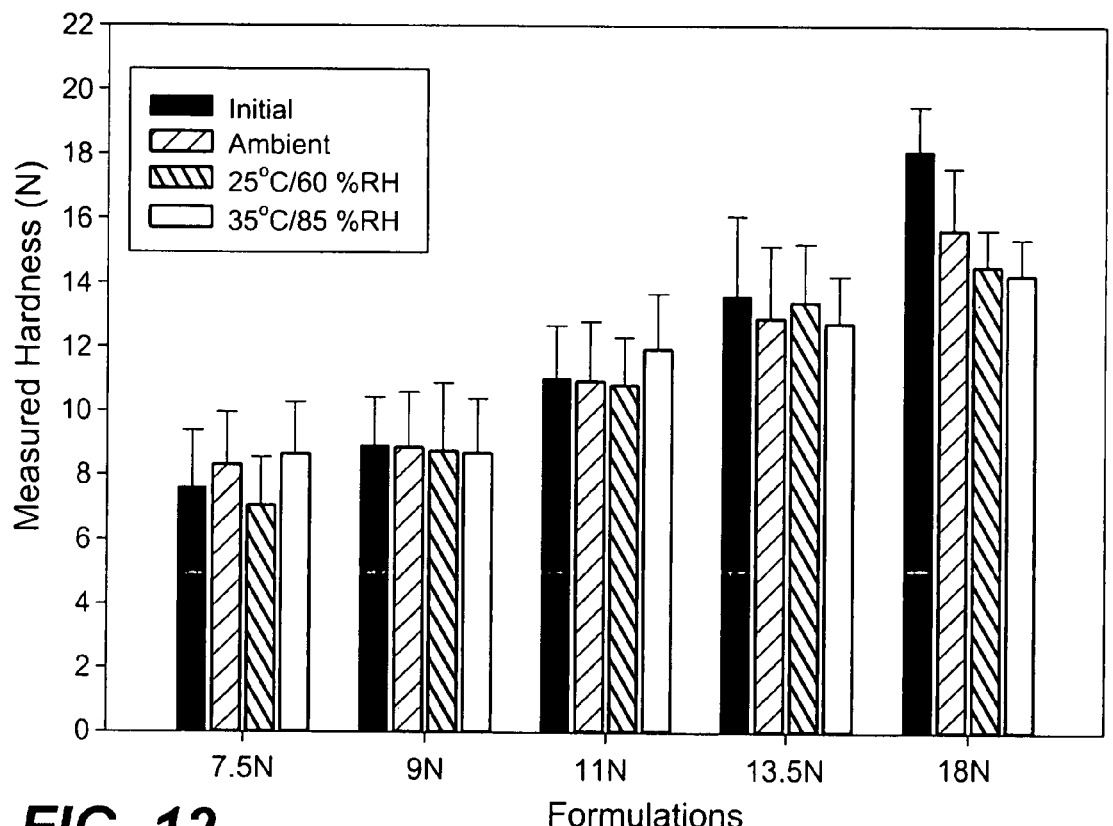
FIG. 12 is a graphic depiction of measured hardness (Newtons; "N") for formulations designated "7.5N", "9N", "11N", "13.5N" and "18N" at an initial time point, at ambient temperature, at 25° C. and 60% relative humidity (RH) or 35° C. and 85% relative humidity.
Figure 13:
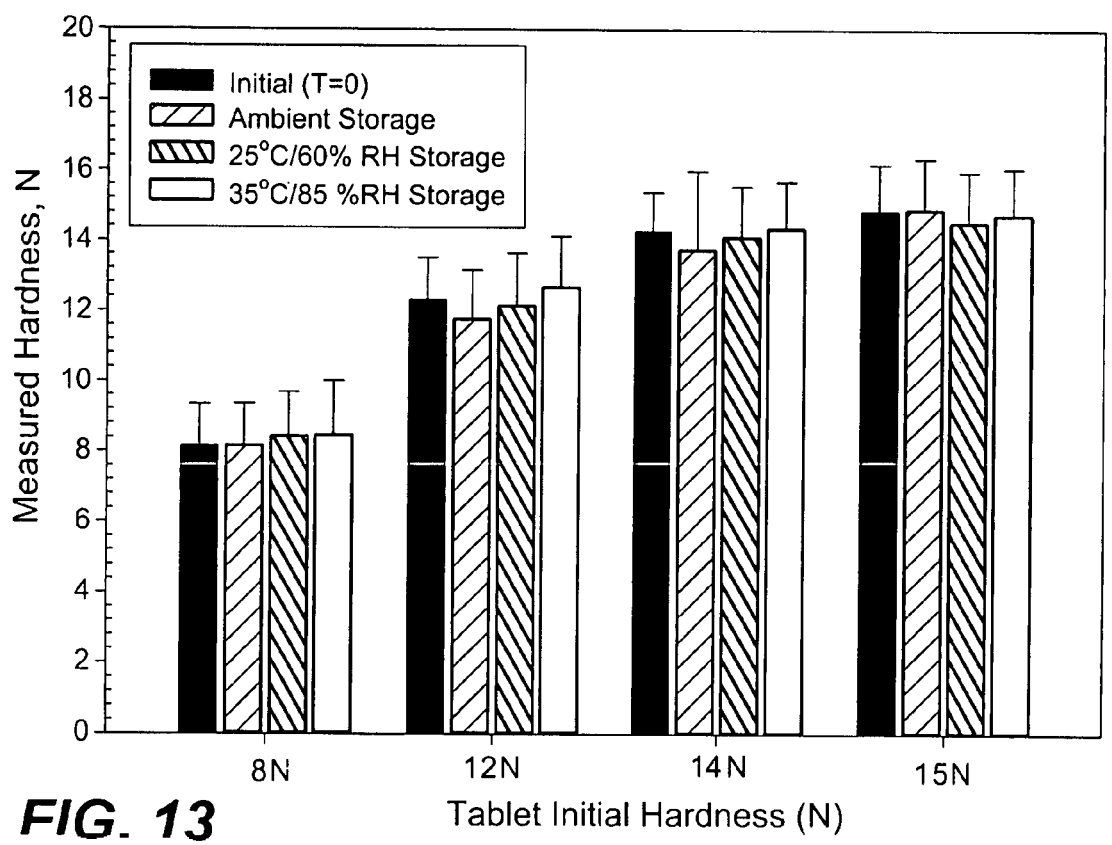
FIG. 13 is a graphic depiction of the effect of measured hardness (Newtons; "N") for formulations designated "8N", "12N", "14N" and "15N" at an initial time point, at ambient temperature, at 25° C. and 60% relative humidity (RH) or 35° C. and 85% relative humidity.

In one aspect, the invention provides drug formulations having a hardness of from about 4 to about 24 Newtons which can be administered to a patient using a device. Exemplary hardness values for formulations of the invention are shown in FIGS. 12 and 13. Sufficient hardness for delivery using a device is particularly relevant to fragile dosage forms, such as small volume tablets or NanoTabs®.

All publications referred to herein are incorporated herein by reference in their entirety for the purpose of describing and disclosing the compositions and methodologies which are described in the publications which might be used in connection with the presently described invention. The publications discussed herein are provided solely for their disclosure prior to the filing date of the present application. Nothing herein is to be construed as an admission that the invention is not entitled to antedate such a disclosure by virtue of prior invention.

EXAMPLES

The following examples are offered to illustrate, but not to limit the claimed invention. Unless noted, the total mass of all tablets made below is 5.5 mg. Further, all tablets prepared with active drug substances whether by direct compression or by wet granulation exhibited high content uniformity, as defined by the USP Pharmacopoeia with % RSD<10%.

Example 1

Exemplary Eroding Formulations Prepared by Direct Compression

For purposes of illustration, a number of exemplary eroding placebo formulations prepared by the method of direct compression are provided below in Tables 1-4. For each of the formulations, all excipients were weighed, ground with a mortar and pestle for 1-2 minutes manually mixed; the formulation included a small amount of a colorant (aluminum blue lake) as a surrogate for the active drug substance. 5.5-8.0 mg aliquots of the dry blend were weighed, loaded in a specially constructed load cell and were compressed in a Carver press at 5-20K psi. to form a dosage form. Exemplary formulations prepared using this methodology are provided in Tables 2-5 below as % w/w compositions of the excipients, wherein Tables 6 and 7 provide exemplary hydrogel formulations.

TABLE 2

Exemplary Eroding Formulations prepared by Direct Compression

| Ingredient | #1 | #2 | #3 | #4 | #5 | #6 | #7 |
|---|---|---|---|---|---|---|---|
| | | | | Composition, % w/w | | | |
| Aluminum blue lake (dye) | 0.10 | 0.10 | 0.10 | 0.10 | 0.10 | 0.10 | 0.10 |
| Mannitol | 60.00 | 60.00 | 60.00 | 60.00 | 60.00 | 60.00 | 60.00 |
| Carbopol 934 | | | | 10.00 | | | |
| Carbopol 974 | 10.00 | 10.00 | 10.00 | | 10.00 | 10.00 | 10.00 |
| HPMC-2910 | | 13.90 | | | 5.00 | | |
| PEG 8000 | 28.90 | 15.00 | 15.00 | 15.00 | 23.90 | 23.90 | 23.90 |
| PVP K90 | | | 13.90 | | | 5.00 | |
| CMC | | | | 13.90 | | | 5.00 |
| Mg Stearate | 1.00 | 1.00 | 1.00 | 1.00 | 1.00 | 1.00 | 1.00 |
| Total | 100 | 100 | 100 | 100 | 100 | 100 | 100 |

TABLE 3

Exemplary Eroding Formulations prepared by Direct Compression

| Ingredient | #8 | #9 | #10 | #11 | #12 |
|---|---|---|---|---|---|
| | | | Composition, % w/w | | |
| Aluminum blue lake (dye) | 0.10 | 0.10 | 0.10 | 0.10 | 0.10 |
| Mannitol | 63.90 | 55.00 | 60.00 | 60.00 | 57.50 |
| Dibasic Calcium Phosphate | | | | 28.90 | |
| Carbopol 934 | 20.00 | 15.00 | 10.00 | 10.00 | 12.50 |
| HPMC-2910 | | | | | |
| PEG 8000 | 15.00 | 28.90 | 28.90 | | 28.90 |
| Mg Stearate | 1.00 | 1.00 | 1.00 | 1.00 | 1.00 |
| Total | 100 | 100 | 100 | 100 | 100 |

TABLE 5

Exemplary Eroding Formulations prepared by Direct Compression

| Ingredient | #22 | #23 | #24 | #25 |
|---|---|---|---|---|
| | | Composition, % w/w | | |
| Aluminum blue lake (dye) | 0.10 | 0.10 | 0.10 | 0.10 |
| Mannitol | 50.00 | 50.00 | 50.00 | 50.00 |
| Dibasic Calcium Phosphate | | | 28.90 | 23.90 |
| Stearic Acid | | | | 23.90 |
| Carbopol 934 | 25.00 | 20.00 | 25.00 | 25.00 |
| PEG 8000 | 23.90 | | | |
| Mg Stearate | 1.00 | 1.00 | 1.00 | 1.00 |
| Total | 100 | 100 | 100 | 100 |

TABLE 4

Exemplary Eroding Formulations prepared by Direct Compression

| Ingredient | #13 | #14 | #15 | #16 | #17 | #18 | #19 | #20 | #21 |
|---|---|---|---|---|---|---|---|---|---|
| | | | | | Composition, % w/w | | | | |
| Aluminum blue lake (dye) | 0.10 | 0.10 | 0.10 | 0.10 | 0.10 | 0.10 | 0.10 | 0.10 | 0.10 |
| Mannitol | 50.00 | 50.00 | 30.00 | 20.00 | 30.00 | 30.00 | 30.00 | 30.00 | 30.00 |
| Cholesterol | | | | | | | | | |
| Dibasic Calcium Phosphate | | | 38.90 | 30.00 | 38.90 | 38.90 | 38.90 | 38.90 | 30.00 |
| Stearic Acid | | | | 18.90 | | | | | |
| Carbopol 934 | 30.00 | 40.00 | 30.00 | 30.00 | | | | | |
| Carbopol 971 | | | | | 30.00 | | | | |
| HPMC-2910 | | | | | | | | | |
| HPMC-K4 | | | | | | 30.00 | | | |
| HPMC-E3 | | | | | | | 30.00 | | |
| NA-CMC | | | | | | | | 30.00 | |
| PEG 8000 | 18.90 | 8.90 | | | | | | | |
| Mg Stearate | 1.00 | 1.00 | 1.00 | 1.00 | 1.00 | 1.00 | 1.00 | 1.00 | 1.00 |
| Total | 100 | 100 | 100 | 100 | 100 | 100 | 100 | 100 | 100 |

Example 2

Exemplary Hydrogel Formulations Prepared by Direct Compression

For purposes of illustration a number of exemplary hydrogel placebo formulations prepared by the method of direct compression are provided below in Tables 6-7. For each of the formulations, all excipients were weighed, ground with a mortar and pestle for 1-2 minutes and manually mixed; the formulations included a small amount of a colorant (aluminum blue lake) as a surrogate for the active drug substance. 5.5-8.0 mg aliquots of the dry blend were weighed, loaded in a specially constructed load cell and were compressed in a Carver press at 5-20K psi. to form a dosage form. Exemplary formulations prepared by this methodology are provided in Tables 6-7 below as % w/w compositions of the excipients.

TABLE 6

Exemplary Hydrogel Formulations Prepared by Direct Compression

| Ingredient | #26 | #27 | #28 | #29 | #30 | #31 |
|---|---|---|---|---|---|---|
| | Composition, % w/w | | | | | |
| Aluminum blue lake (dye) | 0.10 | 0.10 | 0.10 | 0.10 | 0.10 | 0.10 |
| Mannitol | 58.00 | 53.00 | 63.00 | 30.00 | 40.00 | 40.00 |
| Dibasic calcium phosphate | | | | 29 | 34 | 34 |
| Stearic Acid | 5.00 | 10.00 | | | | |
| PEG 8000 | 28.90 | 28.90 | 28.90 | | | |
| Pluronic F68 | 2.00 | 2.00 | 2.00 | | | |
| Polyox 80 | 5.00 | 5.00 | 5.00 | 25 | | |
| Polyox 301 | | | | | 25 | |
| Polyox 303 | | | | | | 25 |
| PVP K90 | | | | 15 | | |
| Mg Stearate | 1.00 | 1.00 | 1.00 | 1.00 | 1.00 | 1.00 |
| Total | 100 | 100 | 100 | 100.10 | 100.10 | 100.10 |

TABLE 7

Exemplary Eroding & Hydrogel Formulations Prepared By Full Wet Granulation

| | Eroding | Hydrogel | Hydrogel | Hydrogel | Hydrogel |
|---|---|---|---|---|---|
| | Formulation # | | | | |
| | #32 | #33 | #34 | #35 | #36 |
| | Pour/spray solution | | | | |
| | Dye solution | Dye + binder solution | Water Granulation | Water | Water |
| Excipient | Low Shear | Low shear | High Shear | High Shear | High Shear |
| | Composition, % w/w | | | | |
| FDC Green (dye) | 0.07 | 0.07 | 0.07 | 0.07 | 0.07 |
| Mannitol (Pearlitol 100SD) | 60.10 | 58.00 | | | |
| Mannitol (Pearlitol 200SD) | | | 58.00 | 58.00 | |
| Mannitol (Pearlitol 160C) | | | | | 73.93 |
| PEG 8000 | 28.83 | 28.93 | 23.93 | 23.93 | 15.00 |
| PVP K90 | | | 5.00 | 5.00 | |
| Carbopol 974 | 10.00 | | | | |
| Polyox 303 | | 5.00 | 5.00 | 5.00 | 3.00 |
| Lutrol F68 | | 2.00 | 2.00 | 2.00 | 2.00 |
| Stearic Acid | | 5.00 | 5.00 | 5.00 | 5.00 |
| Mg Stearate | 1.00 | 1.00 | 1.00 | 1.00 | 1.00 |
| Total | 100.00 | 100.00 | 100.00 | 100.00 | 100.00 |

Example 3

Exemplary Eroding & Hydrogel Formulations Prepared by Wet Granulation

For purposes of illustration a number of exemplary eroding placebo formulations prepared by the method of wet granulation are provided in Table 8. In a typical preparation, a full wet granulation was employed. In such a process, the aluminum lake dye (acting as he drug surrogate) was dissolved in the appropriate diluent (water, EtOH or hydroalcoholic mixtures of a number of ratios) and was added either via direct pouring or by spraying onto the dry blend of the remaining excipients. The wet mix was then mixed in a high-shear mixer and processed to form granules of the desired size, in a high shear granulator (such as the KG-5). The formed granules were then dried in a tray oven and mixed. The final mix was fed to a Piccola rotary press (or a beta press) equipped with the specially designed load cell to enable the preparation of dosage forms. To achieve that approximately 5.5-8.0 mg of the dried granules were compressed at 1-20 KN. For some of the examples below additional excipients, such as the binder or the bioadhesive, were included in the solution that was poured over the dry blend of excipients.

Further, a number of different grades and particle sizes of mannitol can be employed to help optimize the granulation process. In the examples provided below, the mannitol grades were varied (Pearlitol 100SD, Pearlitol 200SD or Pearlitol 160C) obtain different quality granules (size, distribution, etc.).

As is well-known to those skilled in the art, there is a number of process alterations that could be used in this process. In one such alteration, a partial wet granulation was employed to prepare dosage forms. In this process only a portion of the excipients was used in the formation of the granules (intra-granular mix). In such process, the remaining excipients were added extra-granularly to the granules and the mix would be blended for a few minutes in order to create a homogeneous matrix. The formulation examples given below (Table 8) also reflect partial granulation process.

TABLE 8

Exemplary Hydrogel Formulations Prepared By Partial Wet Granulation

| Excipient | #37 | #38 | #39 | #40 | #41 | #42 |
|---|---|---|---|---|---|---|
| | Formulation # Composition, % w/w | | | | | |
| FDC Green (dye) | 0.05 | 0.05 | 0.05 | 0.05 | 0.05 | 0.05 |
| Mannitol (Pearlitol 100SD) | | | | | 73.95 | 68.96 |
| Mannitol (Pearlitol 200SD) | 73.95 | 73.6 | 75.45 | 73.95 | | |
| PEG 8000 | 15 | 14.93 | 15.00 | 15.00 | 15.00 | 20.00 |
| Microcrystalline Cellulose (MCC-Emcel 90M) | | 7.44 | | | | |
| Polyox 303 | 3 | 2.99 | 1.50 | 3.00 | 3.00 | 3.00 |
| Lutrol F68 | 2 | | 2.00 | 2.00 | 2.00 | 2.00 |
| Stearic Acid | 5 | | 5.00 | 5.00 | 5.00 | 5.00 |
| Mg Stearate | 1.00 | 1.00 | 1.00 | 1.00 | 1.00 | 1.00 |
| Total | 100.00 | 100.00 | 100.00 | 100.00 | 100.00 | 100.00 |

Example 4

Exemplary Hydrogel Formulations Prepared With Active Substance: Sufentanil Citrate For purposes of illustration, a number of formulations were prepared with active drug substance. The drug substance used in these examples is sufentanil citrate. The formulations, which are described in Table 9, were prepared for the sake of illustration using the same partial wet granulation methodology as described above and as detailed in the Table.

TABLE 9

Exemplary Hydrogel Formulations Prepared With Sufentanil Citrate

| Ingredient | #43 | #44 | #45 | #46 | #47 | #48 |
|---|---|---|---|---|---|---|
| | Formulation # Composition, % w/w | | | | | |
| Sufentanil Citrate | 0.05 | 0.27 | 0.14 | 0.068 | 0.136 | 0.273 |
| Mannitol (Pearlitol 100SD) | 73.96 | — | — | 73.9 | 73.86 | 73.7 |
| Mannitol (Pearlitol 200SD) | — | 73.77 | 73.87 | — | — | — |
| PEG 8000 | 15 | 14.98 | 15.00 | 15.00 | 15.00 | 15.00 |
| Polyox 303 | 3.00 | 3.00 | 3.00 | 3.00 | 3.00 | 3.00 |
| Lutrol F68 | 2.00 | 2.00 | 2.00 | 2.00 | 2.00 | 2.00 |
| Stearic Acid | 5.00 | 5.00 | 5.00 | 5.00 | 5.00 | 5.00 |
| Mg Stearate | 1.00 | 1.00 | 1.00 | 1.00 | 1.00 | 1.00 |
| Total | 100.00 | 100.00 | 100.00 | 100.00 | 100.00 | 100.00 |

In vitro Evaluations of Transmucosal Formulations

A number of placebo formulations of both eroding and hydrogel-type were prepared using direct compression and/or wet granulation and their properties were evaluated in vitro for bioadhesion and in vitro drug dissolution kinetics using the procedures outlined above.

TABLE 10

Exemplary Placebo Formulations for Evaluations In Vitro.

| Composition | Formulation # | | | | | |
|---|---|---|---|---|---|---|
| | 49 | 50 | 51 | 47 | 52 | 53 |
| | Composition, % w/w | | | | | |
| Aluminum Lake Dye | 0.14 | 0.14 | 0.14 | 0.14 | 0.14 | 0.14 |
| Mannitol | 83.87 | 68.87 | 56.87 | 73.86 | 51.9 | 40.7 |
| Carbopol 971 | | | 7.00 | | 20.00 | 20.00 |
| PEG 8000 | 5.00 | | 35.00 | 15.00 | 15.00 | 25.60 |
| HPMC | 10.00 | 5.00 | | | | 10.00 |
| Dibasic Calcium Phosphate | | 20.00 | | | | |
| Polyox 303 | | | | 3.00 | | 2.60 |
| Lutrol F68 | | | | 2.00 | 7.00 | |
| Stearic Acid | | 5.00 | | 5.00 | 5.00 | |
| Mg Stearate | 1.00 | 1.00 | 1.00 | 1.00 | 1.00 | 1.00 |
| Total | 100.00 | 100.00 | 100.00 | 100.00 | 100.00 | 100.00 |

Example 5

In Vitro Evaluation of Bioadhesion

The mucoadhesive strength was determined by attaching the tablets to the bottom of a hanging platform and determining the force required to detach the formulations from a porcine buccal mucosa substrate. The mucoadhesive testing system is consisting of a precision load cell (GS-500 Tranducer techniques, Temecula, Calif.) and a hook attachment. The load cell generates analogue signals, which are converted into digital signals through a data acquisition system equipped with an A/D converter and a computer; data are analyzed using EasyLx software (Keithley Metrabyte). A hanging platform comprising a glass slide attached with plastic plunger (8 cm) on the top and a circular-steel projection (0.5 cm) with flat surface on the bottom is attached to the load cell. A flat-surfaced tablet die serves as a lower static-platform. The mucosal tissue is mounted onto the lower platform using a screw-clamp. The hanging platform with the film is brought down and placed over the surface of the mucosa with a known applied force for a specified time. The detachment force in $N/cm^2$ is determined and compared. Between each measurement, the mucosal surface is rinsed with 4 mL of purified water. The excess water is wiped with a soft tissue paper and the mucosa is wetted with a known volume of phosphate buffer pH 6.8. Studies are performed in triplicate at room temperature (23-25° C.). Adhesion and peak detachment force can be used to evaluate the bioadhesive strength of dosage forms comprising various formulations of the invention. A dosage form of the invention expresses bioadhesion forces greater than 100 dynes/$cm^2$, eg 500 dynes/$cm^2$.

The bioadhesive strength of the placebo formulations was evaluated and the results are given in Table 11.

TABLE 11

Bioadhesion force of placebo Formulations.

| Formulation # | Bioadhesion force, $N/cm^2$ |
|---|---|
| 49 | 0.040 ± 0.01 |
| 47 | 0.046 ± -0.01 |
| 52 | 0.162 ± 0.15 |
| 50 | 0.030 ± 0.00 |
| 51 | 0.056 ± 0.01 |
| 53 | 0.180 ± 0.08 |

Example 6

Evaluation of Sufentanil Dissolution in Vitro from Formulations

Figure 2:
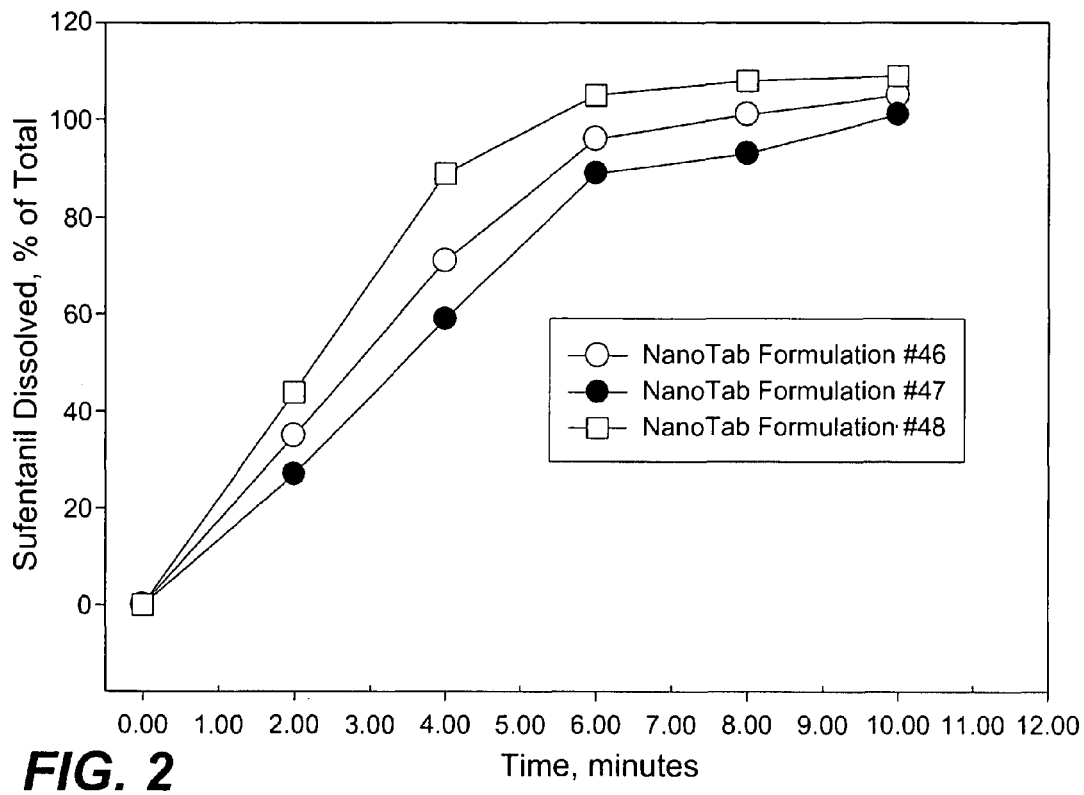
FIG. 2 is a graphic depiction of the in vitro dissolution kinetics of a NanoTab® comprising formulations #46-#48.

Sufentanil dissolution kinetics from formulations #46, #47 and #48 was determined in a Type II USP dissolution apparatus suitably modified to accommodate a small volume NanoTab® containing a small amount of sufentanil. Drug release from the bioadhesive transmucosal formulations were monitored by LC/MS. The dissolution medium was defined as phosphate buffer pH between 6.5-7.8. A dosage form of the invention has a dissolution time that typically occurs in up to about 60 minutes, however, in some cases dissolution is evident after up to about 120 minutes or 240 minutes. The results are shown in FIG. 2.

Example 7

Bioavailability and Pharmacokinetics of Sufentanil following Sublingual Administration of Formulations in a Healthy Dog Model The bioavailability of sufentanil following sublingual administration from formulation #44 as compared to intravenous was evaluated in a healthy, conscious Beagle dog animal model, as described in Table 12. Intravenous administrations were performed by single administration (n=3) of Sufenta® 50 μg/mL by bolus injection to the cephalic vein via a sterile needle and syringe of appropriate size at a dose of 5 μg of sufentanil base). For the sublingual administrations (Group 2) the test article (Formulation #44 strength of 5 μg of sufentanil base) was administered sublingually (n=3) by placement under the tongue, on to the frenulum via forceps. Blood samples were collected from a jugular or other suitable vein prior to dosing and approximately 1, 3, 5, 10, 15, 30 min, 1, 2, 4, 8 and 24 hours post-dose. Approximately 2 mL of blood were collected per timepoint into pre-chilled tubes containing $K_2$ EDTA. The samples were centrifuged at 3,000 g for approximately 10 minutes in a refrigerated centrifuge. Plasma was collected and frozen within 20 minutes of centrifugation at approximately −70° C. and was maintained at that temperature until analysis. Sample analysis was performed using a validated LC/MS/MS method for analysis of sufentanil in dog plasma.

TABLE 12

Dosing Parameters for Administration of Sufentanil (i) by sublingual administration from Sublingual Bioadhesive Formulation #44 and (ii) by an intravenous solution.

| Group | Treatment | Dose Level (μg)[a] | Route of Administration | Number of Animals[b] (Males) |
|---|---|---|---|---|
| 1 | Sufentanil solution | 5.0 | IV | 3 |
| 2 | Sufentanil NanoTab ® | 5.0 | Sublingual | 3 |

[a] = Expressed as a free base.
[b] = Same animals will be used for Groups 1 through 3 with a minimum 2-day washout period between dosing.

Figure 3:
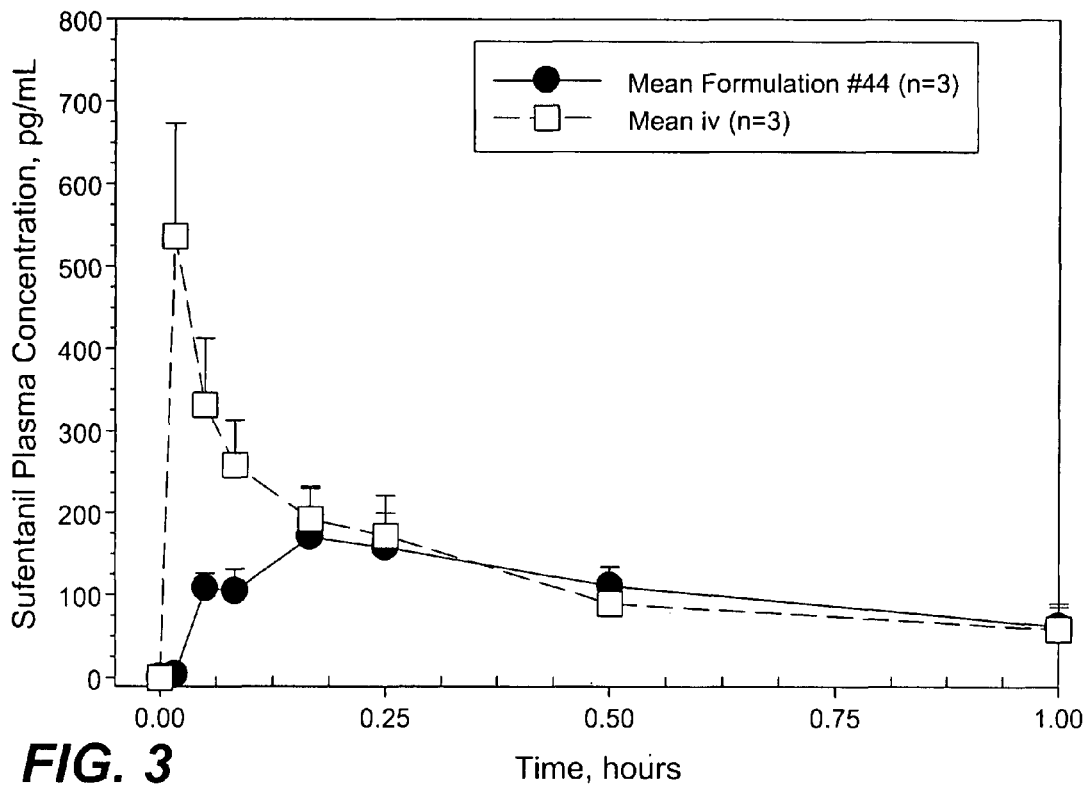
FIG. 3 is a graphic depiction of the pharmacokinetics of sufentanil following sublingual administration (n=3) of a NanoTab® comprising formulation #44, as compared to intravenous administration (n=3) in a healthy, conscious Beagle dog model. Error bars represents standard errors around the mean (SEM).

The plasma PK profiles are shown in FIG. 3. PK analysis results are summarized in Table 13.

TABLE 13

PK Analysis of Sufentanil sublingual formulation (#44) compared to intravenous sufentanil.

| Group | F (%) | Absorption Variability (% CV) | $C_{max}$ (pg/mL) | $T_{onset}$ (min)[1] | $T_{max}$ (min) | Plasma Half-life (min) | Therapeutic Time Ratio[2] |
|---|---|---|---|---|---|---|---|
| Intravenous Sufentanil | — | 22.8 | 536.7 ± 186.1 | 0.05 ± 0.06 | 1.6 ± 0.6 | 10.3 ± 4.5 | 0.05 ± 0.02 |
| Sublingual Sufentanil Formulation #44 | 74.8 ± 10.7 | 14.4 | 222.7 ± 25.9 | 7.1 ± 4.0 | 11.7 ± 2.5 | 33.3 ± 5.8 | 0.28 ± 0.16 |

[1] Time to reach 50% of $C_{max}$
[2] Represents the relative time that the drug achieves therapeutic levels (above 50% $C_{max}$), defined as time within which the drug plasma concentration is maintained above 50% of $C_{max}$ normalized by the drug's elimination half-life intravenously and it is calculated by the formula: TTR = (Time above 50% of $C_{max}$)/(Terminal intravenous elimination half-life of the drug). The denominator is obtained from literature studies of sufentanil to be 139 min in beagle dogs.

Example 8

Bioavailability and Pharmacokinetics of Sufentanil following Sublingual Solution Instillation in a Healthy Dog Model For purposes of comparison to the sufentanil dosage forms, the bioavailability and pharmacokinetics of sufentanil citrate after sublingual administration via instillation of a sufentanil solution (n=6) was evaluated and compared to IV (n=6). The bioavailability of sufentanil following sublingual administration from a solution as compared to that intravenously was evaluated in a healthy, conscious Beagle dog animal model, as described in Table 14. In both arms of the study the commercially available formulation of sufentanil citrate (Sufenta® 50 µg/mL) was used and was dosed at the same total dose of 5 µg of sufentanil base. Intravenous administrations were performed by single administration (n=3) of Sufenta® 50 µg/mL by bolus injection to the cephalic vein via a sterile needle and syringe of appropriate size. Doses were slowly applied under the tongue, adjacent to the frenulum via a sterile syringe. Blood sampling and storage mirrored the conditions described in Example #7; sample analysis was performed using a validated LC/MS/MS method for analysis of sufentanil in dog plasma.

TABLE 14

Dosing Parameters for Administration of Sufentanil (i) by sublingual administration via instillation of a sufentanil solution, (ii) by oral ingestion of a NanoTab® formulation and (ii) by an intravenous solution.

| Group | Treatment | Dose Level (µg)[a] | Route of Administration | Total Number of Animals, n |
|---|---|---|---|---|
| 1 | Sufentanil solution | 5.0 | IV | 3 |
| 2 | Sufentanil solution[c] | 5.0 | Sublingual | 6[b] |
| 3 | Ingested Formulation #44 | 5.0 | Oral | 6[b] |

[a] = Expressed as a free base.
[b] = Group 2 & 3 animals were dosed twice with a minimum 2-day washout period for a total of n = 6
[c] = Normal saline was used to dilute the test article (Sufenta® 50 µg/mL) to the desired concentration.

Figure 4:
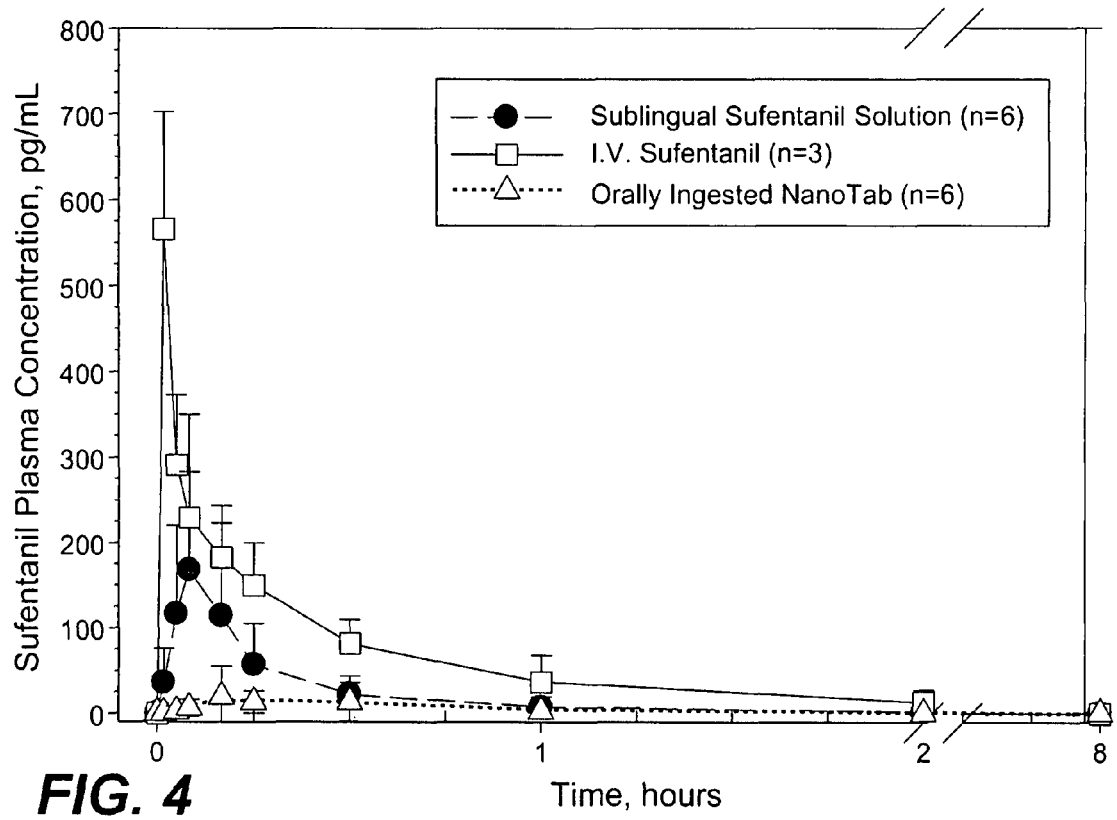
FIG. 4 is a graphic depiction of the pharmacokinetics of sufentanil following sublingual instillation (n=6) of a sufentanil solution and following oral ingestion of NanoTab® comprising formulation #44 (n=6) as compared to intravenous administration of sufentanil (n=3) in a healthy, conscious Beagle dog model. Error bars represent standard errors around the mean.

The analytical results are shown in FIG. 4. PK analysis results are summarized in Table 15.

TABLE 15

PK Analysis of intravenously administered sufentanil compared to (i) a sublingually instilled solution and (ii) an ingested NanoTab®

| Group | F (%) | Absorption Variability (% CV) | $T_{onset}$ (min)[1] | $T_{max}$ (min) | $C_{max}$ (pg/mL) | Plasma Half-life (min) | Therapeutic Time Ratio[2] |
|---|---|---|---|---|---|---|---|
| Intravenous Sufentanil | — | 39.9 | 0.5 ± 0.03 | 1.0 ± 0.0 | 594.7 ± 98.1 | 2.8 ± 0.4 | 0.02 ± 0.0 |
| Sublingual Sufentanil solution | 40.0 ± 32.5 | 81.3 | 2.7 ± 1.3 | 4.3 ± 1.0 | 209.3 ± 165.5 | 8.3 ± 4.5 | 0.04 ± 0.02 |
| Ingested NanoTab® | 12.2 ± 16.3 | 134.2 | — | 14.6 ± 9.9 | 33.8 ± 33.2 | 22.5 ± 16.8 | 0.13 ± 0.08 |

[1] Time to reach 50% of $C_{max}$
[2] Represents the relative time that the drug achieves therapeutic levels (above 50% $C_{max}$), defined as time within which the drug plasma concentration is maintained above 50% of $C_{max}$ normalized by the drug's elimination half-life intravenously and it is calculated by the formula: TTR = (Time above 50% of $C_{max}$)/(Terminal intravenous elimination half-life of the drug). The denominator is obtained from literature studies of sufentanil to be 139 min in beagle dogs.

Example 9

Evaluation of the Bioavailability and Pharmacokinetics of Sufentanil following Oral Ingestion of a Sufentanil Transmucosal Formulation The bioavailability of sufentanil following ingestion of a bioadhesive tablet described in this invention (formulation #44) as compared to that intravenously was evaluated in a healthy, conscious Beagle dog animal model, as described in the previous example. A single bioadhesive formulation prepared at a total strength of 5.0 μg of sufentanil (base units) was administered twice orally, with each dose separated by a minimum of a 2-day washout for a total of n=6 (Table 14). The bioadhesive tablets were placed manually as far back as possible in the throat and flushed with water to promote the swallow response in the animal.

Example 10

Exemplary Sufentanil Formulations to Control Drug Release and In Vivo Pharmacokinetics For purposes of illustration, a number of formulations were prepared with sufentanil citrate in order to evaluate the rate of drug release and in vivo pharmacokinetics of various dosage forms. Both eroding and hydrogel-based formulations, as described in Table 16, were prepared by direct compression, as described in Example 1, except for formulation #56, which was prepared by wet granulation, as described in Example 3.

TABLE 16

Exemplary Sufentanil Dosage Forms for Evaluation of In Vivo Drug Pharmacokinetics.

| Composition | Formulation # | | | | |
|---|---|---|---|---|---|
| | 54 | 55 | 56 | 57 | 58 |
| | Composition, % w/w | | | | |
| Sufentanil citrate | 0.2728 | 0.2728 | 0.1364 | 0.5456 | 0.5456 |
| Mannitol | 83.73 | 68.73 | 56.87 | 51.45 | 40.3 |
| Carbopol 971 | | | 7.00 | 20.00 | 20.00 |
| PEG 8000 | 5.00 | | 35.00 | 15.00 | 25.60 |
| HPMC K4M | 10.00 | 5.00 | | | 10.00 |
| Dibasic Calcium Phosphate | | 20.00 | | | |
| Polyox 303 | | | | | 2.60 |
| Lutrol F68 | | | | 7.00 | |
| Stearic Acid | | 5.00 | | 5.00 | |
| Mg Stearate | 1.00 | 1.00 | 1.00 | 1.00 | 1.00 |
| Total | 100.00 | 100.00 | 100.00 | 100.00 | 100.00 |

The pharmacokinetics of sufentanil following sublingual administration of formulations #54-58 were evaluated in a healthy, conscious Beagle dog animal model, as described in Table 17. Intravenous administrations were performed by single administration (n=3) of Sufenta® 50 μg/mL (total dose of 5 μg of sufentanil base) by bolus injection to the cephalic vein via a sterile needle and syringe of appropriate size. For the sublingual administrations the test articles (n=2 or 3) were placed under the tongue, adjacent to the frenulum via forceps. Blood sampling and storage mirrored the conditions described in Example #7; sample analysis was performed using a validated LC/MS/MS method for analysis of sufentanil in dog plasma.

TABLE 17

Dosing Parameters for Administration of Sufentanil (i) via sublingual administration of fast (#55), intermediate (#54) and slow (#58) formulations and (ii) by an intravenous solution.

| Group | Treatment | Dose Level (μg)$^a$ | Route of Administration | Dose Concentration (μg/mL) | Number of Animals (Males) |
|---|---|---|---|---|---|
| 1 | Sufenta ® | 5 | IV | 50$^a$ | 3 |
| 2 | Sufentanil-Formulation #54 | 11.0 ± 0.9 | Sublingual) | NA | 3 |
| 3 | Sufentanil Formulation #55 | 10.6 ± 0.6 | Sublingual | NA | 3 |
| 6 | Sufentanil Formulation #58 | 30.9 ± 1.4 | Sublingual | NA | 3 |

$^a$Expressed as a free base.

Figure 6:
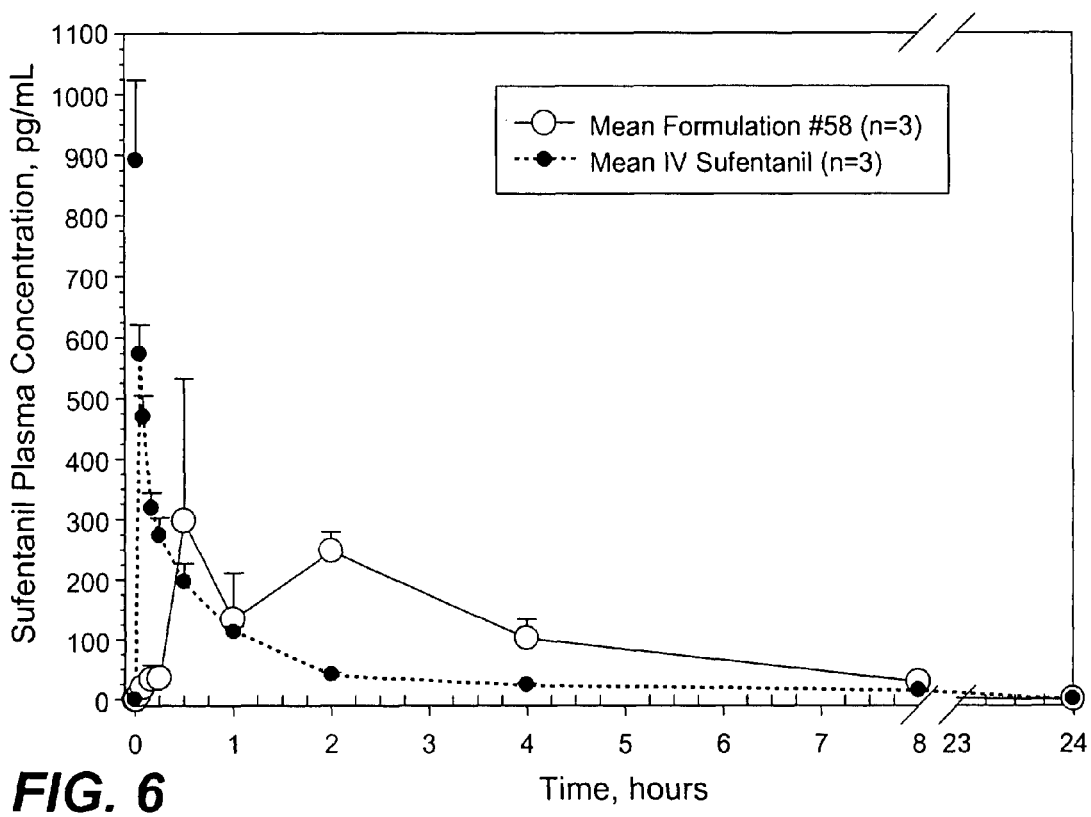
FIG. 6 is a graphic depiction of the pharmacokinetics of sufentanil following sublingual administration of slowly-disintegrating NanoTab® formulation #58 (n=3), as compared to intravenous administration of sufentanil (n=3) in a healthy, conscious Beagle dog model. Error bars represent standard errors around the mean.

The results are shown in FIGS. 5 and 6. PK results are summarized in Tables 18 and 19.

TABLE 18

PK Analysis sublingual fast- and intermediate-disintegrating Sufentanil formulations compared to intravenously administered Sufenta ®.

| Group | F (%) | Absorption Variability (% CV) | $T_{onset}$ (min)[1] | $T_{max}$ (min) | $C_{max}$ (pg/mL) | Plasma Half-life (min) | Therapeutic Time Ratio[2] |
|---|---|---|---|---|---|---|---|
| Intravenous Sufentanil | — | 5.4 | 0.6 ± 0.0 | 1.0 ± 0.0 | 1002.1 ± 149.1 | 7.9 ± 2.5 | 0.05 ± 0.02 |
| Sublingual Formulation #54 | 88.2 ± 28.9 | 32.8 | 9.2 ± 4.3 | 25 ± 8.7 | 727.2 ± 256.3 | 49.2 ± 22.0 | 0.28 ± 0.13 |

TABLE 18-continued

PK Analysis sublingual fast- and intermediate-disintegrating Sufentanil formulations compared to intravenously administered Sufenta ®.

| Group | F (%) | Absorption Variability (% CV) | $T_{onset}$ (min)[1] | $T_{max}$ (min) | $C_{max}$ (pg/mL) | Plasma Half-life (min) | Therapeutic Time Ratio[2] |
|---|---|---|---|---|---|---|---|
| Sublingual Formulation #55 | 90.4 ± 25.3 | 28 | 7.1 ± 0.5 | 13.3 ± 2.9 | 819.1 ± 100.1 | 26.7 ± 2.2 | 0.14 ± 0.02 |

[1] Time to reach 50% of $C_{max}$
[2] Represents the relative time that the drug achieves therapeutic levels (above 50% $C_{max}$), defined as time within which the drug plasma concentration is maintained above 50% of $C_{max}$ normalized by the drug's elimination half-life intravenously and it is calculated by the formula: TTR = (Time above 50% of $C_{max}$)/(Terminal intravenous elimination half-life of the drug). The denominator is obtained from literature studies of sufentanil to be 139 min in beagle dogs.

TABLE 19

PK Analysis sublingual slow-disintegrating Sufentanil formulations compared to intravenously administered Sufenta ®.

| Group | $T_{onset}$ (min)[1] | $T_{max}$ (min) | $C_{max}$ (pg/mL) | Plasma Half-life (min) | Therapeutic Time Ratio[2] |
|---|---|---|---|---|---|
| Intravenous Sufentanil | 0.6 ± 0.0 | 1.0 ± 0.0 | 1002.1 ± 149.1 | 7.9 ± 2.5 | 0.05 ± 0.02 |
| Sublingual Formulation #58 | 48 ± 34.1 | 70 ± 45.8 | 420.9 ± 298.4 | 205 ± 93.1 | 1.13 ± 0.69 |

[1] Time to reach 50% of $C_{max}$
[2] Represents the relative time that the drug achieves therapeutic levels (above 50% $C_{max}$), defined as time within which the drug plasma concentration is maintained above 50% of $C_{max}$ normalized by the drug's elimination half-life intravenously and it is calculated by the formula: TTR = (Time above 50% of $C_{max}$)/(Terminal intravenous elimination half-life of the drug). The denominator is obtained from literature studies of sufentanil to be 139 min in beagle dogs.

Example 11

In vivo Evaluation of Sublingual Fentanyl Formulations in a Dog Model

For purposes of illustration, a number of transmucosal formulations were prepared with fentanyl citrate in order to evaluate the rate of drug release and in vivo pharmacokinetics of various dosage forms. Both eroding and hydrogel-based formulations, as described in Table 20, were evaluated; all dosage forms were prepared by direct compression, as described in Example 1.

TABLE 20

Exemplary Fentanyl Formulations for Evaluation In Vivo.

| | Formulation # | | |
|---|---|---|---|
| | 59 | 60 | 62 |
| Composition | Composition, % w/w | | |
| Fentanyl citrate | 2.00 | 2.00 | 2.00 |
| Mannitol | 72.00 | 55.00 | 38.80 |
| Carbopol 974 | | 7.00 | 20.00 |
| PEG 8000 | 15.00 | 35.00 | 25.60 |
| HPMC K4M | | | 10.00 |
| Polyox 303 | 3.00 | | 2.60 |
| Lutrol F68 | 2.00 | | |
| Stearic Acid | 5.00 | | |
| Mg Stearate | 1.00 | 1.00 | 1.00 |
| Total | 100.00 | 100.00 | 100.00 |

The pharmacokinetics of fentanyl following sublingual administration from a number of formulations intended to provide distinct PK profiles as compared to that intravenously was evaluated in a healthy, conscious Beagle dog animal model, as described in Table 21. The commercially available formulation of fentanyl citrate (Sublimaze® 50 µg/mL) was used and was dosed at the same total dose of 70 µg of fentanyl base. Intravenous administrations were performed by single administration (n=3) of Sublimaze® 50 µg/mL by bolus injection to the cephalic vein via a sterile needle and syringe of appropriate size. Both hydrogel and eroding formulations were developed to provide intermediate and slow release of the drug from the dosage form. For the sublingual administrations the test articles were administered sublingually (n=2 or 3) by placement under the tongue, adjacent to the frenulum via forceps. Blood sampling and storage mirrored the conditions described in Example 7; sample analysis was performed using a validated LC/MS/MS method for analysis of fentanyl in dog plasma.

TABLE 21

Dosing Parameters for Administration of Fentanyl (i) via sublingual administration of intermediate (#59, 60) and slow-acting (#62) formulations and (ii) by an intravenous solution.

| Group | Treatment | Dose Level (μg)[a] | Route of Administration | Dose Volume (mL) | Dose Concentration (μg/mL) | Number of Animals (Males) |
|---|---|---|---|---|---|---|
| 1 | Sublimaze ® | 70 | IV | 1.4 | 50[a] | 3 |
| 2 | Fentanyl-Formulation #59 | 74.1 ± 3.6 | Sublingual | NA | NA | 2 |
| 3 | Fentanyl Formulation #60 | 74.7 ± 3.8 | Sublingual | NA | NA | 2 |
| 5 | Fentanyl Formulation #62 | 69.3 ± 5.6 | Sublingual | NA | NA | 3 |

[a]Expressed as a free base.

The results are shown in FIGS. 7 and 8. Pharmacokinetic analysis results are summarized in Table 22.

TABLE 22

PK Analysis of sublingually administered Fentanyl formulations as compared to intravenous Sublimaze ®.

| Group | F (%) | Absorption Variability (% CV) | $T_{onset}$ (min)[1] | $T_{max}$ (min) | $C_{max}$ (pg/mL) | Plasma Half-life (min) | Therapeutic Time Ratio[2] |
|---|---|---|---|---|---|---|---|
| Intravenous Fentanyl | — | 13.7 | 0.6 ± 0.0 | 1.0 ± 0.0 | 7895.9 ± 6096 | 10.5 ± 9.6 | 0.04 ± 0.04 |
| Sublingual Formulation #59 | 96.9 ± 8.2 | 8.4 | 16.2 ± 6.8 | 45 ± 21.2 | 3304.5 ± 2398 | 75.5 ± 32.5 | 0.24 ± 0.16 |
| Sublingual Formulation #60 | 95.4 ± 10 | 10.5 | 9.0 ± 2.6 | 22.5 ± 10.6 | 1188.2 ± 42.4 | 121.5 ± 19.1 | 0.46 ± 0.07 |
| Sublingual Formulation #62 | 99.0 ± 4.4 | 4.5 | 43.6 ± 20.7 | 50 ± 17.3 | 2226.9 ± 811.5 | 154.4 ± 52.6 | 0.46 ± 0.12 |

[1]Time to reach 50% of $C_{max}$

[2]Represents the relative time that the drug achieves therapeutic levels (above 50% $C_{max}$), defined as time within which the drug plasma concentration is maintained above 50% of $C_{max}$ normalized by the drug's elimination half-life intravenously and it is calculated by the formula: TTR = (Time above 50% of $C_{max}$)/(Terminal intravenous elimination half-life of the drug). The denominator is obtained from literature intravenous studies of fentanyl to be 244 min in beagle dogs.

The pharmacokinetics of sublingual fentanyl from medium-disintegrating NanoTabs® are illustrated in FIG. 7. The pharmacokinetics of sublingual fentanyl from slow-disintegrating Nano Tabs® are illustrated in FIG. 8.

Example 12

In vivo Evaluation of Sublingual Alfentanil HCl Formulations in a Dog Model For purposes of illustration, an eroding dosage form was prepared with alfentanil HCl in order to demonstrate the ability of the dosage forms described in this application to modulate and control the rate of drug release and ultimately in vivo pharmacokinetics. The formulation composition is described in Table 23; all tablets were prepared by direct compression, as described in Example 1.

TABLE 23

Exemplary Alfentanil Formulations for Evaluation of In Vivo Drug Pharmacokinetics.

| Composition | Formulation # 63 Composition, % w/w |
|---|---|
| Alfentanil HCl | 5.00 |
| Mannitol | 52.00 |
| Carbopol 974 | 7.00 |
| PEG 8000 | 35.00 |
| Mg Stearate | 1.00 |
| Total | 100.00 |

The bioavailability and pharmacokinetics of alfentanil following sublingual administration from a formulation as compared to that intravenously was evaluated in a healthy, conscious Beagle dog animal model, as described in Table 24. Intravenous administrations were performed by single administration (n=3) of Alfentanil HCl (Alfenta® 500 μg/mL by bolus injection to the cephalic vein via a sterile needle and syringe of appropriate size at a dose of 253 μg of alfentanil base). For the sublingual administrations the test article (Formulation #63, strength of 239±16.2 μg of alfentanil base) was administered sublingually (n=2) by placement under the tongue, adjacent to the frenulum via forceps. Blood sampling and storage mirrored the conditions described in Example 7; sample analysis was performed using a validated LC/MS/MS method for analysis of alfentanil in dog plasma.

TABLE 24

Dosing Parameters for Administration of Alfentanil (i) sublingually from a formulation and (ii) by an intravenous solution.

| Group | Treatment | Dose Level (μg)[a] | Route of Administration | Number of Animals (Males) |
|---|---|---|---|---|
| 1 | Alfentanil solution | 253 | IV | 3 |
| 2 | Alfentanil Formulation | 239.0 ± 16.2 | Sublingual | 2 |

[a] = Expressed as a free base.
[b] = Same animals will be used for Groups 1 through 3 with a minimum 2-day washout period between dosing.

The results are shown in FIG. 9. PK analysis results are summarized in Table 25.

TABLE 25

PK Analysis of Alfentanil sublingual formulations compared to intravenous alfentanil

| Group | F (%) | Absorption Variability (% CV) | $T_{onset}$ (min)[1] | $T_{max}$ (min) | $C_{max}$ (ng/mL) | Plasma Half-life (min) | Therapeutic Time Ratio[2] |
|---|---|---|---|---|---|---|---|
| Intravenous Alfentanil | — | 10.5 | 0.5 ± 0.05 | 1 ± 0 | 139.1 ± 76.4 | 4.4 ± 2.4 | 0.04 ± 0.02 |
| Sublingual Alfentanil Formulation | 94.1 ± 4.6 | 4.9 | 11.7 ± 1.3 | 15.0 ± 4.2 | 35.5 ± 2.6 | 40.8 ± 8.5 | 0.33 ± 0.07 |

[1] Time to reach 50% of $C_{max}$
[2] Represents the relative time that the drug achieves therapeutic levels (above 50% $C_{max}$), defined as time within which the drug plasma concentration is maintained above 50% of $C_{max}$ normalized by the drug's elimination half-life intravenously and it is calculated by the formula: TTR = (Time above 50% of $C_{max}$)/(Terminal intravenous elimination half-life of the drug). The denominator is obtained from literature studies of alfentanil to be 104 min in beagle dogs.

Example 13

Evaluation of the Pharmacokinetics of Sufentanil from Bioadhesive NanoTab® Formulations in Human Volunteers The bioadhesive transmucosal formulations #46, #47 and #48 which are described in Table 9 (respective doses of 2.5, 5.0 and 10.0 μg of sufentanil base units, respectively) were evaluated in a crossover human clinical study in 12 human volunteers with wash-out periods between transitions from higher to lower doses. Subjects were blocked with naltrexone daily to avoid opioid-induced side-effects. The sufentanil Nano Tab® formulations were administered sublingually at the base of the frenulum using forceps. For comparison, intravenous sufentanil at a total dose of 5 μg was prepared by dilution of commercially available Sufenta® (strength of 50 μg/mL) in 0.9% saline to a total volume of 20 mL and was administered through an IV catheter as a continuous infusion over 10 minutes. Plasma samples were drawn from all subjects and for all groups at −5.0 (before the start of infusion), 2.5, 5, 7.5, 10, 12.5, 15, 20, 30, 45, 60, 90, 120, 160, 320, 480 and 640 minutes post-administration.

In addition, the pharmacokinetics of sufentanil were evaluated in the same 12 volunteers following repeated-dosing of four 5.0 mg formulation (#47) administered at 10 minute intervals. Administration was performed as described above. Plasma samples were drawn from all subjects at the following time points: −5.0 (before the first NanoTab® administration), 5, 7.5 minutes, 10 (immediately prior to the second NanoTab® administration), 15, 17.5 minutes, 20 (immediately prior to the third Nano Tab® administration), 25, 27.5 minutes, 30 (immediately prior to the fourth NanoTab® administration), 35, 40, 45, 50, 55, 60, 90, 120, 150, 190, 350, 510 and 670 minutes. Sufentanil concentrations in plasma were determined using a fully validated LC-MS/MS sufentanil plasma assay.

The disintegration of the Nano Tab® formulations in humans was monitored in the study. All NanoTabs® used in this study disintegrated over a period of 10-30 minutes in all subjects. After placement of each sufentanil sublingual Nano Tab® in the sublingual cavity of the 12 healthy volunteers, a remarkably consistent pharmacokinetic profile was obtained for the three dosages, as illustrated in FIG. 10 and summarized in Table 26.

TABLE 26

Pharmacokinetic Analysis of the sufentanil following sublingual administration of NanoTab ® formulations (#46 at 2.5 μg strength, #47 at 5.0 μg strength and #48 at 10 μg strength all at n = 12) compared to IV (n = 12) in human volunteers

| Group | F (%) | Absorption Variability (% CV) | $C_{max}$ (pg/mL) | $T_{max}$ (min) | Plasma Elimination Half-life (hr) | Therapeutic Time Ratio[1] |
|---|---|---|---|---|---|---|
| Intravenous Sufentanil | — | 20.7 | 0.0813 ± 0.0281 | 0.16 ± 0.03 | 1.19 ± 0.18 | 0.067 |
| Sublingual Sufentanil Formulation #46 | 97.8 | 24.7 | 0.0068 ± 0.0021 | 0.73 ± 0.13 | 1.65 ± 0.43 | 0.74 |
| Sublingual Sufentanil Formulation #47 | 76.7 | 34.1 | 0.0109 ± 0.0035 | 0.77 ± 0.29 | 1.54 ± 0.57 | 0.75 |
| Sublingual Sufentanil Formulation #48 | 98.2 | 27.5 | 0.0275 ± 0.0077 | 0.68 ± 0.22 | 1.71 ± 0.40 | 0.72 |
| Repeat Dosing of #47 NanoTab every 10 min. × 4 | 96.4 | 25.7 | 0.0464 ± 0.0124 | 1.04 ± 0.23 | 1.97 ± 0.30 | NA |

[1]Represents the relative time that the drug achieves therapeutic levels (above 50% of $C_{max}$) and it is calculated by the formula: TTR = (Time spent above 50% of $C_{max}$)/(IV Terminal elimination half-life). The denominator is obtained from literature and is 148 min in humans for sufentanil.

Example 14

Additional Exemplary Formulations Prepared by Direct Compression

For purposes of illustration a number of exemplary eroding placebo formulations prepared by the method of direct compression are provided below in Tables 27-28 which show the % w/w compositions of the excipients.

TABLE 27

Formulations prepared by direct compression

| Ingredients | A1 6HF | A2 6HF-1 | A3 6HF-2 | A4 5EF | A5 5EF-1 | A6 5EF-2 |
|---|---|---|---|---|---|---|
| Aluminum blue lake (dye) | 0.13 | 0.13 | 0.13 | 0.13 | 0.13 | 0.13 |
| Mannitol | 83.87 | 88.87 | 83.87 | 68.87 | 73.87 | 68.87 |
| Stearic Acid |  |  |  | 5.00 |  |  |
| Pluronic F68 |  |  |  |  |  |  |
| Dibasic Calcium Phosphate |  |  |  | 20.00 | 20.00 | 20.00 |
| HPMC - E4 | 10.00 | 10.00 | 15.00 | 5.00 | 5.00 | 10.00 |
| PEG 8000 | 5.00 |  |  |  |  |  |
| Mg Stearate | 1.00 | 1.00 | 1.00 | 1.00 | 1.00 | 1.00 |
| Total | 100 | 100 | 100 | 100 | 100 | 100 |

TABLE 28

Formulations prepared by direct compression

| Ingredients | 5EF A7 | 5EF-3 A8 | 5EF-4 A9 | 5EF-5 A10 | 5EF-6 A11 | 5EF-7 A12 |
|---|---|---|---|---|---|---|
| Aluminum blue lake (dye) | 0.13 | 0.13 | 0.13 | 0.13 | 0.13 | 0.13 |
| Mannitol | 68.87 | 63.87 | 53.87 | 63.87 | 63.87 | 63.87 |
| Stearic Acid | 5.00 | 5.00 | 5.00 | 5.00 | 5.00 | 5.00 |
| Pluronic F68 |  |  |  |  |  |  |
| Polyox 303 |  |  |  |  |  |  |
| Dibasic Calcium Phosphate | 20.00 | 20.00 | 20.00 | 20.00 | 20.00 | 20.00 |
| HPMC - E4 - (HPMC - 2910, 3000-5600 cps) | 5.00 | 10.00 | 20.00 |  |  |  |
| HPMC - E10 - (HPMC - 2910, 7500-14000 cps) |  |  |  | 10.00 |  |  |
| HPMC - K4 - (HPMC - 2208, 3000-5600 cps) |  |  |  |  | 10.00 |  |

TABLE 28-continued

Formulations prepared by direct compression

| Ingredients | 5EF A7 | 5EF-3 A8 | 5EF-4 A9 | 5EF-5 A10 | 5EF-6 A11 | 5EF-7 A12 |
|---|---|---|---|---|---|---|
| HPMC - K100 - (HPMC - 2208, 80000-120000 cps) | | | | | | 10.00 |
| PEG 8000 | | | | | | |
| Mg Stearate | 1.00 | 1.00 | 1.00 | 1.00 | 1.00 | 1.00 |
| Total | 100 | 100 | 100 | 100 | 100 | 100 |

Example 15

Exemplary Formulations Prepared by Wet Granulation

For purposes of illustration a number of exemplary eroding placebo formulations prepared by the method of wet granulation are provided below in Tables 29-32 which show the % w/w compositions of the excipients.

TABLE 29

Formulations prepared by wet granulation

| Ingredients | 5EF A13 | 5EF-4 A14 | 5EF-6 A15 |
|---|---|---|---|
| Ferric Oxide - Red Dye | 0.13 | 0.13 | 0.13 |
| Mannitol | 68.87 | 53.87 | 63.87 |
| Dibasic Calcium Phosphate | 20.00 | 20.00 | 20.00 |
| HPMC - E4- (HPMC- 2910, 3000-5600 cps) | 5.00 | 20.00 | |
| HPMC - K4 - (HPMC- 2208, 3000-5600 cps) | | | 10.00 |
| Stearic Acid | 5.00 | 5.00 | 5.00 |
| Mg Stearate | 1.00 | 1.00 | 1.00 |
| Total | 100 | 100 | 100 |

TABLE 30

Formulations prepared by wet granulation

| Ingredients | 5EF-6 A16 | 5EF-6A A17 | 5EF-6A1 A18 | 5EF-6A1a A19 | 5EF-6A2 A20 | 5EF-6B A21 | 5EF-6C A22 |
|---|---|---|---|---|---|---|---|
| Ferric Oxide - Red Dye | 0.13 | 0.13 | 0.13 | 0.13 | 0.13 | 0.13 | 0.13 |
| Mannitol | 63.87 | 63.87 | 59.87 | 55.87 | 59.87 | 68.87 | 55.87 |
| Dibasic Calcium Phosphate | 20.00 | 12.00 | 16.00 | 12.00 | 16.00 | 20.00 | 20.00 |
| HPMC - K4M - (HPMC - 2208, 3000-5600 cps) | 10.00 | 10.00 | 10.00 | 10.00 | 9.00 | 5.00 | 10.00 |
| HPMC in granulating fluid (HPMC E5) | | | | | 1.00 | | |
| PVP XL | | 8.00 | 8.00 | 16.00 | 8.00 | | |
| Ac-Di-Sol | | | | | | | 8.00 |
| Stearic Acid | 5.00 | 5.00 | 5.00 | 5.00 | 5.00 | 5.00 | 5.00 |
| Mg Stearate | 1.00 | 1.00 | 1.00 | 1.00 | 1.00 | 1.00 | 1.00 |
| Total | 100 | 100 | 100 | 100 | 100 | 100 | 100 |

TABLE 31

Formulations prepared by wet granulation

| | Lot # | | | | | | | | |
|---|---|---|---|---|---|---|---|---|---|
| Ingredients | A23 5EF-6 | A24 5EF-6'''' | A25 5EF-6D | A26 5EF-6E | A27 5EF-6F | A28 5EF-6G | A29 5EF-6H | A30 5EF-6I | A31 5EF-6J |
| Ferric Oxide - Red Dye | 0.13 | 0.13 | 0.13 | 0.13 | 0.13 | 0.13 | 0.13 | 0.13 | 0.13 |

TABLE 31-continued

Formulations prepared by wet granulation

| Ingredients | A23 5EF-6 | A24 5EF-6"" | A25 5EF-6D | A26 5EF-6E | A27 5EF-6F | A28 5EF-6G | A29 5EF-6H | A30 5EF-6I | A31 5EF-6J |
|---|---|---|---|---|---|---|---|---|---|
| Mannitol | 63.87 | 63.87 | 72.87 | 70.87 | 63.87 | | | | |
| Sorbitol | | | | | | 63.87 | 83.87 | | |
| Microcrystalline Cellulose | | | | | | | | 43.87 | 43.87 |
| Dibasic Calcium Phosphate | 20.00 | 20.00 | 20.00 | 20.00 | 20.00 | 20.00 | | 20.00 | 20.00 |
| HPMC - K4M - (HPMC - 2208, 3000-5600 cps) | 10.00 | 10.00 | 1.00 | 3.00 | | 10.00 | 10.00 | 10.00 | |
| HPC | | | | | 10.00 | | | | |
| HPMC-E5 | | | | | | | | | 10.00 |
| PVP XL | | | | | | | | 20.00 | 20.00 |
| Stearic Acid | 5.00 | 5.00 | 5.00 | 5.00 | 5.00 | 5.00 | 5.00 | 5.00 | 5.00 |
| Mg Stearate | 1.00 | 1.00 | 1.00 | 1.00 | 1.00 | 1.00 | 1.00 | 1.00 | 1.00 |
| Total | 100 | 100 | 100 | 100 | 100 | 100 | 100 | 100 | 100 |

TABLE 32

Formulations prepared by wet granulation

| | Lot # | | |
|---|---|---|---|
| | A32 | A33 | A34 |
| | Formulation Code | | |
| Ingredients | 5EF-6 | 5EF-6B | 5EF-6E |
| Bromocresol Purple (dye) | 0.13 | 0.13 | 0.13 |
| Mannitol | 63.77 | 68.77 | 70.77 |
| Dibasic Calcium Phosphate | 20.00 | 20.00 | 20.00 |
| BHT | 0.05 | 0.05 | 0.05 |
| HPMC - K4M - (HPMC- 2208, 3000-5600 cps) | 10.00 | 5.00 | 3.00 |
| Stearic Acid | 5.00 | 5.00 | 5.00 |
| Mg Stearate | 1.00 | 1.00 | 1.00 |
| BHT | 5.00 | 0.05 | 0.05 |
| Total | 104.95 | 100.00 | 100.00 |

Example 16

Exemplary Formulations Prepared by Granulation

For purposes of illustration a number of exemplary eroding placebo formulations prepared by granulation are provided below in Tables 33-37 which show the % w/w compositions of the excipients.

TABLE 33

Formulations prepared by granulation

| | Lot# | | | |
|---|---|---|---|---|
| Ingredients | A36 | A37 | A38 | A39 |
| BromoCresol Purple (dye) | 0.28 | 0.28 | 0.28 | 0.28 |
| Mannitol | 70.62 | 65.62 | 67.62 | 67.62 |
| Dibasic Calcium Phosphate | 20.00 | 20.00 | 20.00 | 20.00 |
| Sodium Starch Glycolate | | | 5.00 | |
| HPMC - K4M - (HPMC- 2208, 3000-5600 cps) | | 3.00 | 3.00 | 3.00 |
| HPMC-K100 LV | 3.00 | | | |

TABLE 33-continued

Formulations prepared by granulation

| | Lot# | | | |
|---|---|---|---|---|
| Ingredients | A36 | A37 | A38 | A39 |
| Ac-Di-Sol | | | 3.00 | |
| PVP XL | | | | 3.00 |
| BHT | 0.05 | 0.05 | 0.05 | 0.05 |
| BHT | 0.05 | 0.05 | 0.05 | 0.05 |
| Stearic Acid | 5.00 | 5.00 | 5.00 | 5.00 |
| Mg Stearate | 1.00 | 1.00 | 1.00 | 1.00 |
| Total | 100.00 | 100.00 | 100.00 | 100.00 |
| Granulating Fluid (Ethanol:water) | (95:5) | (95:5) | (95:5) | (95:5) |

TABLE 34

Formulations prepared by granulation

| | Lot# | | | | | |
|---|---|---|---|---|---|---|
| Ingredients | A40 | A41 | A42 | A43 | A44 | A45 |
| BromoCresol Purple (dye) | 0.28 | 0.28 | 0.28 | 0.28 | 0.28 | 69.62 |
| Mannitol | 65.62 | 62.62 | 65.62 | 62.62 | 70.52 | 20.00 |
| Dibasic Calcium Phosphate | 20.00 | 20.00 | 20.00 | 20.00 | 20.00 | 3.00 |
| HPMC - K4 - (HPMC - 2208, 3000-5600 cps) | 3.00 | 3.00 | 3.00 | 3.00 | 3.00 | |
| PVP XL | | 3.00 | | 3.00 | | |
| Lutrol F68 | 5.00 | 5.00 | | | | |
| Lutrol F127 | | | 5.00 | 5.00 | | |
| Tween 80 | | | | | 0.10 | 1.00 |
| BHT | 0.05 | 0.05 | 0.05 | 0.05 | 0.05 | 0.05 |
| BHT | 0.05 | 0.05 | 0.05 | 0.05 | 0.05 | 0.05 |
| Stearic Acid | 5.00 | 5.00 | 5.00 | 5.00 | 5.00 | 5.00 |
| Mg Stearate | 1.00 | 1.00 | 1.00 | 1.00 | 1.00 | 1.00 |
| Total | 100.00 | 100.00 | 100.00 | 100.00 | 100.00 | 100.00 |
| Granulating Fluid (Ethanol:water) | (95:5) | (95:5) | (95:5) | (95:5) | (95:5) | (95:5) |

TABLE 35

Formulations prepared by granulation

| Ingredients | A46 | A47 | A48 | A49 | A50 | A51 | A52 | A53 |
|---|---|---|---|---|---|---|---|---|
| BromoCresol Purple | 0.28 | 0.28 | 0.28 | 0.28 | 0.28 | 0.28 | 0.28 | 0.28 |
| Mannitol | 75.62 | 82.62 | 49.62 | 78.12 | 48.62 | 45.12 | 52.12 | 79.12 |
| Dibasic Calcium Phosphate | 10.0 | 10.0 | 40.0 | 10.0 | 40.0 | 40.0 | 40.0 | 10.0 |
| HPMC - K100LV | 3.0 | 0.0 | 3.0 | 0.0 | 0.0 | 3.0 | 0.0 | 3.0 |
| Ac-di-sol | 5.0 | 1.0 | 1.0 | 5.0 | 5.0 | 5.0 | 1.0 | 1.0 |
| Tween 80 | 0.0 | 0.0 | 0.0 | 0.5 | 0.0 | 0.5 | 0.5 | 0.5 |
| BHT | 0.05 | 0.05 | 0.05 | 0.05 | 0.05 | 0.05 | 0.05 | 0.05 |
| BHT | 0.05 | 0.05 | 0.05 | 0.05 | 0.05 | 0.05 | 0.05 | 0.05 |
| Stearic Acid | 5.00 | 5.00 | 5.00 | 5.00 | 5.00 | 5.00 | 5.00 | 5.00 |
| Mg Stearate | 1.00 | 1.00 | 1.00 | 1.00 | 1.00 | 1.00 | 1.00 | 1.00 |
| Total | 100.00 | 100.00 | 100.00 | 100.00 | 100.00 | 100.00 | 100.00 | 100.00 |
| Granulating Fluid (Ethanol:water) | (95:5) | (95:5) | (95:5) | (95:5) | (95:5) | (95:5) | (95:5) | (95:5) |

TABLE 36

Formulations prepared by granulation

| Ingredients/Core ID | A54 | A55 | A56 | A57 | A58 | A59 | A60 | A61 | A62 | A63 |
|---|---|---|---|---|---|---|---|---|---|---|
|  | 85 | 86 | 87 | 88 | 89 | 90 | 91 | 92 | 93 | 94 |
| BromoCresol Purple | 0.28 | 0.28 | 0.28 | 0.28 | 0.28 | 0.28 | 0.28 | 0.28 | 0.28 | 0.28 |
| Mannitol | 72.62 | 70.62 | 80.62 | 67.62 | 69.62 | 62.62 | 70.62 | 67.62 | 67.62 | 60.62 |
| Dibasic Calcium Phosphate | 20.0 |  |  |  |  | 20.0 |  |  | 20.0 | 20.0 |
| MCC (Avicel 102) |  | 20.0 | 10.0 | 20.0 | 20.0 |  |  |  |  |  |
| HPMC - K4M |  | 3.0 | 3.0 | 3.0 |  | 3.0 | 3.0 | 3.0 |  |  |
| PEO 303 | 1.0 |  |  |  | 1.0 |  |  |  |  |  |
| Maltodextrin |  |  |  |  |  |  |  |  | 3.0 | 10.0 |
| Ac-di-sol |  |  |  | 3.0 | 3.0 | 3.0 |  | 3.0 | 3.0 | 3.0 |
| Na starch glycolate |  |  |  |  |  | 5.0 |  |  |  |  |
| NaHCO3 |  |  |  |  |  |  | 20.0 | 20.0 |  |  |
| BHT | 0.05 | 0.05 | 0.05 | 0.05 | 0.05 | 0.05 | 0.05 | 0.05 | 0.05 | 0.05 |
| BHT | 0.05 | 0.05 | 0.05 | 0.05 | 0.05 | 0.05 | 0.05 | 0.05 | 0.05 | 0.05 |
| Stearic Acid | 5.00 | 5.00 | 5.00 | 5.00 | 5.00 | 5.00 | 5.00 | 5.00 | 5.00 | 5.00 |
| Mg Stearate | 1.00 | 1.00 | 1.00 | 1.00 | 1.00 | 1.00 | 1.00 | 1.00 | 1.00 | 1.00 |
| Total | 100.00 | 100.00 | 100.00 | 100.00 | 100.00 | 100.00 | 100.00 | 100.00 | 100.00 | 100.00 |
| Granulating Fluid (Ethanol:water) | (95:5) | (95:5) | (95:5) | (95:5) | (95:5) | (95:5) | (95:5) | (95:5) | (95:5) | (95:5) |

TABLE 37

Formulations prepared by granulation

| Ingredients/Core ID | A64 | A65 | A66 | A67 | A68 | A69 |
|---|---|---|---|---|---|---|
|  | 96 | 97 | 98 | 99 | 100 | 101 |
| BromoCresol Purple | 0.28 | 0.28 | 0.28 | 0.28 | 0.28 | 0.28 |
| Mannitol | 80.62 | 77.62 | 74.62 | 77.62 | 77.62 | 80.62 |
| Dibasic Calcium Phosphate |  |  |  |  |  |  |
| MCC (Avicel 102) | 10.0 | 10.0 | 15.0 |  | 10.0 | 10.0 |
| HPMC-K4M | 3.0 | 3.0 |  | 3.0 |  |  |
| PEO 303 |  |  | 1.0 |  |  |  |
| Maltodextrin |  |  |  |  | 3.0 | 3.0 |
| Ac-di-sol |  | 3.0 | 3.0 | 3.0 | 3.0 |  |
| NaHCO3 |  |  |  | 10.0 |  |  |
| BHT | 0.05 | 0.05 | 0.05 | 0.05 | 0.05 | 0.05 |

TABLE 37-continued

Formulations prepared by granulation

| | Lot# | | | | | |
|---|---|---|---|---|---|---|
| | A64 | A65 | A66 | A67 | A68 | A69 |
| BHT | 0.05 | 0.05 | 0.05 | 0.05 | 0.05 | 0.05 |
| Stearic Acid | 5.00 | 5.00 | 5.00 | 5.00 | 5.00 | 5.00 |
| Mg Stearate | 1.00 | 1.00 | 1.00 | 1.00 | 1.00 | 1.00 |
| Total | 100.00 | 100.00 | 100.00 | 100.00 | 100.00 | 100.00 |
| Granulating Fluid (Ethanol:water) | (95:5) | (95:5) | (95:5) | (95:5) | (95:5) | (95:5) |

What is claimed is:

1. A bioadhesive tablet for sublingual administration to a subject, comprising:
   (a) from about 2.5 to about 100 micrograms of sufentanil, expressed as the base; and
   (b) a bioadhesive material, wherein said bioadhesive material is present at 2-30% by weight and provides for adherence to the oral mucosa of said subject, and said tablet has a volume of from about 0.1 microliters to about 50 microliters, wherein after administration of said tablet to said subject, said tablet provides a minimal saliva response and minimal swallowing of sufentanil; and at least 55% of drug delivery of sufentanil occurs via the oral transmucosal route.

2. The tablet according to claim 1, wherein said tablet becomes a hydrogel upon contact with an aqueous fluid.

3. The tablet according to claim 1, wherein said tablet is an eroding tablet wherein upon contact with an aqueous fluid, the surface of the tablet hydrates and erodes, without formation of a hydrogel.

4. The tablet according to claim 1, wherein upon contact with an aqueous fluid said tablet disintegrates and forms a film.

5. The tablet according to claim 1, wherein dissolution of said tablet is independent of pH.

6. The tablet according to claim 5, wherein dissolution of said tablet is independent of pH over a pH range of about 4 to 8.

7. A single dose applicator (SDA) comprising a tablet according to claim 1, wherein said SDA is a syringe.

8. A drug dispensing device comprising the tablet according to claim 1, wherein said drug dispensing device is effective to check user identification and provide a lockout period between dose dispenses.

9. The tablet according to claim 1, wherein said tablet has a volume of from about 0.5 to about 10.0 microliters.

10. The tablet according to claim 1, wherein said tablet has a volume of from about 1.0 to about 25 microliters.

11. The tablet according to claim 1, wherein said tablet has a volume of from about 3.0 to about 15.0 microliters.

12. The tablet according to claim 1, wherein said tablet comprises 10 micrograms of sufentanil, expressed as the base.

13. The tablet according to claim 1, wherein said tablet comprises 15 micrograms of sufentanil, expressed as the base.

14. The tablet according to claim 1, wherein said tablet has a thickness of from 0.5 to 3.0 mm.

15. The tablet according to claim 1, wherein said tablet disintegrates over a period of 10-30 minutes following sublingual administration to said subject.

16. The tablet according to claim 1, wherein a single or repeated oral transmucosal administration to a subject results in a bioavailability of greater than 70%.

17. The tablet according to claim 1, wherein said tablet further comprises one or more excipients that affect both tablet disintegration kinetics and drug release from said tablet.

18. The tablet according to claim 17, wherein said one or more excipients that affect tablet disintegration kinetics and drug release from said tablet is crosslinked sodium carboxy methylcellulose.

19. The tablet according to claim 1, wherein following administration, said tablet adheres to the oral mucosa of said subject throughout the period of drug delivery.

20. The tablet according to claim 17, wherein a single or repeated oral transmucosal administration to a subject results in a bioavailability of greater than 70%.

21. The SDA according to claim 7, wherein said SDA is effective to accurately place said tablet in the sublingual space.

22. The SDA according to claim 21, wherein said tablet remains dry in said SDA prior to dispensing, at which point a single tablet is dispensed from the SDA into the mouth of said subject.

23. The drug dispensing device according to claim 8, wherein said drug dispensing device is effective to accurately place said tablet in the sublingual area.

24. The drug dispensing device according to claim 23, wherein said tablet remains dry in the drug dispensing device prior to dispensing, at which point a single tablet is dispensed from the drug dispensing device into the mouth of said subject.

25. The drug dispensing device according to claim 23, wherein said drug dispensing device further comprises a user interface wherein dosage history can be transferred to another device, computer or network.

26. The bioadhesive tablet according to claim 1, wherein said tablet exhibits an attachment force of from 0.03 to 0.18 $N/cm^2$ to a porcine mucosa substrate in vitro.

* * * * *